(12) United States Patent
Wang et al.

(10) Patent No.: US 11,834,451 B2
(45) Date of Patent: Dec. 5, 2023

(54) COMPOSITIONS AND METHODS FOR INHIBITING VIRUS PROTEIN 2C ACTIVITY AND FOR PREVENTING AND TREATING NON-POLIO ENTEROVIRUS INFECTION

(71) Applicant: Arizona Board of Regents on Behalf of the University of Arizona, Tucson, AZ (US)

(72) Inventors: Jun Wang, Tucson, AZ (US); Naoya Kitamura, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 59 days.

(21) Appl. No.: 17/705,984

(22) Filed: Mar. 28, 2022

(65) Prior Publication Data

US 2022/0306627 A1    Sep. 29, 2022

Related U.S. Application Data

(60) Provisional application No. 63/167,417, filed on Mar. 29, 2021.

(51) Int. Cl.
*C07D 471/04* (2006.01)

(52) U.S. Cl.
CPC .................. *C07D 471/04* (2013.01)

(58) Field of Classification Search
CPC .................................. C07D 471/04
USPC ................................... 514/210.21
See application file for complete search history.

(56) References Cited

U.S. PATENT DOCUMENTS 8,642,660 B2 * 2/2014 Goldfarb ............. A61K 31/122
514/18.9

OTHER PUBLICATIONS

Baggen, J. et al. The life cycle of non-polio enteroviruses and how to target it. Nat. Rev. Microbiol. 2018, 16, 368-381.
Bauer, L. et al. Direct-acting antivirals and host-targeting strategies to combat enterovirus infections. Curr. Opin. Virol. 2017, 24, 1-8.
Bauer, L. et al. Rational design of highly potent broad-spectrum enterovirus inhibitors targeting the nonstructural protein 20. PLoS Biol. 2020, 18, e3000904.
Bauer, L. et al. Fluoxetine Inhibits Enterovirus Replication by Targeting the Viral 20 Protein in a Stereospecific Manner. ACS Infect. Dis. 2019, 5, 1609-1623.
Bowers, J. R. et al. Genomic Analyses of Acute Flaccid Myelitis Cases among a Cluster in Arizona Provide Further Evidence of Enterovirus D68 Role. mBio 2019, 10, e02262-18.
Brown, D. M. et al. Contemporary Circulating Enterovirus D68 Strains Have Acquired the Capacity for Viral Entry and Replication in Human Neuronal Cells. mBio 2018, 9, e01954-18.
DUNNE, J. L. et al. Rationale for enteroviral vaccination and antiviral therapies in human type 1 diabetes. Diabetologia 2019, 62, 744-753.
Dyda, A. et al. The association between acute flaccid myelitis (AFM) and Enterovirus D68 (EV-D68)—what is the evidence for causation? Euro. Surveill. 2018, 23, 16-24.
Guan, H. et al. Crystal structure of 2C helicase from enterovirus 71. Sci Adv 2017, 3, e1602573.
Guan, H. et al. Crystal structure of a soluble fragment of poliovirus 2CATPase. PLoS Pathog 2018, 14, e1007304.
Hixon, A. M. et al. Evaluating Treatment Efficacy in a Mouse Model of Enterovirus D68-Associated Paralytic Myelitis. J. Infect. Dis. 2017, 216, 1245-1253.
Hixon, A. M. et al. A mouse model of paralytic myelitis caused by enterovirus D68. PLoS Pathog. 2017, 13, e1006199.
Hu, Y. et al. Enterovirus D68 Antivirals: Past, Present, and Future. ACS Infect Dis 2020, 6, 1572-1586.
Hu Y. et al. Boceprevir, calpain inhibitors II and XII, and GC-376 have broad-spectrum antiviral activity against coronaviruses in cell culture. ACS Infect. Dis. 2021, asap.
Hu, Y. et al. The in vitro antiviral activity of lactoferrin against common human coronaviruses and SARS-CoV-2 is mediated by targeting the heparan sulfate co-receptor. Emerg. Microbes Infect. 2021, 10, 317-330.
Hu, Y. et al. Discovery of dapivirine, a nonnucleoside HIV-1 reverse transcriptase inhibitor, as a broad-spectrum antiviral against both influenza A and B viruses. Antiviral Res. 2017, 145, 103-113.
Hurst, B. L. et al. Evaluation of antiviral therapies in respiratory and neurological disease models of Enterovirus D68 infection in mice. Virology 2019, 526, 146-154.
Lim, Z. Q. et al. Recent progress and Challenges in drug development to fight hand, foot and mouth disease. Expert Opin. Drug Discov. 2020, 15, 359-371.
Lin, J. Y. et al. Antivirals and vaccines for Enterovirus A71. J. Biomed. Sci. 2019, 26, 65.
Ma, C. et al. A Novel Capsid Binding Inhibitor Displays Potent Antiviral Activity against Enterovirus D68. ACS Infect. Dis. 2019, 5, 1952-1962.

(Continued)

*Primary Examiner* — Niloofar Rahmani
(74) *Attorney, Agent, or Firm* — Casimir Jones, S.C.; Robert A. Goetz

(57) ABSTRACT

This invention is in the field of medicinal chemistry and relates to a new class of small-molecules having a pyrazolopyridine (or similar) structure (e.g.,

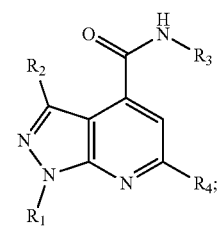

Formula I) which function as inhibitors of the viral protein 2C protein activity and/or expression, and which function as therapeutics for the treatment of viral infection characterized with viral protein 2C activity and/or expression (e.g., non-polio enterovirus infection) (e.g., enterovirus D68 (EV-D68) infection, enterovirus A71 (EV-A71) infection, and coxsackievirus B3 (CVB3) infection.

9 Claims, 11 Drawing Sheets

Specification includes a Sequence Listing.

(56) References Cited

OTHER PUBLICATIONS

Ma, C. et al. Pharmacological Characterization of the Mechanism of Action of R523062, a Promising Antiviral for Enterovirus D68. ACS Infect. Dis. 2020, 6, 2260-2270.

Mao, Q. et al. EV-A71 vaccine licensure: a first step for multivalent enterovirus vaccine to control HFMD and other severe diseases. Emerg. Microbes Infect. 2016, 5, e75.

Martino, T. A. et al. Viral infection and the pathogenesis of dilated cardiomyopathy. Circ. Res. 1994, 74, 182-188.

Messacar, K.; et al. Enterovirus D68 and acute flaccid myelitis-evaluating the evidence for causality. Lancet Infect. Dis. 2018, 18, e239-e247.

Messcar, K.; et al. Safety, tolerability, and efficacy of fluoxetine as an antiviral for acute flaccid myelitis. Neurology 2019, 92, e2118-e2126.

Mishra, N.; et al. Antibodies to Enteroviruses in Cerebrospinal Fluid of Patients with Acute Flaccid Myelitis. mBio 2019, 10, e01903-19.

Morens, D. M.; Folkers, G. K.; Fauci, A. S. Acute Flaccid Myelitis: Something Old and Something New. mBio 2019, 10, e00521-19.

Morrey, J. D.; et al. Causation of Acute Flaccid Paralysis by Myelitis and Myositis in Enterovirus-D68 Infected Mice Deficient in Interferon alphabeta/gamma Receptor Deficient Mice. Viruses 2018, 10, 33.

Murphy, O. C.; Pardo, C. A. Acute Flaccid Myelitis: A Clinical Review. Semin. Neurol. 2020, 40, 211-218.

Musharrafieh, R.; Kitamura, N.; Hu, Y.; Wang, J. Development of broad-spectrum enterovirus antivirals based on quinoline scaffold. Bioorg. Chem. 2020, 101, 103981.

Musharrafieh, R.; Ma, C.; Zhang, J.; Hu, Y.; Diesing, J. M; Marty, M. T.; Wang, J. Validating Enterovirus D68-2A(pro) as an Antiviral Drug Target and the Discovery of Telaprevir as a Potent D68-q2A(pro) Inhibitor. J. Virol. 2019, 93, e02221-18.

Musharrafieh, R.; Zhang, J.; Tuohy, P.; Kitamura, N.; Bellampalli, S. S.; Hu, Y.; Khanna, R.; Wang, J. Discovery of Quinoline Analogues as Potent Antivirals against Enterovirus D68 (EV-D68). J. Med. Chem. 2019, 62, 4074-4090.

Sun, J.; Hu, X. Y.; Yu, X. F. Current Understanding of Human Enterovirus D68. Viruses 2019, 11, 490.

Takeda, M; Pekosz, A.; Shuck, K.; Pinto, L. H.; Lamb, R. A. Influenza a virus M2 ion channel activity is essential for efficient replication in tissue culture. J. Virol. 2002, 76, 1391-9.

Tee, H. K.; Zainol, M. I.; Sam, I. C.; Chan, Y. F. Recent advances in the understanding of enterovirus A71 infection: a focus on neuropathogenesis. Expert Rev. Anti Infect. Ther. 2021, 1-15.

UlfertsS, R.; et al. Screening of a Library of FDA-Approved Drugs Identifies Several Enterovirus Replication Inhibitors That Target Viral Protein 2C. Antimicrob. Agents Chemother. 2016, 60, 2627-2638.

Uprety, P.; Graf, E. H. Enterovirus infection and acute flaccid myelitis. Curr. Opin. Virol. 2020, 40, 55-60.

Volochnyuk, D. M. et al. Approach to the library of fused pyridine-4-carboxylic acids by Combes-type reaction of acyl pyruvates and electron-rich amino heterocycles. J. Comb. Chem. 2010, 12, 510-517.

Wang, S. H.; Wang, K.; Zhao, K.; Hua, S. C.; Du, J. The Structure, Function, and Mechanisms of Action of Enterovirus Non-structural Protein 2C. Front. Microbiol. 2020, 11, 615965.

Wei, M. et al. 2-Year Efficacy, Immunogenicity, and Safety of Vigoo Enterovirus 71 Vaccine in Healthy Chinese Children: A Randomized Open-Label Study. J. Infect. Dis. 2017, 215, 56-63.

Xing, Y.; Zuo, J.; Krogstad, P.; Jung, M. E. Synthesis and Structure-Activity Relationship (SAR) Studies of Novel Pyrazolopyridine Derivatives as Inhibitors of Enterovirus Replication. J. Med. Chem. 2018, 61, 1688-1703.

Zhu, F. C. et al. Efficacy, safety, and immunology of an inactivated alum-adjuvant enterovirus 71 vaccine in children in China: a multicentre, randomised, double-blind, placebo-controlled, phase 3 trial. Lancet 2013, 381, 2024-2032.

Zuo, J.; Kye, S.; Quinn, K. K.; Cooper, P.; Damoiseaux, R.; Krogstad, P. Discovery of Structurally Diverse Small-Molecule Compounds with Broad Antiviral Activity against Enteroviruses. Antimicrob. Agents Chemother. 2015, 60, 1615-1626.

\* cited by examiner

COMPOSITIONS AND METHODS FOR INHIBITING VIRUS PROTEIN 2C ACTIVITY AND FOR PREVENTING AND TREATING NON-POLIO ENTEROVIRUS INFECTION

CROSS REFERENCE TO RELATED APPLICATION

This application claims priority to and the benefit of U.S. Provisional Application No. 63/167,417, filed Mar. 29, 2021, which is hereby incorporated by reference in its entirety.

STATEMENT REGARDING FEDERALLY SPONSORED RESEARCH OR DEVELOPMENT

This invention was made with government support under Grant Nos. AI147325 and AI157046 awarded by National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,000 Byte ASCII (Text) file named "39388-202_ST25" created on Mar. 28, 2022.

FIELD OF THE INVENTION

This invention is in the field of medicinal chemistry and relates to a new class of small-molecules having a pyrazolopyridine (or similar) structure (e.g.,

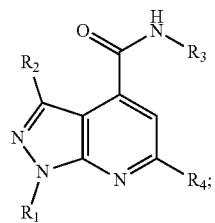

Formula I) which function as inhibitors of the viral protein 2C protein activity and/or expression, and which function as therapeutics for the treatment of viral infection characterized with viral protein 2C activity and/or expression (e.g., non-polio enterovirus infection) (e.g., enterovirus D68 (EV-D68) infection, enterovirus A71 (EV-A71) infection, and coxsackievirus B3 (CVB3) infection.

INTRODUCTION

Non-polio enteroviruses such as enterovirus D68 (EV-D68), EV-A71, and coxsackievirus B3 (CVB3) are important human pathogens that have a significant impact on human health, especially in children.[1] EV-D68, EV-A71, CVB3, along with poliovirus and rhinovirus belong to the enterovirus genera of the piconaviridae virus family. Although poliovirus infection was nearly eliminated by the Global Polio Eradication Initiative through effective vaccination, no vaccines are available in the United States for the non-polio enteroviruses such as EV-D68, EV-A71, and CVB3. Three inactivated EV-A71 vaccines are available in China.[2-4] However, their efficacy is limited to certain strains and is not broadly protective.[5]

Therefore, it is imperative to develop small molecule antivirals as therapeutics.[5-8]

The present invention addresses these needs.

SUMMARY

Drug discovery efforts on non-polio enterovirus antivirals gained momentum in recent years due to the increasing number of infections and severity of the disease outcomes caused by EV-D68, EV-A71, and CVB3. EV-D68 infection typically leads to moderate flu-like respiratory illness and it is self-limiting.[9-10] EV-D68 spreads through the respiratory tract, similar to rhinoviruses. However, contemporary EV-D68 strains appear to evolve and become more virulent compared to historic strains.[11] For example, recent EV-D68 outbreaks in 2014, 2016, and 2018 coincided with increasing numbers of severe respiratory illness and neurological complications such as acute flaccid myelitis (AFM), meningitis, and encephalitis.[10, 12-14] It has been demonstrated in cell culture that contemporary EV-D68 strains, but not historic strains, were able to infect neuronal cells and cause cytopathic effect.[11] In mouse model study, EV-D68 virus was shown to infiltrate the blood brain barrier and infect the central nervous system (CNS) such as the spinal cord.[15-19] Although EV-D68 virus is rarely detected in the human patient CNS tissues, there is nevertheless a positive correlation between EV-D68 infection and neurological complications as shown by a number of studies.[20, 21] Recent studies have shown that antibodies reacting to the EV-D68 viral capsid protein VP1 have been detected in high frequency in the CSF fluid samples from AFM patients.[21] EV-A71 is one of the etiological agents for hand, foot, and mouth disease (HFMD) and spreads through the fecal-oral route. Several EV-A71 outbreaks in the Asia-Pacific region have resulted in thousands of deaths.[5] Similar to EV-D68, EV-A71 is also a neurotropic virus, and in rare cases EV-A71 infection can cause severe neurological complications with a high mortality and morbidity rate in infants and young children.[22, 23] CVB3 virus is the causative agent for viral myocarditis.[24] In addition, CVB3 infection is also linked to type 1 diabetes mellitus and idiopathic chronic pancreatitis due to chronic pancreatic inflammation induced by the virus.[25]

Several compounds have been reported in the literature as non-polio antivirals with varying degrees of potency, selectivity index, and antiviral spectrum.[1, 5, 7, 26] Prominent examples include viral capsid inhibitors such as pleconaril, the viral protease inhibitor rupintrivir, the 3D polymerase inhibitors ribavirin and gemcitabine, as well as the viral 2C inhibitors dibucaine and fluoxetine.[27-32] Most of these reported compounds are either repurposed from rhinovirus antivirals (pleconaril and rupintrivir) or FDA-approved drugs for other disease indications (fluoxetine, dibucaine, and ribavirin).[27] As these compounds were not specifically developed for EV-D68, EV-A71 or CVB3, their antiviral specificity, potency, and selectivity index need to be significantly improved for clinical use as non-polio enterovirus antivirals. Notably, EV-D68 antiviral development is left far behind compared to EV-A71 and CVB3,[7] possibly because it is an emerging pathogen that only comes to public attention in recent years.

Experiments conducted during the course of developing embodiments for the present invention developed broad-acting non-polio enterovirus antivirals against EV-D68, EV-A71, and CVB3. Indeed, such experiments identified a class of pyrazolopyridine analogs that have shown broad-spectrum antiviral activity against EV-D68, EV-A71, and CVB3. The primary hit, compound 7a, was identified through a cytopathic effect (CPE) assay screening against EV-D68 virus.[33, 34] Encouragingly, compound 7a was also active against EV-A71.

Subsequent structure-activity relationship (SAR) studies yielded several lead compounds including 7d that inhibited different strains of EV-D68, EV-A71 and CVB3 with $EC_{50}$ values in the nanomolar range and a selectivity index of over 500. The antiviral activity was also consistent between the RD cell (muscle cell) and the SH-SYSY cell (neuronal cell). Mechanistic studies have shown that the pyrazolopyridine analogs target the conserved viral 2C protein. The enterovirus 2C protein is a multifunctional protein that forms hexamer with ATPase activity.[35, 36] The recognized functions of 2C include viral RNA binding and replication, membrane remodeling, and encapsulation.[37] Structurally diverse compounds have been identified as 2C inhibitors (FIG. 1)[26-29, 32, 33] It is noted that an earlier study similarly reported the pyrazolopyridine derivatives such as JX040 as enterovirus antivirals (FIG. 1).[26] Those compounds had antiviral activity against EV-A71, CVB3, and poliovirus-1, but their antiviral activity was not tested against the EV-D68. Although mechanistic studies were not pursued, an earlier study from the same group showed that similar compounds inhibited the CVB3 virus by targeting the viral 2C protein.[31] Although the compounds described in the experiments described herein such as 7d share the same pyrazolopyridine core with the ones reported earlier such as JX040, the structure-activity relationships appear to be different. For example, compounds in the earlier study such as JX040 had neutral aromatic amide substitutions at the 4-position, while the compounds described herein such as 7d prefer positively charged amine at the same position. In addition, compounds reported earlier had aromatic substitutions at the 6-position, while the compounds described herein contain hydrophobic alkyl substitutions. Given that both classes of compounds showed broad-spectrum antiviral activity against non-polio enteroviruses, it might be possible that they target different regions in the 2C protein. Overall, the pyrazolopyridine compounds represent one of the most potent and selective classes of non-polio enterovirus antivirals.

Accordingly, the present invention relates to a new class of small-molecules having a pyrazolopyridine (or similar) structure which function as inhibitors of the viral protein 2C protein activity and/or expression, and which function as therapeutics for the treatment of viral infection characterized with viral protein 2C activity and/or expression (e.g., non-polio enterovirus infection) (e.g., enterovirus D68 (EV-D68) infection, enterovirus A71 (EV-A71) infection, and coxsackievirus B3 (CVB3) infection.

Certain pyrazolopyridine (or similar) compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, compounds encompassed within Formula I are provided:

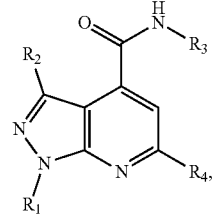

(Formula I)

including pharmaceutically acceptable salts, solvates, and/or prodrugs thereof.

Formula I is not limited to a particular chemical moiety for R1, R2, R3, and R4. In some embodiments, the particular chemical moiety for R1, R2, R3, and R4 independently include any chemical moiety that permits the resulting compound to inhibit viral 2C protein activity. In some embodiments, the particular chemical moiety R1, R2, R3, and R4 independently include any chemical moiety that permits the resulting compound to prevent, treat, and/or ameliorate symptoms related to non-polio enterovirus infection. In some embodiments, the particular chemical moiety R1, R2, R3, and R4 independently include any chemical moiety that permits the resulting compound to prevent, treat, and/or ameliorate symptoms related to EV-D68 infection. In some embodiments, the particular chemical moiety R1, R2, R3, and R4 independently include any chemical moiety that permits the resulting compound to prevent, treat, and/or ameliorate symptoms related to EV-A71 infection. In some embodiments, the particular chemical moiety R1, R2, R3, and R4 independently include any chemical moiety that permits the resulting compound to prevent, treat, and/or ameliorate symptoms related to CVB3 infection.

Such embodiments are not limited to a particular definition for R1.

In some embodiments, R1 is selected from hydrogen, $CH_3$,

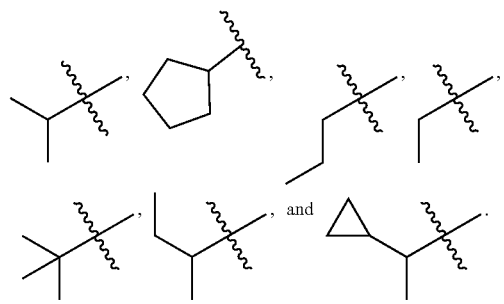

Such embodiments are not limited to a particular definition for R2.

In some embodiments, R2 is selected from hydrogen and $CH_3$.

Such embodiments are not limited to a particular definition for R3.

In some embodiments, R3 is selected from hydrogen,

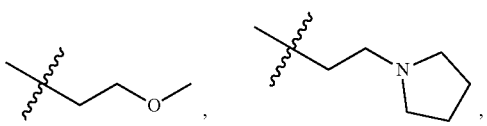

-continued

[chemical structures]

Such embodiments are not limited to a particular definition for R4.

In some embodiments, R4 is selected from hydrogen, CH₃,

[chemical structures], and .

In some embodiments, the compound is recited in Table 1 (see, Example I).

The invention further provides processes for preparing any of the compounds of the present invention.

In certain embodiments, the present invention provides methods for administering a pharmaceutical composition comprising one or more compounds of the present invention to a subject (e.g., a human subject) (e.g., a human subject suffering from or at risk of suffering from a condition related to viral protein 2C activity (e.g., EV-D68 infection, EV-A71 infection, and/or CVB3 infection) for purposes of treating, preventing and/or ameliorating the symptoms of a viral infection (e.g., EV-D68 infection, EV-A71 infection, and/or CVB3 infection).

In such embodiments, the methods are not limited treating, preventing and/or ameliorating the symptoms of a particular type or kind of viral infection. In some embodiments, the viral infection is any viral infection characterized with viral protein 2C activity. In some embodiments, the viral infection is any non-polio enterovirus infection (e.g., infection related to Coxsackie A viruses, infection related Coxsackie B viruses, infection related to echoviruses, infection related to enteroviruses). In some embodiments, the viral infection is any viral infection characterized with viral protein 2C activity. In some embodiments, the viral infection is EV-D68 infection, EV-A71 infection, and/or CVB3 infection.

In such embodiments, administration of the pharmaceutical composition results in suppression of viral protein 2C activity within the subject. In some embodiments, administration of the pharmaceutical composition results in suppression of any pathway related activity related to viral protein 2C activity within the subject.

In some embodiments, the pharmaceutical composition comprising one or more compounds of the present invention is co-administered with one or more of pleconaril, human lactoferrin, bovine lactoferrin, and ribavirin.

In certain embodiments, the present invention provides methods for treating, ameliorating and/or preventing a condition related to viral infection in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to viral protein 2C activity. In some embodiments, the viral infection is any non-polio enterovirus infection (e.g., infection related to Coxsackie A viruses, infection related Coxsackie B viruses, infection related to echoviruses, infection related to enteroviruses). In some embodiments, the viral infection is any viral infection characterized with viral protein 2C activity. In some embodiments, the viral infection is EV-D68 infection, EV-A71 infection, and/or CVB3 infection.

In certain embodiments, the present invention provides methods for treating, ameliorating and/or preventing non-polio enterovirus infection in a subject, comprising administering to the subject a pharmaceutical composition comprising one or more compounds of the present invention. In some embodiments, the pharmaceutical composition comprising one or more compounds of the present invention is configured for oral administration. In some embodiments, the subject is a human subject. In some embodiments, the non-polio enterovirus infection is any viral infection characterized with viral protein 2C activity. In some embodiments, the non-polio enterovirus infection is EV-D68 infection, EV-A71 infection, and/or CVB3 infection.

In certain embodiments, the present invention provides methods for treating, ameliorating and/or preventing EV-D68 infection in a subject, comprising administering to the subject a pharmaceutical composition comprising one or more compounds of the present invention. In some embodiments, the pharmaceutical composition comprising one or more compounds of the present invention is configured for oral administration. In some embodiments, the subject is a human subject.

In certain embodiments, the present invention provides methods for treating, ameliorating and/or preventing EV-A71 infection in a subject, comprising administering to the subject a pharmaceutical composition comprising one or more compounds of the present invention. In some embodiments, the pharmaceutical composition comprising one or more compounds of the present invention is configured for oral administration. In some embodiments, the subject is a human subject.

In certain embodiments, the present invention provides methods for treating, ameliorating and/or preventing CVB3 infection in a subject, comprising administering to the subject a pharmaceutical composition comprising one or more compounds of the present invention. In some embodiments, the pharmaceutical composition comprising one or more compounds of the present invention is configured for oral administration. In some embodiments, the subject is a human subject.

In certain embodiments, the present invention provides methods for treating, ameliorating and/or preventing acute flaccid myelitis related to viral infection (e.g., non-polio enterovirus infection) (e.g., viral infection characterized with virus protein 2C activity) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing hand, foot, and mouth disease (HFMD) related to viral infection (e.g., non-polio enterovirus infection) (e.g., viral infection characterized with virus protein 2C activity) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing cardiac arrhythmias related to viral infection (e.g., non-polio enterovirus infection) (e.g., viral infection characterized with virus protein 2C activity) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing acute heart failure related to viral infection (e.g., non-polio enterovirus infection) (e.g., viral infection characterized with virus protein 2C activity) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing type 1 diabetes related to viral infection (e.g., non-polio enterovirus infection) (e.g., viral infection characterized with virus protein 2C activity) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing acute flaccid myelitis related to an infection characterized with viral protein 2C activity (e.g., non-polio enterovirus infection) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing hand, foot, and mouth disease (HFMD) related to an infection characterized with viral protein 2C activity (e.g., non-polio enterovirus infection) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing cardiac arrhythmias related to an infection characterized with viral protein 2C activity (e.g., non-polio enterovirus infection) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing acute heart failure related to an infection characterized with viral protein 2C activity (e.g., non-polio enterovirus infection) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing type 1 diabetes related to an infection characterized with viral protein 2C activity (e.g., non-polio enterovirus infection) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing symptoms related to viral infection in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from EV-D68 infection, EV-A71 infection, and/or CVB3 infection. In some embodiments, the subject is a human subject suffering from a viral infection characterized with viral 2C protein activity. In some embodiments, the subject is a human subject suffering from or at risk of suffering from any non-polio enterovirus infection (e.g., infection related to Coxsackie A viruses, infection related Coxsackie B viruses, infection related to echoviruses, infection related to enteroviruses). In some embodiments, the one or more symptoms related to viral infection includes, but is not limited to, acute flaccid myelitis, HFMD, cardiac arrythmia, acute heart failure, type 1 diabetes, acute fever, fatigue, dry cough, myalgias, dyspnea, acute respiratory distress syndrome, and pneumonia.

In certain embodiments, the present invention provides methods for treating, ameliorating and/or preventing symptoms related to viral infection (e.g., infection related to Coxsackie A viruses, infection related Coxsackie B viruses, infection related to echoviruses, infection related to enteroviruses) (e.g., EV-D68 infection, EV-A71 infection, CVB3 infection) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the one or more symptoms related to viral infection includes, but is not limited to, acute flaccid myelitis, HFMD, cardiac arrythmia, acute heart failure, type 1 diabetes, acute fever, fatigue, dry cough, myalgias, dyspnea, acute respiratory distress syndrome, and pneumonia.

In some embodiments involving the treatment, prevention, and/or amelioration of symptoms related to viral infection (e.g., infection related to Coxsackie A viruses, infection related Coxsackie B viruses, infection related to echoviruses, infection related to enteroviruses) (e.g., EV-D68 infection, EV-A71 infection, CVB3 infection), the pharmaceutical composition is administered in combination with one or more of anti-asthma agent/therapies, anti-rhinitis agents/therapies, anti-sinusitis agents/therapies, anti-emphysema agents/therapies, anti-bronchitis agents/therapies or anti-chronic obstructive pulmonary disease agents/therapies. Anti-asthma agents/therapies include mast cell degranulation agents, leukotriene inhibitors, corticosteroids, beta-antagonists, IgE binding inhibitors, anti-CD23 antibody, tryptase inhibitors, and VIP agonists. Anti-allergic rhinitis agents/therapies include H1 antihistamines, alpha-adrenergic agents, and glucocorticoids. Anti-chronic sinusitis therapies include, but are not limited to, surgery, corticosteroids, antibiotics, anti-fungal agents, salt-water nasal washes or sprays, anti-inflammatory agents, decongestants, guaifensesin, potassium iodide, luekotriene inhibitors, mast cell degranulating agents, topical moisterizing agents, hot air inhalation, mechanical breathing devices, enzymatic cleaners and antihistamine sprays. Anti-emphysema, anti-bronchitis or anti-chronic obstructive pulmonary disease agents/therapies include, but are not limited to oxygen, bronchodilator agents, mycolytic agents, steroids, antibiotics, anti-fungals, moisturization by nebulization, anti-tussives, respiratory stimulants, surgery and alpha 1 antitrypsin.

In certain embodiments, the present invention provides methods for inhibiting viral entry in a cell, comprising exposing the cell to a pharmaceutical composition comprising one or more compounds of the present invention. In some embodiments, the cell is at risk of viral infection (e.g., infection related to Coxsackie A viruses, infection related Coxsackie B viruses, infection related to echoviruses, infection related to enteroviruses) (e.g., a cell at risk of EV-D68 infection, EV-A71 infection, CVB3 infection). In some embodiments, the cell has been exposed to a virus (e.g., a cell currently exposed to EV-D68, EV-A71, CVB3). In some embodiments, the cell is in culture. In some embodiments, the cell is a living cell in a subject (e.g., a human subject) (e.g., a human subject suffering from or at risk of suffering from EV-D68 infection, EV-A71 infection, CVB3 infection). In some embodiments, exposure of the cell to the pharmaceutical composition comprising one or more compounds of the present invention results in suppression of viral protein 2C activity within the cell.

In certain embodiments, the present invention provides kits comprising a pharmaceutical composition comprising one or more compounds of the present invention, and one or more of (1) a container, pack, or dispenser, (2) one or more additional agents for treating viral infection, and (3) instructions for administration.

DETAILED DESCRIPTION OF THE INVENTION

Figure 1:
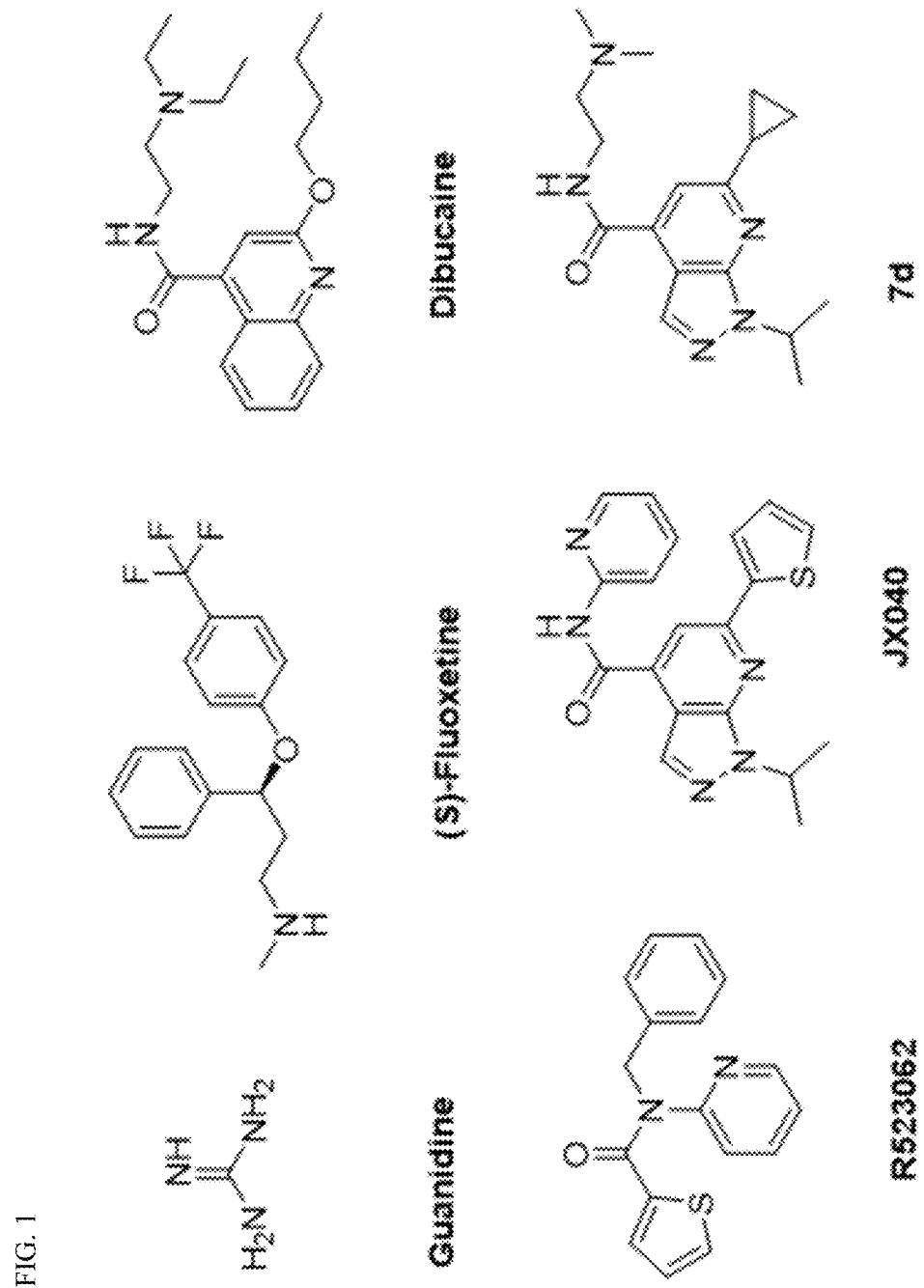
FIG. 1 shows structurally diverse enterovirus 2C inhibitors. The most potent enterovirus 2C inhibitor is compound 7d.

The non-polio enterovirus genera of the picornavirus family contains many important human pathogens including enterovirus D68 (EV-D68), EV-A71, and coxsackievirus B3 (CVB3). EV-D68 primarily infects children and the disease manifestations range from respiratory illnesses to neurological complications such as acute flaccid myelitis (AFM). EV-A71 is a major pathogen for the hand, foot, and mouth disease (HFMD) in children and can also lead to AFM and death in severe cases. CVB3 infection can cause cardiac arrhythmias, acute heart failure, as well as type 1 diabetes. There is currently no FDA-approved antiviral for any of these enteroviruses.

Experiments conducted during the course of developing embodiments for the present invention aimed to address this unmet medical need by developing potent and broad-spectrum antivirals against non-polio enteroviruses. Such experiments resulted in the discovery and development of pyrazolopyridine-containing small molecules with potent and broad-spectrum antiviral activity and a high selectivity index against multiple strains of EV-D68, EV-A71, and CVB3 in cell culture. Serial viral passage experiments, coupled with reverse genetics and thermal shift binding assays, indicated that these molecules target the conserved viral protein 2C. Overall, the pyrazolopyridine inhibitors described herein represent a promising class of candidates for the urgently needed non-polio enterovirus antivirals.

Accordingly, the present invention relates to a new class of small-molecules having a pyrazolopyridine (or similar) structure which function as inhibitors of the viral protein 2C protein activity and/or expression, and which function as therapeutics for the treatment of viral infection characterized with viral protein 2C activity and/or expression (e.g., non-polio enterovirus infection) (e.g., enterovirus D68 (EV-D68) infection, enterovirus A71 (EV-A71) infection, and coxsackievirus B3 (CVB3) infection.

In a particular embodiment, compounds encompassed within Formula I are provided:

(Formula I)

including pharmaceutically acceptable salts, solvates, and/or prodrugs thereof.

Formula I is not limited to a particular chemical moiety for R1, R2, R3, and R4. In some embodiments, the particular chemical moiety for R1, R2, R3, and R4 independently include any chemical moiety that permits the resulting compound to inhibit viral 2C protein activity. In some embodiments, the particular chemical moiety R1, R2, R3, and R4 independently include any chemical moiety that permits the resulting compound to prevent, treat, and/or ameliorate symptoms related to non-polio enterovirus infection. In some embodiments, the particular chemical moiety R1, R2, R3, and R4 independently include any chemical moiety that permits the resulting compound to prevent, treat, and/or ameliorate symptoms related to EV-D68 infection. In some embodiments, the particular chemical moiety R1, R2, R3, and R4 independently include any chemical moiety that permits the resulting compound to prevent, treat, and/or ameliorate symptoms related to EV-A71 infection. In some embodiments, the particular chemical moiety R1, R2, R3, and R4 independently include any chemical moiety that permits the resulting compound to prevent, treat, and/or ameliorate symptoms related to CVB3 infection.

Such embodiments are not limited to a particular definition for R1.

In some embodiments, R1 is selected from hydrogen, $CH_3$,

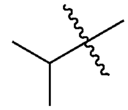

, 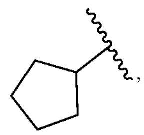 , 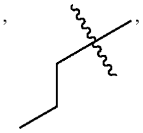 , 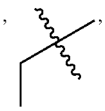 , 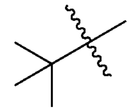 , 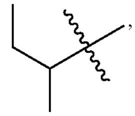 , and 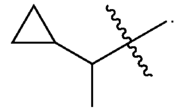 .

Such embodiments are not limited to a particular definition for R2.

In some embodiments, R2 is selected from hydrogen and $CH_3$.

Such embodiments are not limited to a particular definition for R3.

In some embodiments, R3 is selected from hydrogen,

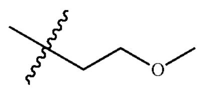

, 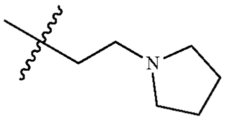 , 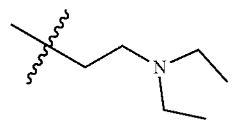 , 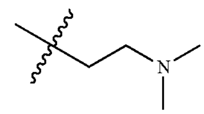 , 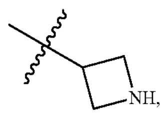 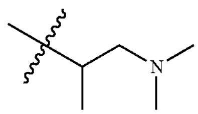  , 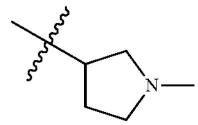 , 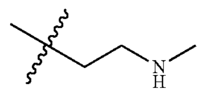 , 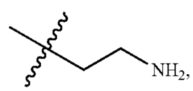  , 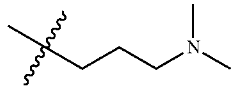 , 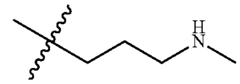 , 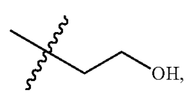 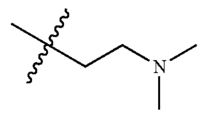  , and 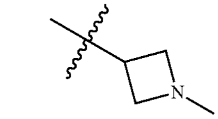 .

Such embodiments are not limited to a particular definition for R4.

In some embodiments, R4 is selected from hydrogen, $CH_3$,

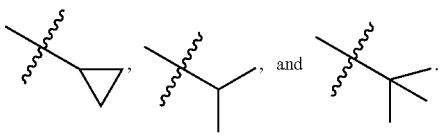

In some embodiments, the compound is recited in Table 1 (see, Example I).

The invention further provides processes for preparing any of the compounds of the present invention.

An important aspect of the present invention is that the pharmaceutical compositions comprising one or more of compounds of the present invention are useful in treating non-polio enterovirus infection (e.g., infection related to Coxsackie A viruses, infection related Coxsackie B viruses, infection related to echoviruses, infection related to enteroviruses) (e.g., EV-D68 infection, EV-A71 infection, and/or CVB3 infection). and symptoms related to such a viral infection (e.g., acute flaccid myelitis, HFMD, cardiac arrythmias, acute heart failure, type 1 diabetes, fever, fatigue, dry cough, myalgias, dyspnea, acute respiratory distress syndrome, and pneumonia).

Some embodiments of the present invention provide methods for administering an effective amount of a pharmaceutical composition comprising one or more compounds of the present invention and at least one additional therapeutic agent (including, but not limited to, any pharmaceutical agent useful in treating a viral infection (e.g., infection related to Coxsackie A viruses, infection related Coxsackie B viruses, infection related to echoviruses, infection related to enteroviruses) (e.g., viral infection characterized with viral protein 2C activity) (e.g., EV-D68 infection) (e.g., EV-A71 infection) (e.g., CVB3 infection) and/or symptoms related to such a viral infection (e.g., acute flaccid myelitis, HFMD, cardiac arrythmias, acute heart failure, type 1 diabetes, fever, fatigue, dry cough, myalgias, dyspnea, acute respiratory distress syndrome, and pneumonia).

In certain embodiments, the present invention provides methods for administering a pharmaceutical composition comprising one or more compounds of the present invention to a subject (e.g., a human subject) (e.g., a human subject suffering from or at risk of suffering from a condition related to viral protein 2C activity (e.g., EV-D68 infection, EV-A71 infection, and/or CVB3 infection) for purposes of treating, preventing and/or ameliorating the symptoms of a viral infection (e.g., EV-D68 infection, EV-A71 infection, and/or CVB3 infection).

In such embodiments, the methods are not limited treating, preventing and/or ameliorating the symptoms of a particular type or kind of viral infection. In some embodiments, the viral infection is any viral infection characterized with viral protein 2C activity. In some embodiments, the viral infection is any non-polio enterovirus infection (e.g., infection related to Coxsackie A viruses, infection related Coxsackie B viruses, infection related to echoviruses, infection related to enteroviruses). In some embodiments, the viral infection is any viral infection characterized with viral protein 2C activity. In some embodiments, the viral infection is EV-D68 infection, EV-A71 infection, and/or CVB3 infection.

In such embodiments, administration of the pharmaceutical composition results in suppression of viral protein 2C activity within the subject. In some embodiments, administration of the pharmaceutical composition results in suppression of any pathway related activity related to viral protein 2C activity within the subject.

In some embodiments, the pharmaceutical composition comprising one or more compounds of the present invention is co-administered with one or more of pleconaril, human lactoferrin, bovine lactoferrin, and ribavirin.

In certain embodiments, the present invention provides methods for treating, ameliorating and/or preventing a condition related to viral infection in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to viral protein 2C activity. In some embodiments, the viral infection is any non-polio enterovirus infection (e.g., infection related to Coxsackie A viruses, infection related Coxsackie B viruses, infection related to echoviruses, infection related to enteroviruses). In some embodiments, the viral infection is any viral infection characterized with viral protein 2C activity. In some embodiments, the viral infection is EV-D68 infection, EV-A71 infection, and/or CVB3 infection.

In certain embodiments, the present invention provides methods for treating, ameliorating and/or preventing non-polio enterovirus infection in a subject, comprising administering to the subject a pharmaceutical composition comprising one or more compounds of the present invention. In some embodiments, the pharmaceutical composition comprising one or more compounds of the present invention is configured for oral administration. In some embodiments, the subject is a human subject. In some embodiments, the non-polio enterovirus infection is any viral infection characterized with viral protein 2C activity. In some embodiments, the non-polio enterovirus infection is EV-D68 infection, EV-A71 infection, and/or CVB3 infection.

In certain embodiments, the present invention provides methods for treating, ameliorating and/or preventing EV-D68 infection in a subject, comprising administering to the subject a pharmaceutical composition comprising one or more compounds of the present invention. In some embodiments, the pharmaceutical composition comprising one or more compounds of the present invention is configured for oral administration. In some embodiments, the subject is a human subject.

In certain embodiments, the present invention provides methods for treating, ameliorating and/or preventing EV-A71 infection in a subject, comprising administering to the subject a pharmaceutical composition comprising one or more compounds of the present invention. In some embodiments, the pharmaceutical composition comprising one or more compounds of the present invention is configured for oral administration. In some embodiments, the subject is a human subject.

In certain embodiments, the present invention provides methods for treating, ameliorating and/or preventing CVB3 infection in a subject, comprising administering to the subject a pharmaceutical composition comprising one or more compounds of the present invention. In some embodiments, the pharmaceutical composition comprising one or more compounds of the present invention is configured for oral administration. In some embodiments, the subject is a human subject.

In certain embodiments, the present invention provides methods for treating, ameliorating and/or preventing acute flaccid myelitis related to viral infection (e.g., non-polio enterovirus infection) (e.g., viral infection characterized with virus protein 2C activity) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing hand, foot, and mouth disease (HFMD) related to viral infection (e.g., non-polio enterovirus infection) (e.g., viral infection characterized with virus protein 2C activity) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing cardiac arrhythmias related to viral infection (e.g., non-polio enterovirus infection) (e.g., viral infection characterized with virus protein 2C activity) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing acute heart failure related to viral infection (e.g., non-polio enterovirus infection) (e.g., viral infection characterized with virus protein 2C activity) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing type 1 diabetes related to viral infection (e.g., non-polio enterovirus infection) (e.g., viral infection characterized with virus protein 2C activity) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing acute flaccid myelitis related to an infection characterized with viral protein 2C activity (e.g., non-polio enterovirus infection) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing hand, foot, and mouth disease (HFMD) related to an infection characterized with viral protein 2C activity (e.g., non-polio enterovirus infection) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing cardiac arrhythmias related to an infection characterized with viral protein 2C activity (e.g., non-polio enterovirus infection) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing acute heart failure related to an infection characterized with viral protein 2C activity (e.g., non-polio enterovirus infection) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing type 1 diabetes related to an infection characterized with viral protein 2C activity (e.g., non-polio enterovirus infection) (e.g., EV-D68 infection, EV-A71 infection, CVB3 infection), comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject.

In certain embodiments, the present invention provides methods for treating, ameliorating and/or preventing symptoms related to viral infection in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from EV-D68 infection, EV-A71 infection, and/or CVB3 infection. In some embodiments, the subject is a human subject suffering from a viral infection characterized with viral 2C protein activity. In some embodiments, the subject is a human subject suffering from or at risk of suffering from any non-polio enterovirus infection (e.g., infection related to Coxsackie A viruses, infection related Coxsackie B viruses, infection related to echoviruses, infection related to enteroviruses). In some embodiments, the one or more symptoms related to viral infection includes, but is not limited to, acute flaccid myelitis, HFMD, cardiac arrythmia, acute heart failure, type 1 diabetes, acute fever, fatigue, dry cough, myalgias, dyspnea, acute respiratory distress syndrome, and pneumonia.

In certain embodiments, the present invention provides methods for treating, ameliorating and/or preventing symptoms related to viral infection (e.g., infection related to Coxsackie A viruses, infection related Coxsackie B viruses, infection related to echoviruses, infection related to enteroviruses) (e.g., EV-D68 infection, EV-A71 infection, CVB3 infection) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the one or more symptoms related to viral infection includes, but is not limited to, acute flaccid myelitis, HFMD, cardiac arrythmia, acute heart failure, type 1 diabetes, acute fever, fatigue, dry cough, myalgias, dyspnea, acute respiratory distress syndrome, and pneumonia.

In some embodiments involving the treatment, prevention, and/or amelioration of symptoms related to viral infection (e.g., infection related to Coxsackie A viruses, infection related Coxsackie B viruses, infection related to echoviruses, infection related to enteroviruses) (e.g., EV-D68 infection, EV-A71 infection, CVB3 infection), the pharmaceutical composition is administered in combination with one or more of anti-asthma agent/therapies, anti-rhinitis agents/therapies, anti-sinusitis agents/therapies, anti-emphysema agents/therapies, anti-bronchitis agents/therapies or anti-chronic obstructive pulmonary disease agents/therapies. Anti-asthma agents/therapies include mast cell degranulation agents, leukotriene inhibitors, corticosteroids, beta-antagonists, IgE binding inhibitors, anti-CD23 antibody, tryptase inhibitors, and VIP agonists. Anti-allergic rhinitis agents/therapies include H1 antihistamines, alpha-adrenergic agents, and glucocorticoids. Anti-chronic sinusitis therapies include, but are not limited to surgery, corticosteroids, antibiotics, anti-fungal agents, salt-water nasal washes or sprays, anti-inflammatory agents, decongestants, guaifensesin, potassium iodide, luekotriene inhibitors, mast cell degranulating agents, topical moisterizing agents, hot air inhalation, mechanical breathing devices, enzymatic cleaners and antihistamine sprays. Anti-emphysema, anti-bronchitis or anti-chronic obstructive pulmonary disease agents/therapies include, but are not limited to oxygen, bronchodilator agents, mycolytic agents, steroids, antibiotics, anti-fungals, moisturization by nebulization, anti-tussives, respiratory stimulants, surgery and alpha 1 antitrypsin.

In certain embodiments, the present invention provides methods for inhibiting viral entry in a cell, comprising exposing the cell to a pharmaceutical composition comprising one or more compounds of the present invention. In some embodiments, the cell is at risk of viral infection (e.g., infection related to Coxsackie A viruses, infection related Coxsackie B viruses, infection related to echoviruses, infection related to enteroviruses) (e.g., a cell at risk of EV-D68 infection, EV-A71 infection, CVB3 infection). In some embodiments, the cell has been exposed to a virus (e.g., a cell currently exposed to EV-D68, EV-A71, CVB3). In some embodiments, the cell is in culture. In some embodiments, the cell is a living cell in a subject (e.g., a human subject) (e.g., a human subject suffering from or at risk of suffering from EV-D68 infection, EV-A71 infection, CVB3 infection). In some embodiments, exposure of the cell to the pharmaceutical composition comprising one or more compounds of the present invention results in suppression of viral protein 2C activity within the cell.

In certain embodiments, the present invention provides kits comprising a pharmaceutical composition comprising one or more compounds of the present invention, and one or more of (1) a container, pack, or dispenser, (2) one or more additional agents for treating viral infection, and (3) instructions for administration Compositions within the scope of this invention include all pharmaceutical compositions contained in an amount that is effective to achieve its intended purpose. While individual needs vary, determination of optimal ranges of effective amounts of each component is within the skill of the art. Typically, the pharmaceutical agents which function as inhibitors of $PL^{pro}$ protease activity may be administered to mammals, e.g. humans, orally at a dose of 0.0025 to 50 mg/kg, or an equivalent amount of the pharmaceutically acceptable salt thereof, per day of the body weight of the mammal being treated. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the inhibiting agent. The unit dose may be administered one or more times daily as one or more tablets or capsules each containing from about 0.1 to about 10 mg, conveniently about 0.25 to 50 mg of the agent (e.g., small molecule) or its solvates.

In a topical formulation, a compound of the present invention (e.g., a comound having a pyrazolopyridine structure) may be present at a concentration of about 0.01 to 100 mg per gram of carrier. In a one embodiment, such a compound is present at a concentration of about 0.07-1.0 mg/ml, for example, about 0.1-0.5 mg/ml, and in one embodiment, about 0.4 mg/ml.

In addition to administering a compound of the present invention as a raw chemical, it may be administered as part of a pharmaceutical preparation containing suitable pharmaceutically acceptable carriers comprising excipients and auxiliaries which facilitate processing of the compound into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active mimetic peptide(s), together with the excipient.

The pharmaceutical compositions of the invention may be administered to any patient that may experience the beneficial effects of one or more of compounds of the present invention. Foremost among such patients are mammals, e.g., humans, although the invention is not intended to be so limited. Other patients include veterinary animals (cows, sheep, pigs, horses, dogs, cats and the like).

The pharmaceutical compositions comprising a compound of the present invention (e.g., a compound having a pyrazolopyridine structure) may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner that is itself known, for example, by means of conventional mixing, granulating, dragee-making, dissolving, or lyophilizing processes. Thus, pharmaceutical preparations for oral use can be obtained by combining the active mimetic peptides with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye-stuffs or pigments may be added to the tablets or dragee coatings, for example, for identification or in order to characterize combinations of active mimetic peptide doses.

Other pharmaceutical preparations that can be used orally include push-fit capsules made of gelatin, as well as soft, sealed capsules made of gelatin and a plasticizer such as glycerol or sorbitol. The push-fit capsules can contain the active mimetic peptides in the form of granules that may be mixed with fillers such as lactose, binders such as starches, and/or lubricants such as talc or magnesium stearate and, optionally, stabilizers. In soft capsules, the active mimetic peptides are in one embodiment dissolved or suspended in suitable liquids, such as fatty oils, or liquid paraffin. In addition, stabilizers may be added.

Possible pharmaceutical preparations that can be used rectally include, for example, suppositories, which consist of a combination of one or more of the active mimetic peptides with a suppository base. Suitable suppository bases are, for example, natural or synthetic triglycerides, or paraffin hydrocarbons. In addition, it is also possible to use gelatin rectal capsules that consist of a combination of the active mimetic peptides with a base. Possible base materials include, for example, liquid triglycerides, polyethylene glycols, or paraffin hydrocarbons.

Suitable formulations for parenteral administration include aqueous solutions of the active mimetic peptides in water-soluble form, for example, water-soluble salts and alkaline solutions. In addition, suspensions of the active mimetic peptides as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one that includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXPERIMENTAL

Use of pronouns within the Experimental section pertains to the inventors of the invention(s) described herein.

Example I

Chemistry

Figure 2A:
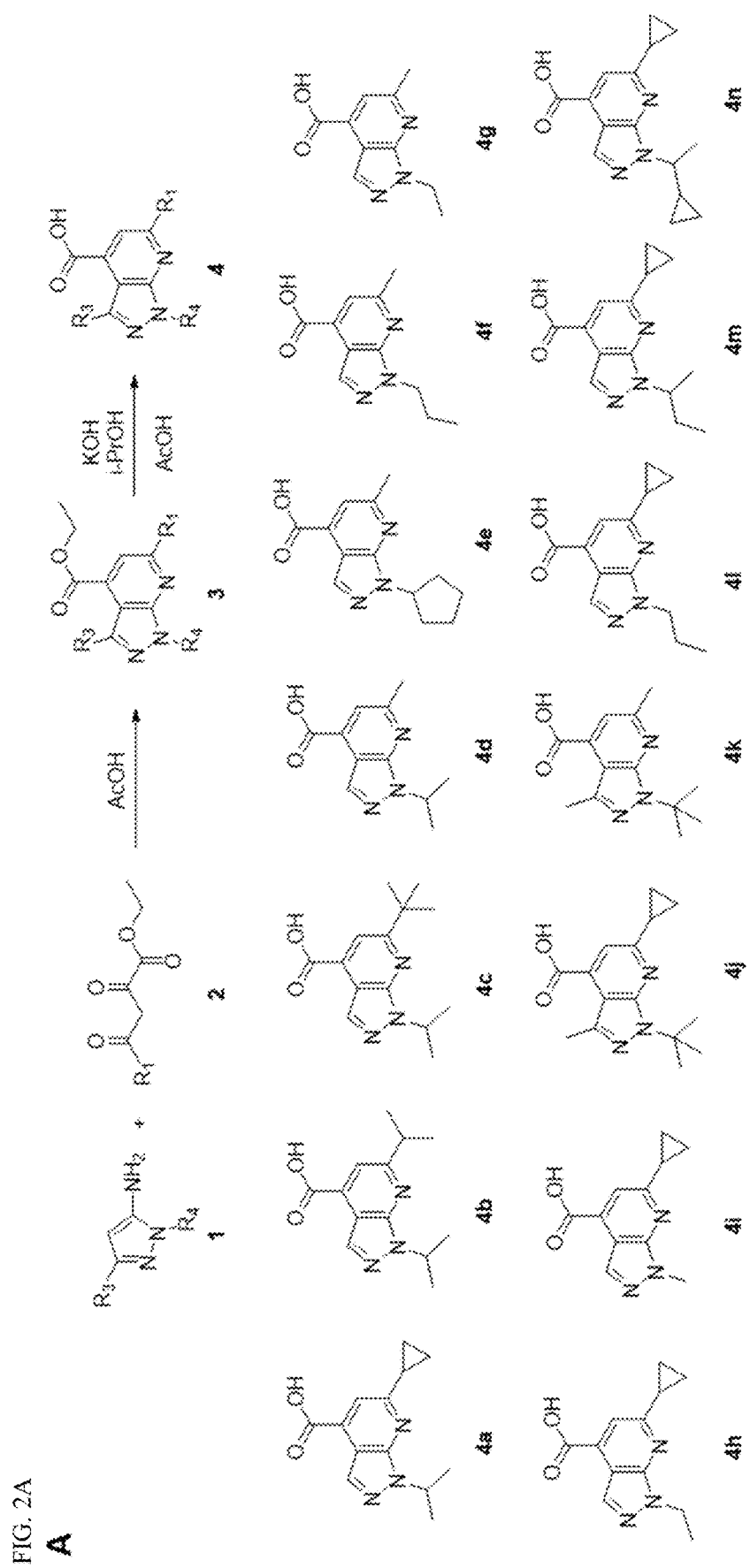
FIG. 2A-B shows synthesis of pyrazolopyridine analogs. (A) Synthesis of 1H-pyrazolo[3,4,-b]pyridine-4-carboxylic acid. (B) Representative synthesis of pyrazolopyridines with either tertiary amine (7g), secondary or primary amine (7k).
Figure 2B:
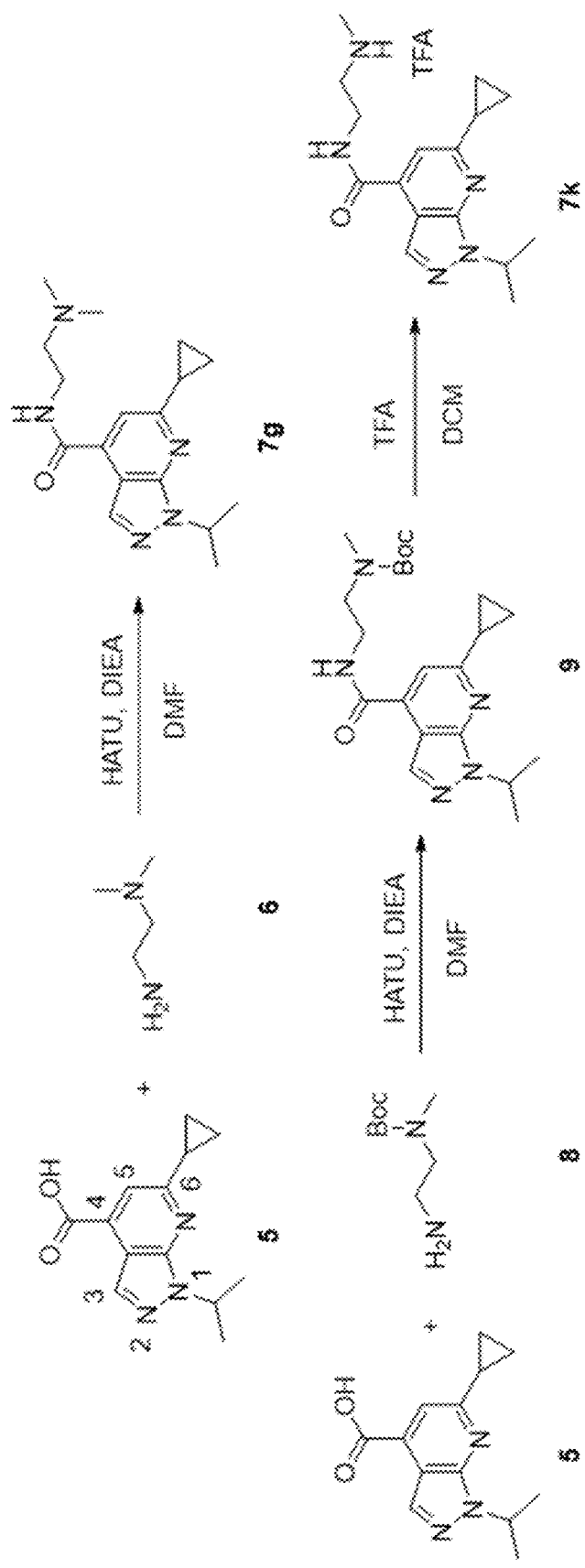

The synthesis of 1H-pyrazolo[3,4,-b]pyridine-4-carboxylic acid 4 followed the previously reported procedures (FIG. 2A).[26, 38] Briefly, condensation of 1-alkylpyrazole-5-amine or 1,3-dialkylpyrazole-5-amine 1 with the 4-alkyl-2,4-diketoester 2 in the presence of acetic acid gave the 1H-pyrazolo[3,4,-b]pyridine-4-carboxylic ester intermediate 3. Subsequent hydrolysis using potassium hydroxide in isopropanol gave the key intermediate 1H-pyrazolo[3,4,-b]pyridine-4-carboxylic acid 4. Next, for final compounds that contain tertiary amine (7g as an example), a one-step HATU-mediated amide coupling was used (FIG. 1B). For final compounds that contain either primary amine or secondary amine (7k as an example), a two-step process was applied: the first step was HATU-mediated amide coupling with the mono-Boc-protected diamine, and this was followed by TFA deprotection to give the final product (FIG. 2B).

Structure-Activity Relationship Studies

The initial hit compound 7a was identified as an EV-D68 antiviral through a CPE-based phenotypic screening of the Enamine compound library.[33, 34] It inhibited the contemporary EV-D68 US/KY/14-18953 strain with an $EC_{50}$ value of 16.7 μM and a selectivity index of 10.6 (Table 1). Gratifyingly, compound 7a also inhibited the closely related EV-A71 (Tainan/4643/1998) virus with an $EC_{50}$ value of 8.1 μM. To further optimize the antiviral potency, selectivity index, and spectrum of antiviral activity of 7a, we subsequently initiated a structure-activity relationship study. Specifically, we focused on diversifying the 1-alkyl $R_1$, 3-alkyl $R_3$, 4-amide $R_4$, and 6-alkyl $R_6$ substitutions on the 1H-pyrazolo[3,4,-b]pyridine core (FIG. 2B).

For the initial screening, all compounds were titrated to determine the antiviral efficacy and cellular cytotoxicity in viral CPE assay and neutral red uptake cell viability assay, respectively. Human rhabdomyosarcoma (RD) cells were used for EV-D68 and EV-A71 antiviral assays, and Vero cells were used for the CVB3 antiviral assay. For the CPE assay, virus-infected cells were treated with serial dilutions of compounds for 3 days, and cell viability were determined by neutral red uptake assay. For compound 7 series with 1-isopropyl and 6-cyclopropyl substitutions (7a-7m), it was found that the 4-position amide substitution had a profound effect on the antiviral activity and selectivity index (Table 1). Replacing the neutral ester in 7a with a positively charged pyrrolidine gave compound 7b, which had significantly improved antiviral efficacy. Compound 7c with diethylamine also had submicromolar $EC_{50}$ values against all three viruses. Changing diethylamine to dimethylamine gave compound 7d, which had increased selectivity index. Compound 7e with a shorter linker between the amide and the terminal amine was less active (7e vs 7d). Compound 7g with a cyclized liker was highly potent ($EC_{50}$=0.1 μM) but was less selective than 7f as shown by its low $CC_{50}$ values ($CC_{50}$=20.7 μM and 33.8 μM in RD and Vero cells, respectively). Compounds containing secondary or primary amine were equally potent as the compounds containing tertiary amine (7h, 7i vs 7d, and 7j vs 7f). Extending the linker between the amide and terminal amine from ethyl to propyl gave compounds 7k, 7l, and 7m, which had reduced antiviral activity compared with corresponding compounds with the ethyl linker (7k vs 7c, 7l vs 7d, 7m vs 7h). Overall, the most potent and selective compound from compound 7 series were 7d and 7h, which had more than 100-fold improvement in antiviral efficacy compared to the original hit 7a against EV-D68 virus.

For compound 10 series (10a-10f) with 6-isopropyl substitution, we selected the favorable amide substitutions from compound 7 series, and compounds 10a, 10c-10f turned out to have high antiviral potency and selectivity index ($EC_{50}$<1 μM and $SI_{50}$>120). Compounds 10b with a neutral terminal hydroxyl group had drastically reduced antiviral activity ($EC_{50}$=9.8 μM) against EV-D68, which is similar to antiviral activity of the screening hit 7a. These results suggest that the terminal positive charge is critical for the potent antiviral activity. The most potent and selective compound from this series was compound 10a. Compounds with 6-tert-butyl substitution 11a and 11b also had potent antiviral efficacy but the selectivity index was lower compared to compounds with 6-isopropyl substitution (11a vs 10a, and 11b vs 10e). Compounds with 6-methyl substitution 12a-12e, 13, 14, and 15a-15b were generally less active, except compound 12a. Next, the 1-position substitution was examined. Compound 16 with 1-ethyl substitution was less active than the analog 7d with 1-isopropyl substation. Nevertheless, the $EC_{50}$ values were still at the single-digit micromolar range across three different viruses. Compound 17 with 1-methyl substitution was less active, showing an $EC_{50}$ value of 9.8 μM against the EV-D68 virus. Compounds 18a and 18b with 1-tert-butyl and 3-methyl substitutions also had potent antiviral activity but with low $CC_{50}$ values. Compound 19 had similar antiviral activity as compound 18a against EV-D68 but had a higher selectivity index. Compound 20 with 1-propyl substitution, compound 21 with 1-isobutyl substitution, and compound 22 with 1-cyclopropylethyl substitution all had low single-digit or submicromolar $EC_{50}$ values against all three viruses, but their cellular cytotoxicity was higher than compound 7d, which had 1-isopropyl substitution.

TABLE 1

SAR study of pyrazolopyridine analogs against EV-D68, EV-A71 and CVB3.

| Structure | | Anti-EV-D68 US/KY/14-18953 in RD cells (μM) | Anti-EV-A71 Tainan/4643/1998 in RD cells (μM) | Anti-CVB3 in Vero cells (μM) |
|---|---|---|---|---|
| 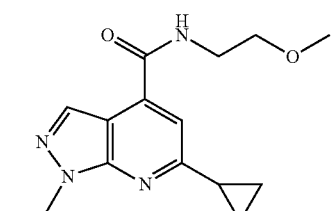 | 7a | $EC_{50}$ = 16.7 ± 3.8<br>$CC_{50}$ = 177.7 ± 11.5<br>$SI_{50}$ = 10.6 | $EC_{50}$ = 8.1 ± 0.7<br>$CC_{50}$ = 177.7 ± 115.5<br>$SI_{50}$ = 21.9 | N.T. |
| 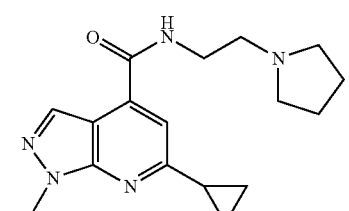 | 7b | $EC_{50}$ = 0.1 ± 0.1<br>$CC_{50}$ = 46.5 ± 3.0<br>$SI_{50}$ = 465.0 | $EC_{50}$ = 0.2 ± 0.1<br>$CC_{50}$ = 46.5 ± 3.0<br>$SI_{50}$ = 232.5 | $EC_{50}$ = 0.2 ± 0.1<br>$CC_{50}$ = 63.1 ± 8.4<br>$SI_{50}$ = 315.5 |

TABLE 1-continued

SAR study of pyrazolopyridine analogs against EV-D68, EV-A71 and CVB3.

| Structure | | Anti-EV-D68 US/KY/14-18953 in RD cells (μM) | Anti-EV-A71 Tainan/4643/1998 in RD cells (μM) | Anti-CVB3 in Vero cells (μM) |
|---|---|---|---|---|
| *(structure)* | 7c | $EC_{50}$ = 0.4 ± 0.2<br>$CC_{50}$ = 89.9 ± 10.8<br>$SI_{50}$ = 224.8 | $EC_{50}$ = 0.3 ± 0.2<br>$CC_{50}$ = 89.9<br>$SI_{50}$ = 299.7 | $EC_{50}$ = 0.5 ± 0.1<br>$CC_{50}$ = 53.6 ± 9.3<br>$SI_{50}$ = 107.2 |
| *(structure)* | 7d | $EC_{50}$ = 0.1 ± 0.0<br>$CC_{50}$ = 200.2 ± 10.8<br>$SI_{50}$ = 2000.0 | $EC_{50}$ = 0.8 ± 0.2<br>$CC_{50}$ = 200.0 ± 10.8<br>$SI_{50}$ = 250.0 | $EC_{50}$ = 0.2 ± 0.1<br>$CC_{50}$ = 125.3 ± 18.5<br>$SI_{50}$ = 626.5 |
| *(structure)* | 7e | $EC_{50}$ = 1.4 ± 0.1<br>$CC_{50}$ = 91.6 ± 22.1<br>$SI_{50}$ = 65.4 | N.T. | N.T. |
| *(structure)* | 7f | $EC_{50}$ = 0.1 ± 0.2<br>$CC_{50}$ = 72.6 ± 11.3<br>$SI_{50}$ = 726.0 | $EC_{50}$ = 0.1 ± 0.0<br>$CC_{50}$ = 72.6 ± 11.3<br>$SI_{50}$ = 726.0 | $EC_{50}$ = 0.04 ± 0.00<br>$CC_{50}$ >300.0<br>$SI_{50}$ >7500.0 |
| *(structure)* | 7g | $EC_{50}$ = 0.1 ± 0.2<br>$CC_{50}$ = 20.7 ± 1.9<br>$SI_{50}$ = 207.0 | $EC_{50}$ = 0.1 ± 0.1<br>$CC_{50}$ = 20.7 ± 1.9<br>$SI_{50}$ = 207.0 | $EC_{50}$ = 0.1 ± 0.0<br>$CC_{50}$ = 33.8 ± 2.2<br>$SI_{50}$ = 338.0 |
| *(structure)* | 7h | $EC_{50}$ = 0.2 ± 0.1<br>$CC_{50}$ = 236.3 ± 20.5<br>$SI_{50}$ = 1183.0 | $EC_{50}$ = 0.2 ± 0.1<br>$CC_{50}$ = 236.3 ± 20.5<br>$SI_{50}$ = 1183.0 | $EC_{50}$ = 0.2 ± 0.2<br>$CC_{50}$ >100.0<br>$SI_{50}$ >500.0 |

TABLE 1-continued

SAR study of pyrazolopyridine analogs against EV-D68, EV-A71 and CVB3.

| Structure | | Anti-EV-D68 US/KY/14-18953 in RD cells (μM) | Anti-EV-A71 Tainan/4643/1998 in RD cells (μM) | Anti-CVB3 in Vero cells (μM) |
|---|---|---|---|---|
| 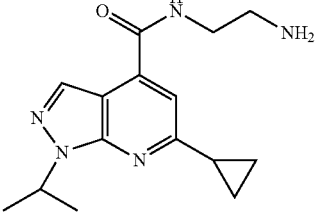 | 7i | $EC_{50} = 0.4 \pm 0.2$<br>$CC_{50} = 259.3 \pm 11.3$<br>$SI_{50} = 648.3$ | $EC_{50} = 0.4 \pm 0.1$<br>$CC_{50} = 259.3 \pm 11.3$<br>$SI_{50} = 648.3$ | $EC_{50} = 0.9 \pm 0.2$<br>$CC_{50} = 173.8 \pm 11.3$<br>$SI_{50} = 193.1$ |
| 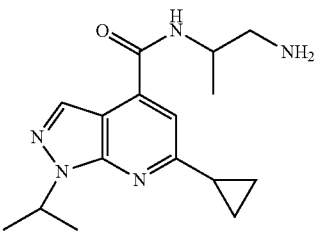 [SMILES: CC(CN)NC(=O)c1cc(C2CC2)nc2c1cnn2C(C)C] | 7j | $EC_{50} = 0.3 \pm 0.1$<br>$CC_{50} = 112.9 \pm 8.7$<br>$SI_{50} = 376.3$ | $EC_{50} = 0.6 \pm 0.1$<br>$CC_{50} = 112.9 \pm 8.7$<br>$SI_{50} = 188.2$ | $EC_{50} = 0.3 \pm 0.1$<br>$CC_{50} = 164.2 \pm 8.2$<br>$SI_{50} = 547.3$ |
| 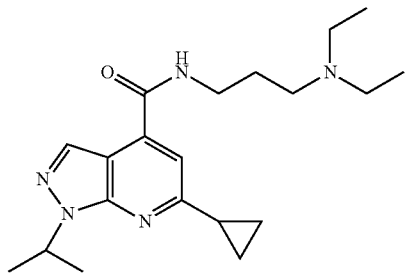 [SMILES: CCN(CC)CCCNC(=O)c1cc(C2CC2)nc2c1cnn2C(C)C] | 7k | $EC_{50} = 1.9 \pm 0.2$<br>$CC_{50} = 43.8 \pm 1.3$<br>$SI_{50} = 23.1$ | $EC_{50} = 6.1 \pm 0.5$<br>$CC_{50} = 43.8 \pm 1.3$<br>$SI_{50} = 7.2$ | $EC_{50} = 1.7 \pm 0.3$<br>$CC_{50} = 130.2 \pm 6.4$<br>$SI_{50} = 76.6$ |
| 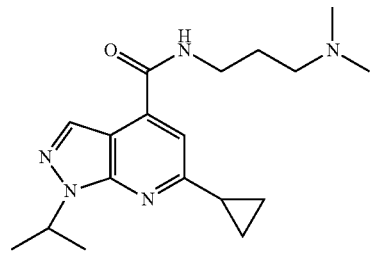 [SMILES: CC(C)n1ncc2c(C(=O)NCCCN(C)C)cc(C3CC3)nc21] | 7l | $EC_{50} = 1.2 \pm 0.3$<br>$CC_{50} = 74.1 \pm 2.5$<br>$SI_{50} = 61.8$ | $EC_{50} = 1.8 \pm 0.4$<br>$CC_{50} = 74.1 \pm 2.5$<br>$SI_{50} = 41.2$ | $EC_{50} = 0.4 \pm 0.2$<br>$CC_{50} > 200$<br>$SI_{50} > 500$ |
| 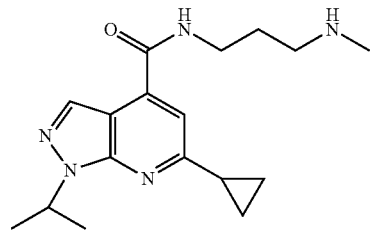 [SMILES: CNCCCNC(=O)c1cc(C2CC2)nc2c1cnn2C(C)C] | 7m | $EC_{50} = 1.7 \pm 0.2$<br>$CC_{50} = 183.0 \pm 20.1$<br>$SI_{50} = 107.6$ | $EC_{50} = 5.3 \pm 0.2$<br>$CC_{50} = 183.0 \pm 20.1$<br>$SI_{50} = 34.5$ | $EC_{50} = 1.6 \pm 0.3$<br>$CC_{50} = 281.3$<br>$SI_{50} = 175.8$ |
| 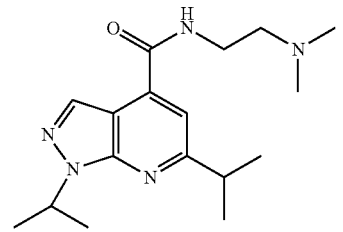 [SMILES: CC(C)c1cc(C(=O)NCCN(C)C)c2cnn(C(C)C)c2n1] | 10a | $EC_{50} = 0.1 \pm 0.2$<br>$CC_{50} = 160.9 \pm 12.8$<br>$SI_{50} = 1609.0$ | $EC_{50} = 0.1 \pm 0.0$<br>$CC_{50} = 160.9 \pm 12.8$<br>$SI_{50} = 1609.0$ | $EC_{50} = 0.04 \pm 0.02$<br>$CC_{50} > 300.0$<br>$SI_{50} > 7500.0$ |

TABLE 1-continued

SAR study of pyrazolopyridine analogs against EV-D68, EV-A71 and CVB3.

| Structure | | Anti-EV-D68 US/KY/14-18953 in RD cells (μM) | Anti-EV-A71 Tainan/4643/1998 in RD cells (μM) | Anti-CVB3 in Vero cells (μM) |
|---|---|---|---|---|
| [Structure: pyrazolopyridine with N-(2-hydroxyethyl)carboxamide, isopropyl] | 10b | $EC_{50}$ = 9.8 ± 2.3<br>$CC_{50}$ >100.0<br>$SI_{50}$ >10.2 | N.T. | N.T. |
| [Structure: pyrazolopyridine with N-(1-methyl-2-(dimethylamino)ethyl)carboxamide, isopropyl] | 10c | $EC_{50}$ = 0.1 ± 0.0<br>$CC_{50}$ >100.0<br>$SI_{50}$ >1000.0 | $EC_{50}$ = 1.0 ± 0.4<br>$CC_{50}$ = 70.3 ± 1.9<br>$SI_{50}$ = 703.0 | $EC_{50}$ = 0.1 ± 0.2<br>$CC_{50}$ = 116.6 ± 27.8<br>$SI_{50}$ = 1166.0 |
| [Structure: pyrazolopyridine with N-(2-(methylamino)ethyl)carboxamide, isopropyl] | 10d | $EC_{50}$ = 0.4 ± 0.2<br>$CC_{50}$ >100.0<br>$SI_{50}$ >250.0 | $EC_{50}$ = 0.1 ± 0.0<br>$CC_{50}$ >100.0<br>$SI_{50}$ >1000.0 | $EC_{50}$ = 0.3 ± 0.1<br>$CC_{50}$ = 132.9 ± 27.9<br>$SI_{50}$ = 443.0 |
| [Structure: pyrazolopyridine with N-(2-aminoethyl)carboxamide, isopropyl] | 10e | $EC_{50}$ = 0.6 ± 0.2<br>$CC_{50}$ = 169.5 ± 8.6<br>$SI_{50}$ = 282.5 | $EC_{50}$ = 0.6 ± 0.2<br>$CC_{50}$ = 169.5 ± 8.6<br>$SI_{50}$ = 282.5 | $EC_{50}$ = 0.9 ± 0.1<br>$CC_{50}$ = 108.1 ± 22.7<br>$SI_{50}$ = 120.1 |
| [Structure: pyrazolopyridine with N-(1-methyl-2-aminoethyl)carboxamide, isopropyl] | 10f | $EC_{50}$ = 0.4 ± 0.3<br>$CC_{50}$ = 118.1 ± 15.4<br>$SI_{50}$ = 295.3 | $EC_{50}$ = 0.5 ± 0.3<br>$CC_{50}$ = 118.1 ± 15.4<br>$SI_{50}$ = 236.2 | $EC_{50}$ = 0.6 ± 0.3<br>$CC_{50}$ = 134.8 ± 5.9<br>$SI_{50}$ = 224.7 |
| [Structure: pyrazolopyridine with N-(2-(dimethylamino)ethyl)carboxamide, tert-butyl] | 11a | $EC_{50}$ = 0.1 ± 0.0<br>$CC_{50}$ = 31.4 ± 7.1<br>$SI_{50}$ = 314.0 | $EC_{50}$ = 0.04 ± 0.00<br>$CC_{50}$ = 31.4 ± 7.1<br>$SI_{50}$ = 785.0 | $EC_{50}$ = 0.1 ± 0.2<br>$CC_{50}$ = 34.4 ± 2.2<br>$SI_{50}$ = 344.0 |

TABLE 1-continued

SAR study of pyrazolopyridine analogs against EV-D68, EV-A71 and CVB3.

| Structure | | Anti-EV-D68 US/KY/14-18953 in RD cells (μM) | Anti-EV-A71 Tainan/4643/1998 in RD cells (μM) | Anti-CVB3 in Vero cells (μM) |
|---|---|---|---|---|
| 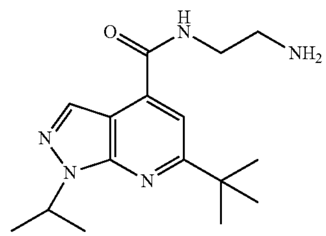 [SMILES: CC(C)n1ncc2c(C(=O)NCCN)cc(C(C)(C)C)nc21] | 11b | $EC_{50}$ = 0.1 ± 0.1<br>$CC_{50}$ = 24.6 ± 3.1<br>$SI_{50}$ = 246.0 | $EC_{50}$ = 0.2 ± 0.1<br>$CC_{50}$ = 24.6 ± 3.1<br>$SI_{50}$ = 123.0 | $EC_{50}$ = 0.1 ± 0.2<br>$CC_{50}$ = 23.0 ± 1.5<br>$SI_{50}$ = 230.0 |
| 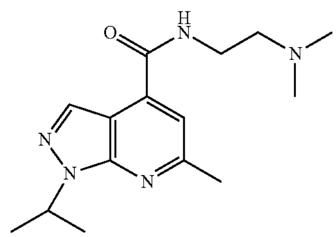 [SMILES: Cc1cc(C(=O)NCCN(C)C)c2cnn(C(C)C)c2n1] | 12a | $EC_{50}$ = 0.4 ± 0.2<br>$CC_{50}$ = 112.3 ± 19.6<br>$SI_{50}$ = 280.8 | $EC_{50}$ = 0.1 ± 0.0<br>$CC_{50}$ = 112.3 ± 19.6<br>$SI_{50}$ = 1123.0 | $EC_{50}$ = 0.2 ± 0.0<br>$CC_{50}$ >300.0<br>$SI_{50}$ >1500.0 |
| 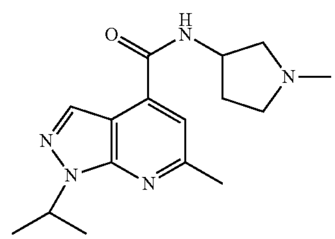 [SMILES: Cc1cc(C(=O)NC2CCN(C)C2)c2cnn(C(C)C)c2n1] | 12b | $EC_{50}$ = 1.8 ± 0.2<br>$CC_{50}$ >300.0<br>$SI_{50}$ >166.7 | $EC_{50}$ = 0.5 ± 0.3<br>$CC_{50}$ >300.0<br>$SI_{50}$ >600.0 | $EC_{50}$ = 0.8 ± 0.2<br>$CC_{50}$ >300.0<br>$SI_{50}$ >375.0 |
| 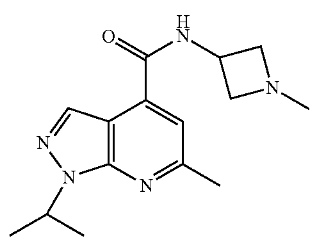 [SMILES: Cc1cc(C(=O)NC2CN(C)C2)c2cnn(C(C)C)c2n1] | 12c | $EC_{50}$ = 11.3 ± 1.6<br>$CC_{50}$ >300.0<br>$SI_{50}$ >26.5 | $EC_{50}$ = 7.3 ± 0.3<br>$CC_{50}$ >300.0<br>$SI_{50}$ >41.1 | $EC_{50}$ = 3.8 ± 1.2<br>$CC_{50}$ >300.0<br>$SI_{50}$ >78.9 |
| 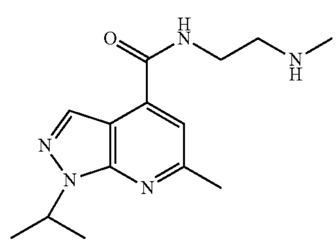 [SMILES: CNCCNC(=O)c1cc(C)nc2c1cnn2C(C)C] | 12d | $EC_{50}$ = 2.3 ± 0.2<br>$CC_{50}$ >300.0<br>$SI_{50}$ >130.4 | $EC_{50}$ = 0.5 ± 0.1<br>$CC_{50}$ >300.0<br>$SI_{50}$ >600.0 | $EC_{50}$ = 1.4 ± 0.4<br>$CC_{50}$ >300.0<br>$SI_{50}$ >214.3 |
| 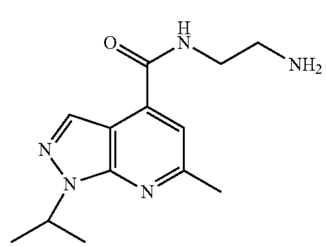 [SMILES: Cc1cc(C(=O)NCCN)c2cnn(C(C)C)c2n1] | 12e | $EC_{50}$ = 4.7 ± 0.6<br>$CC_{50}$ >300.0<br>$SI_{50}$ >63.8 | $EC_{50}$ = 0.7 ± 0.1<br>$CC_{50}$ >300.0<br>$SI_{50}$ >428.6 | $EC_{50}$ = 3.8 ± 2.4<br>$CC_{50}$ >300.0<br>$SI_{50}$ >78.9 |

TABLE 1-continued

SAR study of pyrazolopyridine analogs against EV-D68, EV-A71 and CVB3.

| Structure | | Anti-EV-D68 US/KY/14-18953 in RD cells (μM) | Anti-EV-A71 Tainan/4643/1998 in RD cells (μM) | Anti-CVB3 in Vero cells (μM) |
|---|---|---|---|---|
| 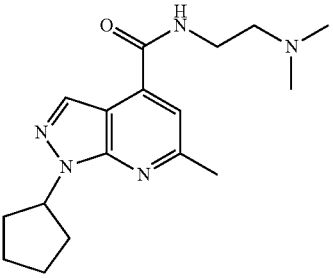 [SMILES: Cc1cc(C(=O)NCCN(C)C)c2cnn(C3CCCC3)c2n1] | 13 | $EC_{50}$ = 11.1 ± 0.3<br>$CC_{50}$ = 88.4 ± 18.5<br>$SI_{50}$ = 8.0 | N.T. | N.T. |
| 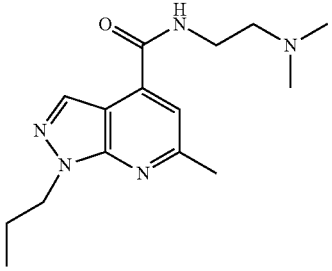 [SMILES: CCCn1ncc2c(C(=O)NCCN(C)C)cc(C)nc21] | 14 | $EC_{50}$ = 48.4 ± 2.2<br>$CC_{50}$ = 218.6 ± 25.3<br>$SI_{50}$ = 4.5 | N.T. | N.T. |
| 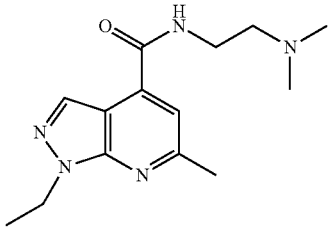 [SMILES: CCn1ncc2c(C(=O)NCCN(C)C)cc(C)nc21] | 15a | $EC_{50}$ = 18.3 ± 0.5<br>$CC_{50}$ >300<br>$SI_{50}$ >16.4 | N.T. | N.T. |
| 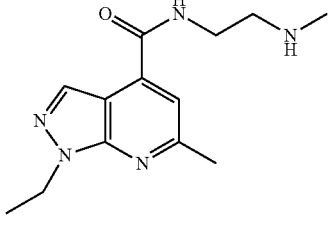 | 15b | $EC_{50}$ = 58.4 ± 1.9<br>$CC_{50}$ >300<br>$SI_{50}$ >5.1 | $EC_{50}$ >20 μM | N.T. |
| 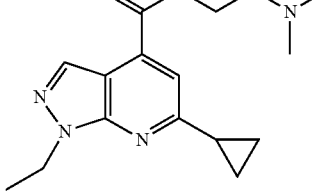 | 16 | $EC_{50}$ = 1.7 ± 0.2<br>$CC_{50}$ = 263.2 ± 21.1<br>$SI_{50}$ = 154.8 | $EC_{50}$ = 1.2 ± 0.3<br>$CC_{50}$ = 263.2 ± 21.1<br>$SI_{50}$ = 219.3 | $EC_{50}$ = 1.8 ± 0.4<br>$CC_{50}$ >300<br>$SI_{50}$ >166.7 |
| 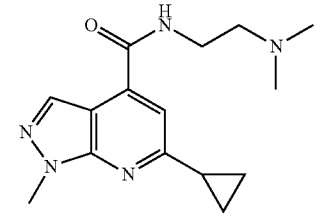 [SMILES: CN(C)CCNC(=O)c1cc(C2CC2)nc2c1cnn2C] | 17 | $EC_{50}$ = 9.8 ± 1.5<br>$CC_{50}$ >300<br>$SI_{50}$ >30.6 | N.T. | N.T. |

TABLE 1-continued

SAR study of pyrazolopyridine analogs against EV-D68, EV-A71 and CVB3.

| Structure | | Anti-EV-D68 US/KY/14-18953 in RD cells (μM) | Anti-EV-A71 Tainan/4643/1998 in RD cells (μM) | Anti-CVB3 in Vero cells (μM) |
|---|---|---|---|---|
| 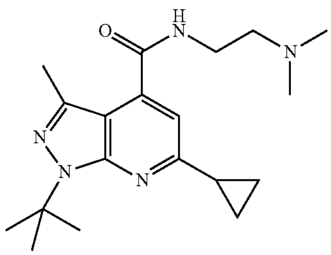 [SMILES: Cc1nn(C(C)(C)C)c2nc(C3CC3)cc(C(=O)NCCN(C)C)c12] | 18a | $EC_{50} = 0.8 \pm 0.2$<br>$CC_{50} = 45.2 \pm 27.6$<br>$SI_{50} = 56.5$ | $EC_{50} = 3.5 \pm 1.2$<br>$CC_{50} = 45.2 \pm 27.6$<br>$SI_{50} = 12.9$ | $EC_{50} = 1.8 \pm 0.4$<br>$CC_{50} = 56.3 \pm 11.2$<br>$SI_{50} = 31.3$ |
| 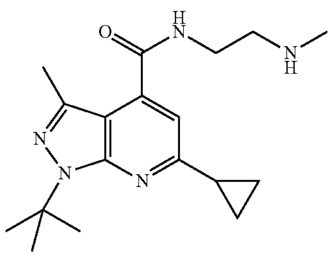 [SMILES: CNCCNC(=O)c1cc(C2CC2)nc2c1c(C)nn2C(C)(C)C] | 18b | $EC_{50} = 1.1 \pm 0.5$<br>$CC_{50} = 31.9 \pm 8.2$<br>$SI_{50} = 29.0$ | $EC_{50} = 8.4 \pm 0.2$<br>$CC_{50} = 31.9 \pm 8.2$<br>$SI_{50} = 3.8$ | $EC_{50} = 2.9 \pm 0.3$<br>$CC_{50} = 36.8 \pm 17.8$<br>$SI_{50} = 12.7$ |
| 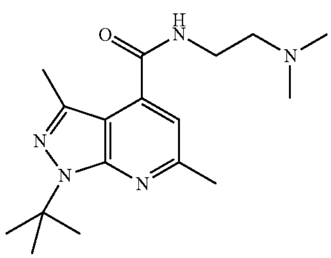 [SMILES: Cc1cc(C(=O)NCCN(C)C)c2c(C)nn(C(C)(C)C)c2n1] | 19 | $EC_{50} = 1.0 \pm 0.1$<br>$CC_{50} = 116.6 \pm 16.1$<br>$SI_{50} = 116.6$ | $EC_{50} = 7.4 \pm 1.7$<br>$CC_{50} = 116.6 \pm 16.1$<br>$SI_{50} = 15.8$ | $EC_{50} = 2.1 \pm 0.9$<br>$CC_{50} = 184.0 \pm 13.2$<br>$SI_{50} = 88.9$ |
| 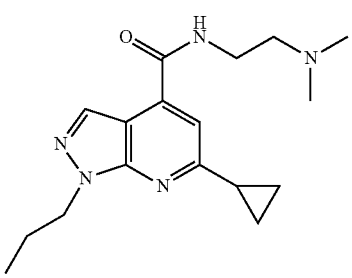 [SMILES: CCCn1ncc2c(C(=O)NCCN(C)C)cc(C3CC3)nc21] | 20 | $EC_{50} = 1.2 \pm 0.2$<br>$CC_{50} = 57.7 \pm 10.1$<br>$SI_{50} = 48.1$ | $EC_{50} = 2.0 \pm 0.6$<br>$CC_{50} = 57.7 \pm 10.1$<br>$SI_{50} = 28.9$ | $EC_{50} = 2.0 \pm 0.3$<br>$CC_{50} = 111.0 \pm 6.8$<br>$SI_{50} = 55.5$ |
| 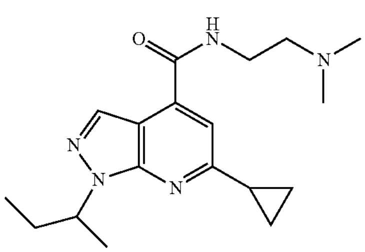 [SMILES: CCC(C)n1ncc2c(C(=O)NCCN(C)C)cc(C3CC3)nc21] | 21 | $EC_{50} = 0.2 \pm 0.1$<br>$CC_{50} = 40.7 \pm 2.8$<br>$SI_{50} = 203.5$ | $EC_{50} = 0.1 \pm 0.0$<br>$CC_{50} = 40.7 \pm 2.8$<br>$SI_{50} = 407.0$ | $EC_{50} = 0.1 \pm 0.0$<br>$CC_{50} = 101.4 \pm 13.6$<br>$SI_{50} = 1014.0$ |

TABLE 1-continued

SAR study of pyrazolopyridine analogs against EV-D68, EV-A71 and CVB3.

| Structure | | Anti-EV-D68 US/KY/14-18953 in RD cells (μM) | Anti-EV-A71 Tainan/4643/1998 in RD cells (μM) | Anti-CVB3 in Vero cells (μM) |
|---|---|---|---|---|
| [structure image] | 22 | $EC_{50} = 0.7 \pm 0.2$<br>$CC_{50} = 28.4 \pm 2.3$<br>$SI_{50} = 40.6$ | $EC_{50} = 0.2 \pm 0.1$<br>$CC_{50} = 28.4 \pm 2.3$<br>$SI_{50} = 142.0$ | $EC_{50} = 1.9 \pm 0.4$<br>$CC_{50} = 51.7 \pm 8.3$<br>$SI_{50} = 27.2$ |

[a]Antiviral efficacy was determined in the CPE assay with EV-D68 US/KY/14-18953 virus and EV-A71 Tainan/4643/1998 virus in RD cells. For antiviral assay with CVB3 virus Vero cells were used.
[b]Cytotoxicity was determined using the neutral red uptake method.
[c]N.T. = not tested. The results are the mean ± standard deviation of three repeats. SI = selectivity index ($CC_{50}/EC_{50}$).

Summary of Structure-Activity Relationship

Figure 3:
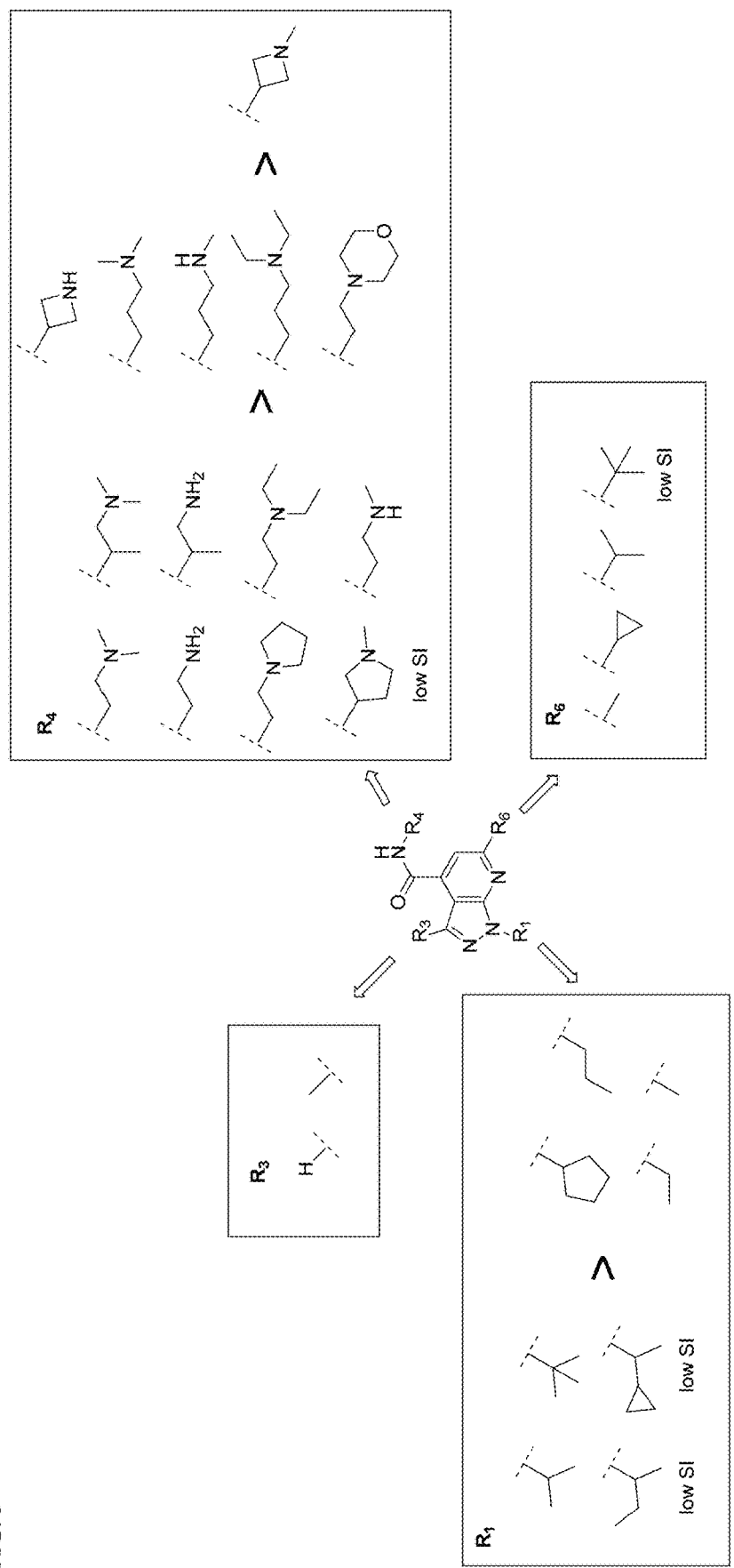
FIG. 3 shows a summary of structure activity relationship (SAR) studies of pyrazolopyridine.

The summary of the SAR results was shown in FIG. 3. For position 1 substitution, branched alkyl substitutions such as isopropyl, tert-butyl, isobutyl, and 1-cyclopropylethyl were favored over methyl, ethyl, propyl, and cyclopentyl, and compounds with 1-isobutyl and 1-(1-cyclopropylehtyl) substitution had a lower selectivity index. For position 3 substitution, both methyl and hydrogen were tolerated. For the 4-position amide, the ethyl linker was preferred over the propyl linker. The terminal amine could be tertiary, secondary or primary amine. For the 6-position substitution, both small and bulky alkyl substitutions were tolerated, and tert-butyl substitution led to lower selectivity index.

Broad-Spectrum Antiviral Activity

Encouraged by the potent and broad-spectrum antiviral activity of these pyrazolopyridine analogs, we selected four lead candidates 7d, 7h, 10a, and 19 with the highest potency and selectivity index from the primary screening, and tested their antiviral activity against several other contemporary EV-D68 and EV-A71 strains (Table 2). The EV-D68 strains selected were from the 2014 outbreak and have been linked with AFM.[11] Compound 7d is the most potent lead compound with $EC_{50}$ values ranging from 0.04 to 0.1 μM against all EV-D68 and EV-A71 strains tested as well as a high selectivity index of over 2000. Compounds 7h and 10a had similar antiviral activity against different strains of EV-D68 and EV-A71 with $EC_{50}$ values ranging from 0.06 to 0.3 μM and a selectivity index of over 700. Compound 19 was less active compared to 7d, 7h, and 10a, but it remains a potent inhibitor with broad-acting activity against all strains tested ($EC_{50}$=0.4 to 7.4 μM; $SI_{50}$>100). Overall, consistent antiviral efficacy was observed across different strains of EV-D68 and EV-A71, suggesting these pyrazolopyridine compounds might target a conserved viral protein among enteroviruses or a common host signaling pathway that is essential for the viral replication.

TABLE 2

Antiviral activity of potent leads against different serotypes of EV-D68 and EV-A71 in RD cells

| EV-strains | | 7d (μM) | 7h (μM) | 10a (μM) | 19 (μM) |
|---|---|---|---|---|---|
| EV-D68 | US/KY/14-18953 (Clade D) | $EC_{50} = 0.1 \pm 0.2$<br>$CC_{50} = 200.0 \pm 10.8$<br>$SI_{50} = 2000$ | $EC_{50} = 0.2 \pm 0.1$<br>$CC_{50} = 236.3 \pm 20.5$<br>$SI_{50} = 1183$ | $EC_{50} = 0.1 \pm 0.2$<br>$CC_{50} = 160.9 \pm 12.8$<br>$SI_{50} = 1609$ | $EC_{50} = 1.0 \pm 0.1$<br>$CC_{50} = 116.6 \pm 16.1$<br>$SI_{50} = 116.6$ |
| | US/MO/14-18947 (Clade B1) | $EC_{50} = 0.1 \pm 0.0$<br>$CC_{50} = 200.0 \pm 10.8$<br>$SI_{50} = 2000$ | $EC_{50} = 0.2 \pm 0.2$<br>$CC_{50} = 236.3 \pm 20.5$<br>$SI_{50} = 1183$ | $EC_{50} = 0.07 \pm 0.01$<br>$CC_{50} = 160.9 \pm 12.8$<br>$SI_{50} = 2298.6$ | $EC_{50} = 0.4 \pm 0.2$<br>$CC_{50} = 116.6 \pm 16.1$<br>$SI_{50} = 291.5$ |
| | US/MO/14-18949 (Clade B1) | $EC_{50} = 0.1 \pm 0.0$<br>$CC_{50} = 200.0 \pm 10.8$<br>$SI_{50} = 2000$ | $EC_{50} = 0.2 \pm 0.1$<br>$CC_{50} = 236.3 \pm 20.5$<br>$SI_{50} = 1183$ | $EC_{50} = 0.08 \pm 0.01$<br>$CC_{50} = 160.9 \pm 12.8$<br>$SI_{50} = 2011.3$ | $EC_{50} = 0.7 \pm 0.4$<br>$CC_{50} = 116.6 \pm 16.1$<br>$SI_{50} = 166.6$ |
| | US/IL/14-18956 (Clade B2) | $EC_{50} = 0.04 \pm 0.01$<br>$CC_{50} = 200.0 \pm 10.8$<br>$SI_{50} = 5000$ | $EC_{50} = 0.2 \pm 0.0$<br>$CC_{50} = 236.3 \pm 20.5$<br>$SI_{50} = 1183$ | $EC_{50} = 0.07 \pm 0.01$<br>$CC_{50} = 160.9 \pm 12.8$<br>$SI_{50} = 2298.6$ | $EC_{50} = 0.4 \pm 0.1$<br>$CC_{50} = 116.6 \pm 16.1$<br>$SI_{50} = 291.5$ |

TABLE 2-continued

Antiviral activity of potent leads against different serotypes of EV-D68 and EV-A71 in RD cells

| EV-strains | | 7d (μM) | 7h (μM) | 10a (μM) | 19 (μM) |
|---|---|---|---|---|---|
| EV-A71 | US/IL/14-18952 (Clade B2) | $EC_{50}$ = 0.04 ± 0.01<br>$CC_{50}$ = 200.0 ± 10.8<br>$SI_{50}$ = 5000 | $EC_{50}$ = 0.2 ± 0.0<br>$CC_{50}$ = 236.3 ± 20.5<br>$SI_{50}$ = 1183 | $EC_{50}$ = 0.09 ± 0.01<br>$CC_{50}$ = 160.9 ± 12.8<br>$SI_{50}$ = 1787.8 | $EC_{50}$ = 0.7 ± 0.0<br>$CC_{50}$ = 116.6 ± 16.1<br>$SI_{50}$ = 166.6 |
| | Tainan/4643/1998 | $EC_{50}$ = 0.1 ± 0.0<br>$CC_{50}$ = 200.0 ± 10.8<br>$SI_{50}$ = 2000 | $EC_{50}$ = 0.2 ± 0.0<br>$CC_{50}$ = 236.3 ± 20.5<br>$SI_{50}$ = 1183 | $EC_{50}$ = 0.2 ± 04<br>$CC_{50}$ = 160.9 ± 12.8<br>$SI_{50}$ = 804.5 | $EC_{50}$ = 7.4 ± 1.7<br>$CC_{50}$ = 236.3 ± 20.5<br>$SI_{50}$ = 31.9 |
| | USA/CT/2016-19519 | $EC_{50}$ = 0.06 ± 0.01<br>$CC_{50}$ = 200.0 ± 10.8<br>$SI_{50}$ = 3333.3 | $EC_{50}$ = 0.1 ± 0.0<br>$CC_{50}$ = 236.3 ± 20.5<br>$SI_{50}$ = 2363 | $EC_{50}$ = 0.06 ± 0.01<br>$CC_{50}$ = 160.9 ± 12.8<br>$SI_{50}$ = 2681.7 | $EC_{50}$ = 1.3 ± 0.4<br>$CC_{50}$ = 236.3 ± 20.5<br>$SI_{50}$ = 181.8 |
| | A71 MP4 | $EC_{50}$ = 0.1 ± 0.0<br>$CC_{50}$ = 200.0 ± 10.8<br>$SI_{50}$ = 2000 | $EC_{50}$ = 0.3 ± 0.0<br>$CC_{50}$ = 236.3 ± 20.5<br>$SI_{50}$ = 787.7 | $EC_{50}$ = 0.2 ± 0.0<br>$CC_{50}$ = 160.9 ± 12.8<br>$SI_{50}$ = 804.5 | $EC_{50}$ = 2.0 ± 0.3<br>$CC_{50}$ = 236.3 ± 20.5<br>$SI_{50}$ = 118.2 |

[a]Antiviral efficacy $EC_{50}$ was determined using the CPE assay in RD cells.
[b]Cytotoxicity $CC_{50}$ was determined using the neutral red uptake method.
[c]N.T. = not tested. The results are the mean ± standard deviation of three repeats. $SI_{50}$ = selectivity index ($CC_{50}/EC_{50}$).

Antiviral Activity in Secondary Plaque Assay

Figure 4:
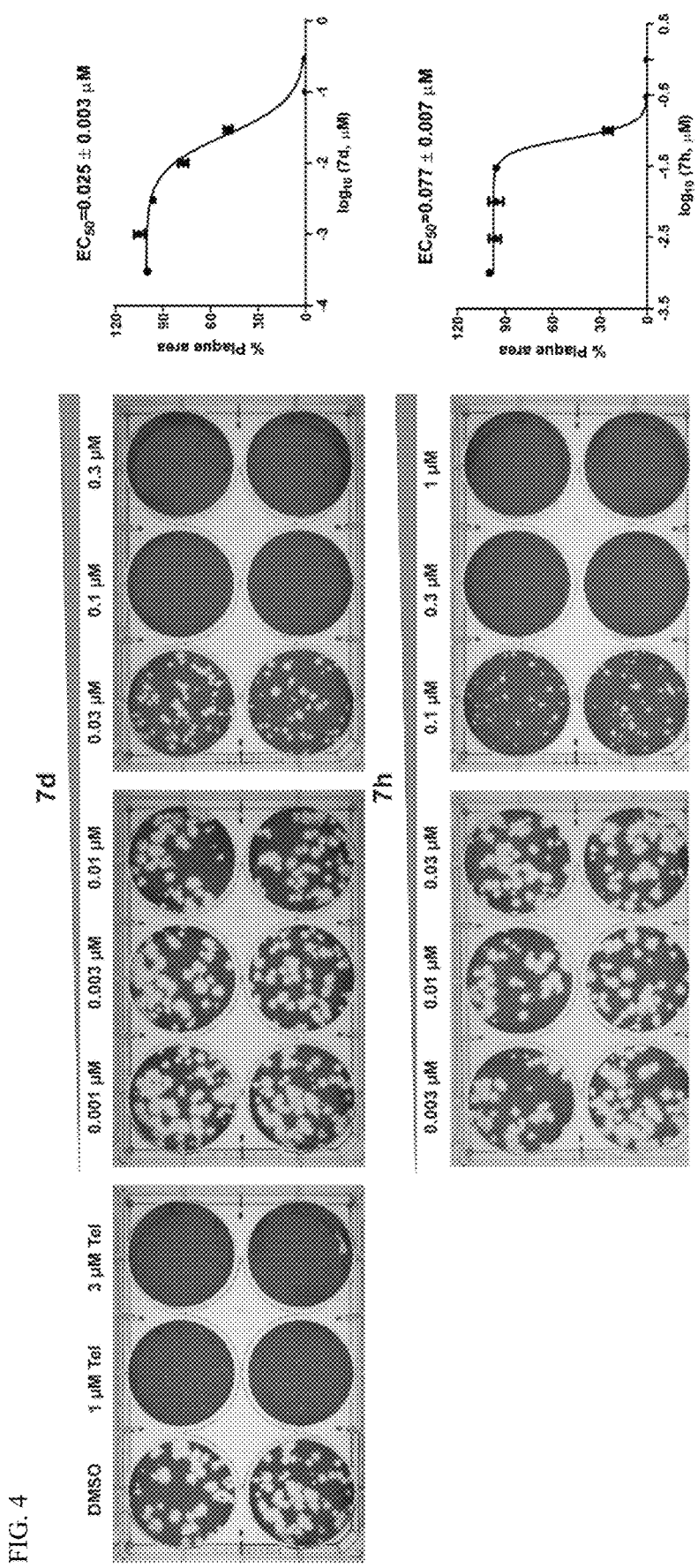
FIG. 4 shows antiviral activity of compounds 7d, 7h, 10a, and 19 against EV-D68 US/MO/14-18947 in plaque assay. The plaque areas were quantified in Image J and $EC_{50}$ values were determined through curve fittings in Graphpad Prism 8 using log(concentration of inhibitors) vs percentage of plaque area with variable slopes. The results are the mean±standard deviation of two repeats.
Figure 4:
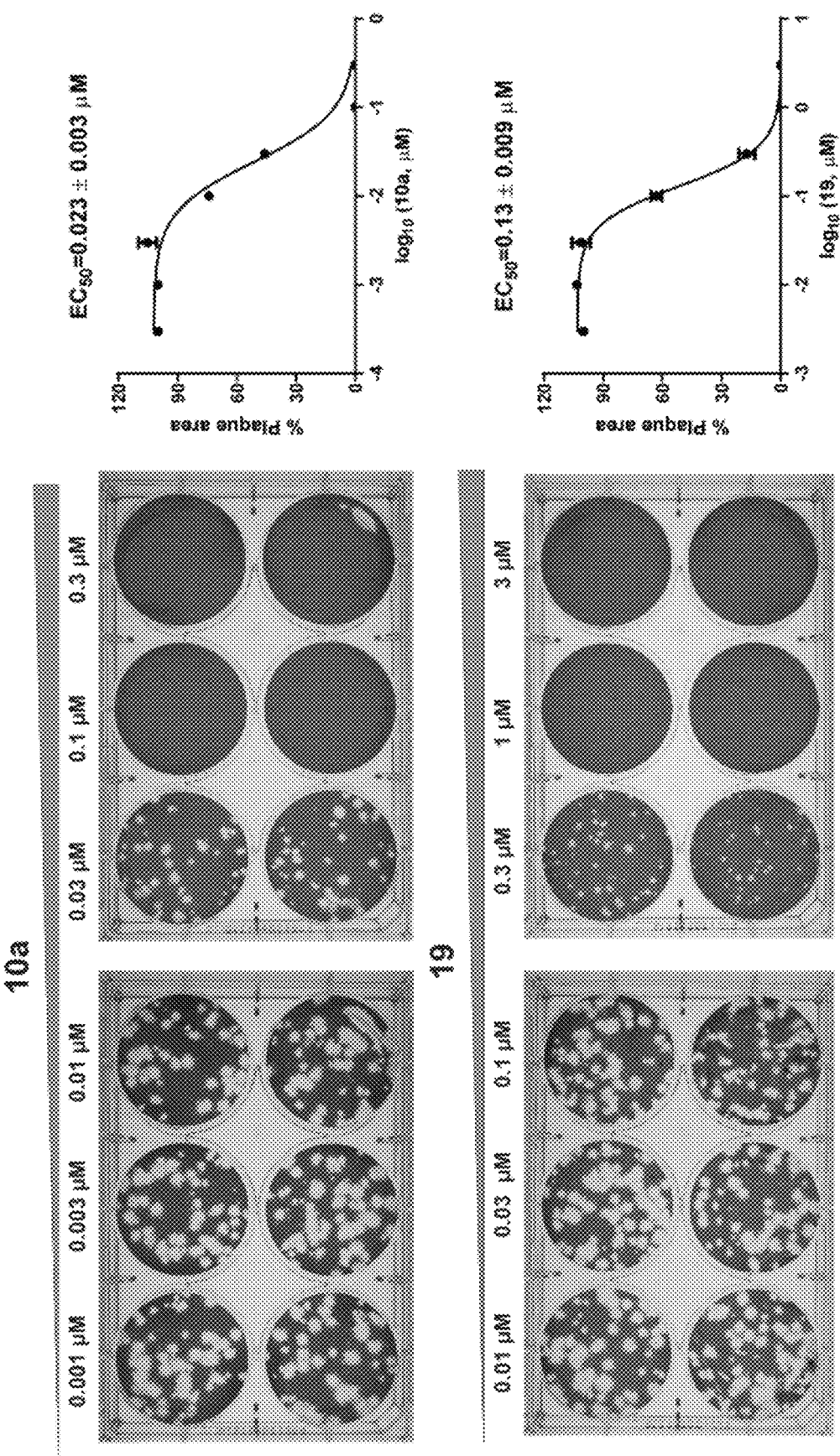

The antiviral activity of compounds 7d, 7h, 10a, and 19 against EV-D68 US/MO/14-18947 were further confirmed in the secondary plaque assay (FIG. 4). Telaprevir, an EV-D68 2A protease inhibitor,[39] was included as a positive control and showed complete inhibition of plaque formation at 3 μM. All four compounds showed dose dependent inhibition of plaque formation and the $EC_{50}$ values for 7d, 7h, 10a, and 19 were 0.025, 0.077, 0.023, and 0.13 μM, respectively. These results were consistent with the primary CPE assay results shown in Table 2.

Antiviral Activity Against EV-D68 in Neuronal Cells

Figure 5:
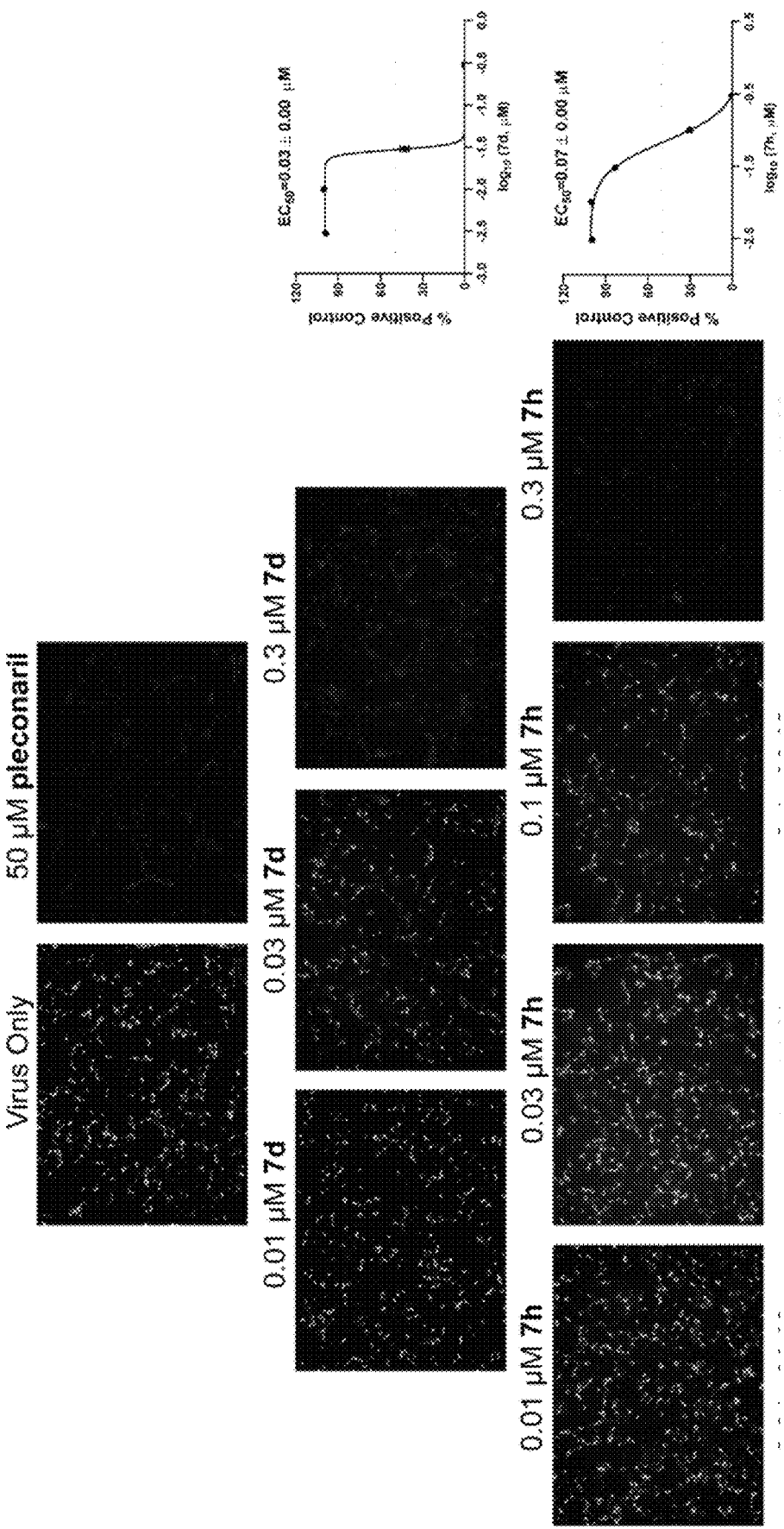
FIG. 5 shows antiviral activity of compounds 7d, 7h, 10a, and 19 against EV-D68 US/MO/14-18947 in neuronal cell line SH-SYSY using immunofluorescence assay. The immunofluorescence signals were quantified in Image J and $EC_{50}$ values were determined through curve fittings in Graphpad Prism 8 using log(concentration of inhibitors) vs percentage of positive control with variable slopes. The results are the mean±standard deviation of two repeats.
Figure 5:
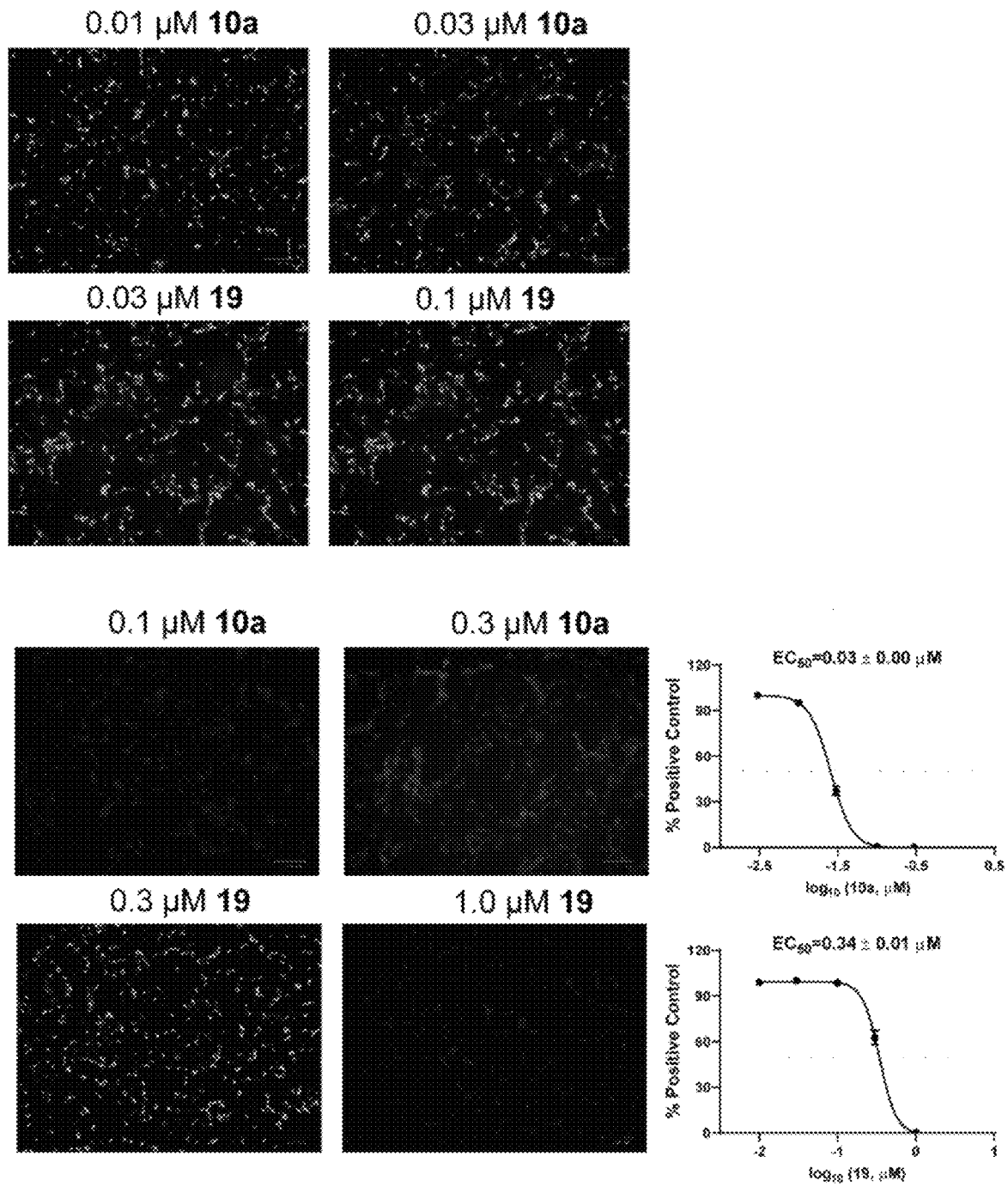

As contemporary EV-D68 viruses are neurotropic, we are interested in testing whether the pyrazolopyridine compounds can inhibit EV-D68 virus replication in neuronal cells. For this, four lead compounds 7d, 7h, 10a, and 19 were tested against the neurotropic EV-D68 strain US/MO/14-18947 in neuronal cell line SH-SYSY (FIG. 5). Viral replication was quantified by immunofluorescence staining using anti-VP1 antibody. Pleconaril was included as a positive control. Pleconaril is a known viral capsid protein VP1 inhibitor and has potent antiviral activity against multiple EV-D68 strains. As shown in FIG. 5, pleconaril completely abolished viral replication at 50 μM as shown by the lack of VP1 fluorescence signal. All four compounds 7d, 7h, 10a, and 19 inhibited viral replication in a dose-response manner with $EC_{50}$ values of 0.03, 0.07, 0.03, and 0.34 μM, respectively, which is consistent with their antiviral efficacy in RD cells (Table 2). In summary, all four pyrazolopyridine compounds potently inhibit the neurotropic EV-D68 virus replication in neuronal cells.

Mechanism of Action

To delineate the mechanism of action of these pyrazolopyridine analogs, we first attempted to select drug-resistant mutant viruses through serial viral passage experiments. For this, we chose compound 7d as a chemical probe and the EV-D68 US/MO/14-18947 virus as a representative non-polio enterovirus. Compound 7d inhibited EV-D68 US/MO/14-18947 virus with an $EC_{50}$ value of 0.07±0.02 μM in CPE assay. EV-D68 US/MO/14-18947 virus was amplified in RD cells with escalating drug selection pressure, starting from ~1×$EC_{50}$ at passages 1 and 2, and increased to 2×$EC_{50}$, 4×$EC_{50}$, and 8×$EC_{50}$ at passages 3, 4, and 5, respectively (Table 3). The drug sensitivity of passage 5 (P5) virus was tested against compound 7d in CPE assay. The $EC_{50}$ of compound 7d against P5 virus was 1.9±0.2 μM, a 27-fold increase compared to P0 virus, suggesting resistance might have emerged. We then sequenced the whole viral genome and identified two mutations in the viral 2C protein, D183V and D323G. To validate the resistance phenotype, we generated recombinant viruses that harbor these 2C mutations and test their drug sensitivity against compound 7d.[33-39] Because P5 virus was sequenced as a mixture, it was unknown whether these two mutations emerged from the same virus or different viruses. As such, we generated three mutant recombinant viruses, the single mutant EV-D68/2C-D183V (rD183V) and EV-D68/2C-D323G (rD323G) viruses, and the double-mutant EV-D68/2C-D183V+D183V (rD183V/D323G) virus using the reverse genetics system we developed earlier.[33, 39] In brief, we introduced 2C-D183V, 2C-D323G, or 2C-D183V+D323G into the EV-D68 US/MO/14-18947 genome individually via a reverse genetics approach using a pHH21 vector. The recombinant WT virus (rWT) was also generated for comparison.

Figure 6A:
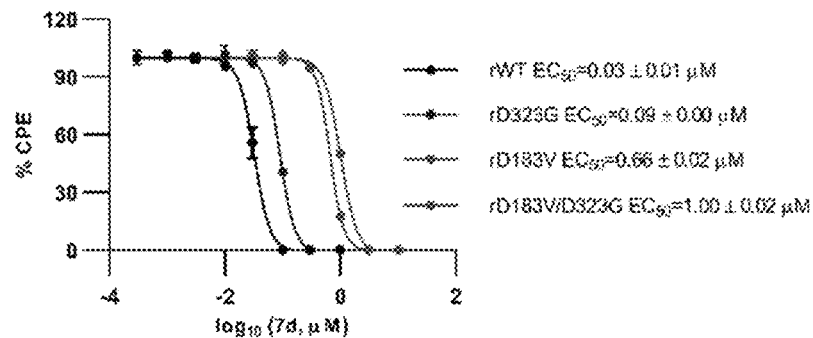
FIG. 6A-D shows mechanism of action of the broad-spectrum antiviral 7d. (A) Drug sensitivity of 7d against different strains of recombinant EV-D68 viruses in plaque assay. (B) Thermal shift binding assay of 7d against purified EV-D68 2C protein and the mutants selected from viral passage experiments. (C) Thermal shift binding assay of 7d against EV-D68 2C, EV-A71 2C, and CVB3 2C. (D) Melting temperature $T_m$ and thermal shift $\Delta T_m$ of EV-D68 2C, EV-A71 2C and CVB3 2C in the presence of different concentrations of 7d.

To determine which recombinant virus(s) confers the phenotypic drug resistance, we titrated 7d against these viruses in the plaque assay (FIG. 6A). It was found that the drug sensitivity of 7d against rD183V virus was decreased by 22-fold compared to rWT virus (rD183V $EC_{50}$=0.66 μM vs rWT $EC_{50}$=0.03 μM), suggesting the 2C-D183V is the predominant drug resistant mutant. In contrast, the 2C-D323G only conferred moderate drug resistance and the drug sensitivity of 7d against rD323G virus was decreased by 3-fold (rD323G EC$_{50}$=0.09 μM vs rWT EC$_{50}$=0.03 μM). The double mutant virus rD183V/D323G had more profound resistance and decreased the drug sensitivity by 33-fold (rD183V/D323G EC$_{50}$=1.00 μM vs rWT EC$_{50}$=0.03 μM). These results suggest that viral 2C protein might be the drug target of 7d, and 2C-D183V mutant and to a less extent 2C-D323G mutant confer the phenotypic drug resistance in cell culture.

Figure 6B:
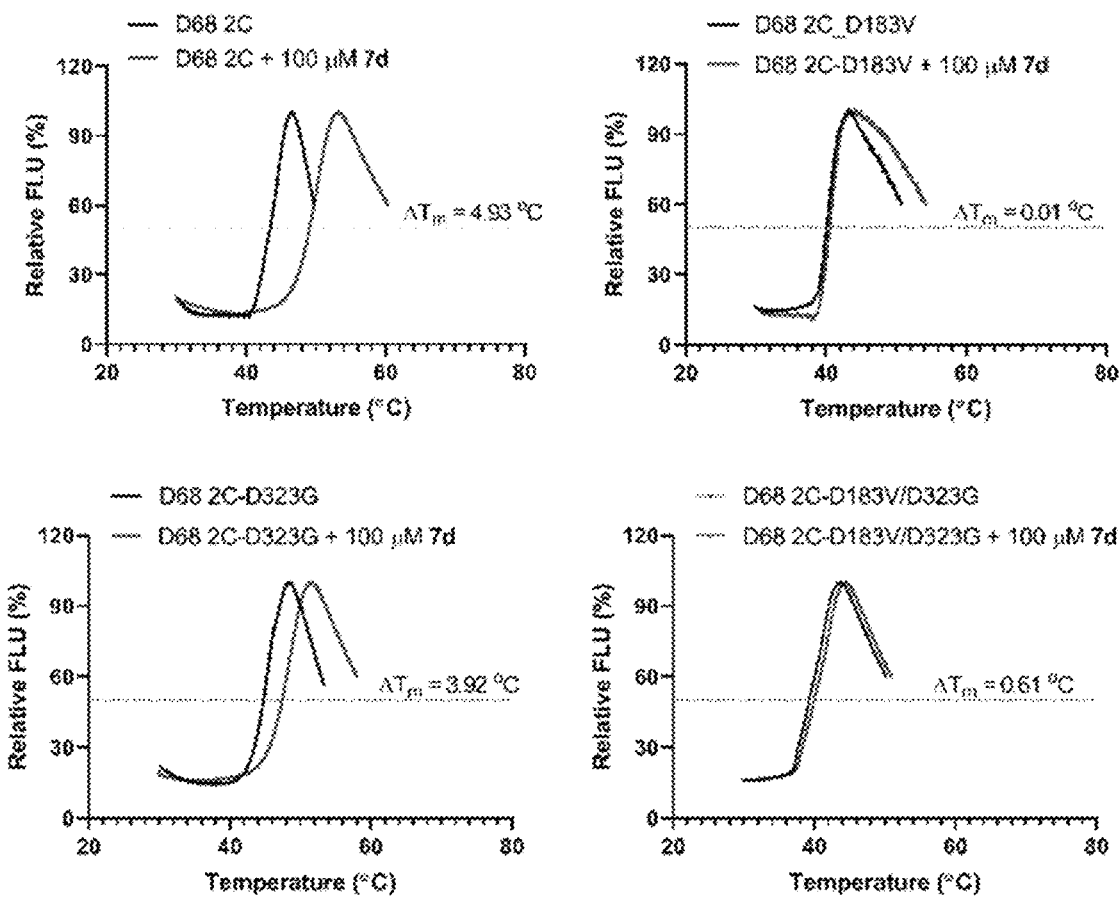

To further confirm that viral 2C protein is the direct drug target of 7d, we performed the differential scanning calorimetry (DSC) assay, also called thermal shift assay, to characterize the direct binding of 7d to 2C protein and its mutants (FIG. 6B). For this, we expressed the EV-D68 US/MO/14-18947 2C protein as well as the 2C-D183V, 2C-D323G, and 2C-D183V/D323G mutants. Binding of 7d to WT 2C protein is evident as shown by stabilization of the protein by 4.93° C. in T$_m$ shift (FIG. 6B). In contrast, no binding was observed for the 2C-D183V mutant (ΔT$_m$=0.01° C.). The 2C-D323G mutant can also be stabilized by 7d and the ΔT$_m$ was 3.92° C., which is comparable to that of the WT 2C protein. The 2C-D183V/D323G double mutant had drastically reduced binding to 7d compared to WT 2C (ΔT$_m$=0.61° C. vs 4.93° C.) (Table 5B). Consistent with CPE assay results described above for recombinant EV-D68 viruses, the DSC assay results showed that the 2C-D183V is the predominant drug resistant mutant, while the 2C-D323G only confers moderate drug resistance, and combination of these two mutants further increased the degree of drug resistance.

Figures 6C, 6D:
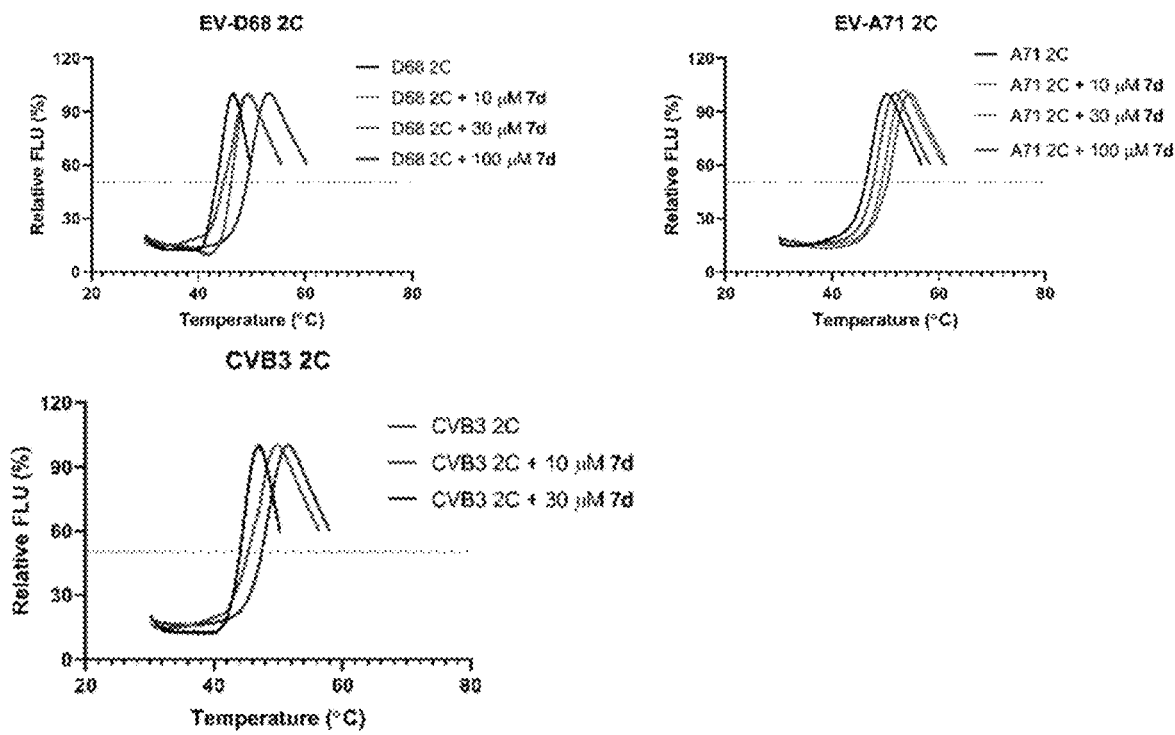

As compound 7d and its analogs have broad-spectrum antiviral activity against EV-A71 and CVB3 in addition to EV-D68, we further expressed the EV-A71 and CVB3 2C protein and performed DSC assay to confirm the direct binding of 7d to these 2C proteins (FIG. 6C). As expected, 7d showed dose-response binding to EV-A71 and CVB3 2C proteins, similar to EV-D68 2C (FIG. 6D). This result implies that 7d inhibits EV-A71 and CVB3 by similarly targeting their viral 2C proteins.

Figure 7:
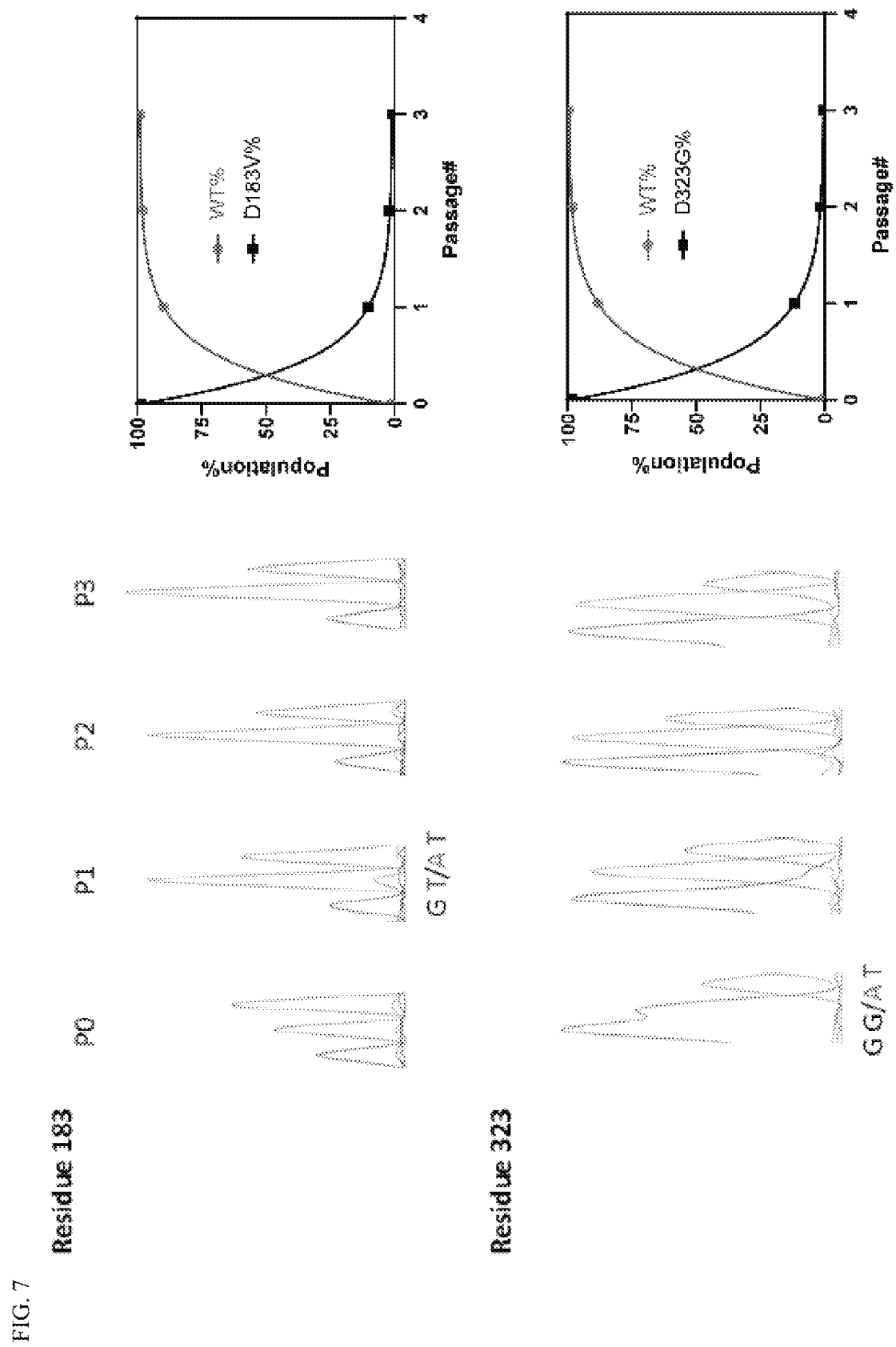
FIG. 7 shows competition growth assay of rD183V/D323G with rWT virus.

The Drug-Resistant rD183V/D323G Virus had a Reduced Fitness of Replication Compared to WT Virus To profile the fitness of replication of the rD183V/D323G virus, we conducted viral competition growth assay with the rWT virus. In the viral competition assay, the rWT and rD183V/D323G viruses were mixed at a 1:100 ratio at passage 0 to favor the mutant virus, and the mixture was co-cultured in RD cells for several passages. At each passage, the viral 2C protein was sequenced to determine the relevant ratios of the substitutions at residues 183 and 323. It was found that the rWT completely overtook the rD183V/D323G mutant virus at passage 3 (FIG. 7). This result suggests that rD183V/D323G virus had a reduced fitness of replication compared to rWT.

Conclusions

Non-polio enteroviruses are important human pathogens and present a challenge for public health, especially in children and immunocompromised adults. Therefore, there is a dire need to develop effect antivirals targeting non-polio enteroviruses including EV-D68, EV-A71, and CVB3. In the experiments described herein, we report our discovery of a series of pyrazolopyridine compounds with potent and broad-spectrum antiviral activity against non-polio enteroviruses. Starting from a screening hit 7a, we conducted structure-activity relationship studies, which yielded several lead compounds including 7d, 7h, 10a, and 19 with significant improved antiviral activity and selectivity. The mechanism of action was delineated through resistance selection using compound 7d as a chemical probe and the EV-D68 US/MO/14-18947 virus as a representative non-polio enterovirus. Two mutations at the viral 2C protein were identified, 2C-D183V and 2C-D323G. Using the reverse genetics system we developed earlier, we generated the recombinant EV-D68 viruses with either single or double 2C mutants selected from the passage experiment. It was found that the D183V is the dominant drug resistant mutant, while D323G only confers moderate resistance. This was further supported by the thermal shift assay results. In addition, we have shown that compound 7d similarly binds to EV-A71 and CVB3 2C protein, implying that its antiviral activity against EV-A71 and CVB3 was through targeting the viral 2C proteins. Although resistance could be isolated in cell culture against 7d, it was found that rD183V/D323G mutant virus had reduced fitness of replication compared with WT as shown by the competition growth assay results (FIG. 7).

To our knowledge, the compounds reported herein represent the most potent antivirals against non-polio enteroviruses with a high selectivity index.

Chemistry

Chemicals were ordered from commercial sources and were used without further purification. Synthesis procedures for reactions described in FIG. 1 were shown below. All final compounds were purified by flash column chromatography. $^1$H and $^{13}$C NMR spectra were recorded on a Bruker-400 NMR spectrometer. Chemical shifts are reported in parts per million referenced with respect to residual solvent (CD$_3$OD) 3.31 ppm, (DMSO-d$_6$) 2.50 ppm, and (CDCl$_3$) 7.24 ppm or from internal standard tetramethylsilane (TMS) 0.00 ppm. The following abbreviations were used in reporting spectra: s, singlet; d, doublet; t, triplet; q, quartet; m, multiplet; dd, doublet of doublets; ddd, doublet of doublet of doublets. All reactions were carried out under N$_2$ atmosphere unless otherwise stated. HPLC-grade solvents were used for all reactions. Flash column chromatography was performed using silica gel (230-400 mesh, Merck). Low-resolution mass spectra were obtained using an ESI technique on a 3200 Q Trap LC/MS/MS system (Applied Biosystems). The purity was assessed by using a Shimadzu LC-MS with a Waters XTerra MS C-18 column (part no. 186000538), 50 mm×2.1 mm, at a flow rate of 0.3 mL/min; λ=250 and 220 nm; mobile phase A, 0.1% formic acid in H$_2$O, and mobile phase B', 0.1% formic in 60% 2-propanol, 30% CH$_3$CN, and 9.9% H$_2$O. All compounds submitted for antiviral CPE assay, cytotoxicity assay, and mechanistic studies were confirmed to be >95.0% purity by LC-MS traces.

Synthesis Procedures

General procedure for the synthesis of 1H-pyrazolo[3,4-b]pyridine-4-carboxylic ester intermediate 3. The 1-alkylpyrazole-5-amine or the 1,3-dialkylpyrazole-5-amine (1 mmol) and the 4-alkyl-2,4-diketoester (1 mmol) was dissolved in acetic acid (10 ml). The resulting solution was refluxed for 5 h under a nitrogen atmosphere. After cooling down to ambient temperature, the solvent was removed in vacuo and the resulting residue was purified by silica gel flash column chromatography (10-50% ethyl acetate/hexane) to give the final product.

General procedure for the synthesis of 1H-pyrazolo[3,4-b]pyridine-4-carboxylic acid intermediate 4. The ester 3 (1 mmol) was dissolved in isopropanol (5 ml). Potassium hydroxide (2 mmol) was added in on portion and the resulting solution was stirred at ambient temperature until complete disappearance of the starting material as monitored by TLC (2 to 4 h). Solvent was removed in vacuo and the resulting residue was extracted with dichloromethane and 3 N HCl. The organic layer was dried over MgSO$_4$, filtered, and concentrated under reduced pressure. The crude product was purified by flash column chromatography (1-10% CH$_3$OH/CH$_2$Cl$_2$) to give the final product.

General procedure of amide coupling. To a DMF solution of carboxylic acid (1 mmol) was added HATU (1 mmol) and DIEA (1.2 mmol). After stirring for 2 minutes, amine (1 mmol) was added. The resulting solution was stirred overnight at ambient temperature. The reaction was diluted with dichloromethane and extracted with aqueous NaHCO$_3$ solution, followed by brine. The organic layer was dried over MgSO$_4$, filtered, and concentrated under reduced pressure. The crude product was purified by flash column chromatography (1-10% CH$_3$OH/CH$_2$Cl$_2$) to give the final product.

General procedure of TFA deprotection of Boc. The Boc-protected amide intermediate (1 mmol) was dissolved in dichloromethane (5 ml), and TFA (2 ml) was added cautiously. The resulting mixture was stirred at ambient temperature for 5 h, and then the solvent was removed and the final product was purified by flash column chromatography (1-10% CH$_3$OH/CH$_2$Cl$_2$).

The following compounds were synthesized using the same procedure as shown for compound 7g: 7a, 7b, 7c, 7d, 7f, 7g, 7k, 7l, 10a, 10b, 10c, 11a, 12a, 12b, 12c, 13, 14, 15a, 16, 17, 18a, 19, 20, 21, and 22.

The following compounds were synthesized using the same procedure as shown for compound 7k: 7e, 7h, 7i, 7j, 7m, 10d, 10e, 10f, 11b, 12d, 12e, 15b, and 18b.

Compound Characterization 6-cyclopropyl-1-(propan-2-yl)-1H-pyrazolo[3,4-b]pyridine-4-carboxylic acid (4a). Yield: 35%. $^1$H NMR (400 MHz, DMSO-d$_6$) δ13.73 (brs, 1H), 8.22 (s, 1H), 7.59 (s, 1H), 5.22-5.02 (m, 1H), 2.44-2.27 (m, 1H), 1.47 (d, J=6.7 Hz, 6H), 1.15-0.98 (m, 4H). $^{13}$C NMR (101 MHz, DMSO-d$_6$) δ 166.27, 162.85, 150.15, 131.66, 131.62, 116.31, 111.10, 48.18, 21.79, 17.11, 11.11. C$_{13}$H$_{15}$N$_3$O$_2$, EI-MS: m/z (M–H$^+$): 244.3 (calculated), 244.3 (found).

1,6-bis(propan-2-yl)-1H-pyrazolo[3,4-b]pyridine-4-carboxylic acid (4b). Yield: 22%. $^1$H NMR (400 MHz, DMSO-d$_6$) δ 13.75 (s, 1H), 8.27 (s, 1H), 7.60 (s, 1H), 5.33-5.11 (m, 1H), 3.35-3.12 (m, 1H), 1.50 (d, J=6.7 Hz, 7H), 1.31 (d, J=6.9 Hz, 7H). $^{13}$C NMR (101 MHz, DMSO-d$_6$) δ 166.66, 166.29, 149.87, 132.22, 131.55, 115.69, 111.31, 48.22, 35.84, 22.39, 21.86. C$_{13}$H$_{17}$N$_3$O$_2$, EI-MS: m/z (M–H$^+$): 246.3 (calculated), 246.3 (found).

6-tert-butyl 1-(propan-2-yl)-1H-pyrazolo[3,4-b]pyridine-4-carboxylic acid (4c). Yield: 31%. $^1$H NMR (400 MHz, DMSO-d$_6$) δ 8.26 (s, 1H), 7.75 (s, 1H), 5.33-5.08 (m, 1H), 1.52 (d, J=6.7 Hz, 6H), 1.41 (s, 9H). $^{13}$C NMR (101 MHz, DMSO-d$_6$) δ 168.41, 166.34, 149.41, 132.15, 131.34, 113.74, 110.91, 48.49, 37.79, 29.94, 21.73. C$_{14}$H$_{19}$N$_3$O$_2$, EI-MS: m/z (M–H$^+$): 260.3 (calculated), 260.3 (found).

6-methyl-1-(propan-2-yl)-1H-pyrazolo[3,4-b]pyridine-4-carboxylic acid (4d). Yield: 27%. $^1$H NMR (400 MHz, DMSO-d$_6$) δ 13.75 (brs, 1H), 8.26 (s, 1H), 7.55 (s, 1H), 5.39-5.09 (m, 1H), 2.67 (s, 3H), 1.48 (d, J=6.7 Hz, 6H). $^{13}$C NMR (101 MHz, DMSO-d$_6$) δ 166.16, 158.12, 149.92, 131.74, 131.57, 117.86, 110.78, 47.80, 24.37, 21.88. C$_{11}$H$_{13}$N$_3$O$_2$, EI-MS: m/z (M–H$^+$): 218.2 (calculated), 218.3 (found).

1-cyclopentyl-6-methyl-1H-pyrazolo[3,4-b]pyridine-4-carboxylic acid (4e). Yield: 41%. $^1$H NMR (400 MHz, DMSO-d$_6$) δ 8.26 (s, 1H), 7.55 (s, 1H), 5.47-5.29 (m, 1H), 2.67 (s, 3H), 2.18-2.06 (m, 2H), 2.06-1.78 (m, 4H), 1.78-1.60 (m, 2H). $^{13}$C NMR (101 MHz, DMSO-d$_6$) δ 166.18, 158.15, 150.47, 131.97, 131.68, 117.85, 110.84, 56.58, 31.97, 24.36, 24.22. C$_{13}$H$_{15}$N$_3$O$_2$, EI-MS: m/z (M–H$^+$): 244.3 (calculated), 244.3 (found).

6-methyl-1-propyl-1H-pyrazolo[3,4-b]pyridine-4-carboxylic acid (4). Yield: 38%. $^1$H NMR (400 MHz, DMSO-d$_6$) δ 13.76 (brs, 1H), 8.25 (s, 1H), 7.55 (s, 1H), 4.40 (t, J=7.0 Hz, 2H), 2.66 (s, 3H), 2.01-1.75 (m, 2H), 0.82 (t, J=7.4 Hz, 3H). $^{13}$C NMR (101 MHz, DMSO-d$_6$) δ 166.13, 158.38, 150.79, 131.79, 131.68, 117.79, 110.56, 47.93, 24.37, 22.46, 11.02. C$_{11}$H$_{13}$N$_3$O$_2$, EI-MS: m/z (M–H$^+$): 218.2 (calculated), 218.2 (found).

1-ethyl-6-methyl-1H-pyrazolo[3,4-b]pyridine-4-carboxylic acid (4g). Yield: 27%. $^1$H NMR (400 MHz, DMSO-d$_6$) δ 13.77 (brs, 1H), 8.25 (s, 1H), 7.55 (s, 1H), 4.48 (q, J=7.2 Hz, 2H), 2.67 (s, 3H), 1.42 (t, J=7.2 Hz, 3H). $^{13}$C NMR (101 MHz, DMSO-d$_6$) δ 166.12, 158.38, 150.29, 131.81, 131.70, 117.80, 110.68, 41.41, 24.35, 14.70. C$_{10}$H$_{11}$N$_3$O$_2$, EI-MS: m/z (M–H$^+$): 204.2 (calculated), 204.2 (found).

6-cyclopropyl-1-ethyl-1H-pyrazolo[3,4-b]pyridine-4-carboxylic acid (4h). Yield: 36%. $^1$H NMR (400 MHz, DMSO-d$_6$) δ 13.78 (brs, 1H), 8.21 (s, 1H), 7.59 (s, 1H), 4.42 (q, J=7.2 Hz, 2H), 2.44-2.27 (m, 1H), 1.40 (t, J=7.2 Hz, 3H), 1.19-0.98 (m, 4H). $^{13}$C NMR (101 MHz, DMSO-d$_6$) δ 166.17, 163.06, 150.43, 131.72, 131.62, 116.21, 110.84, 41.36, 17.06, 14.57, 11.04. C$_{12}$H$_{13}$N$_3$O$_2$, EI-MS: m/z (M–H$^+$): 230.3 (calculated), 230.2 (found).

6-cyclopropyl-1-methyl-1H-pyrazolo[3,4-b]pyridine-4-carboxylic acid (4i). Yield: 22%. $^1$H NMR (400 MHz, DMSO-d$_6$) δ 13.80 (brs, 1H), 8.21 (s, 1H), 7.60 (s, 1H), 4.00 (s, 3H), 2.44-2.32 (m, 1H), 1.18-1.00 (m, 4H). $^{13}$C NMR (101 MHz, DMSO-d$_6$) δ 166.15, 163.23, 150.96, 131.68, 131.62, 116.17, 110.69, 33.51, 17.09, 10.99. C$_{11}$H$_{11}$N$_3$O$_2$, EI-MS: m/z (M–H$^+$): 216.2 (calculated), 216.2 (found).

1-tert-butyl-6-cyclopropyl-3-methyl-1H-pyrazolo[3,4-b]pyridine-4-carboxylic acid (4j). Yield: 21%. $^1$H NMR (400 MHz, DMSO-d$_6$) δ 13.67 (s, 1H), 7.46 (s, 1H), 2.53 (s, 3H), 2.40-2.21 (m, 1H), 1.70 (s, 9H), 1.13-0.94 (m, 4H). $^{13}$C NMR (101 MHz, DMSO-d$_6$) δ 166.96, 161.25, 151.40, 137.42, 133.83, 114.86, 109.86, 58.78, 28.65, 16.68, 15.45, 11.01. C$_{15}$H$_{19}$N$_3$O$_2$, EI-MS: m/z (M–H$^+$): 272.3 (calculated), 272.3 (found).

1-tert-butyl-3,6-dimethyl-1H-pyrazolo[3,4-b]pyridine-4-carboxylic acid (4k). Yield: 18%. $^1$H NMR (400 MHz, DMSO-d$_6$) δ 7.34 (s, 1H), 2.62 (s, 3H), 2.53 (s, 3H), 1.73 (s, 9H). $^{13}$C NMR (101 MHz, DMSO-d$_6$) δ 166.97, 156.46, 151.29, 137.34, 134.29, 115.96, 109.75, 59.00, 28.74, 24.52, 15.44. C$_{13}$H$_{17}$N$_3$O$_2$, EI-MS: m/z (M–H$^+$): 246.3 (calculated), 246.3 (found).

6-cyclopropyl-1-propyl-1H-pyrazolo[3,4-b]pyridine-4-carboxylic acid (4l). Yield: 35%. $^1$H NMR (400 MHz, DMSO-d$_6$) δ 13.76 (brs, 1H), 8.22 (s, 1H), 7.59 (s, 1H), 4.35 (t, J=6.8 Hz, 2H), 2.44-2.30 (m, 1H), 1.95-1.76 (m, 2H), 1.18-0.98 (m, 4H), 0.78 (t, J=7.4 Hz, 3H). $^{13}$C NMR (101 MHz, DMSO-d$_6$) δ 166.16, 163.06, 150.98, 131.74, 131.58, 116.23, 110.68, 47.85, 22.42, 17.03, 11.06. C$_{13}$H$_{15}$N$_3$O$_2$, EI-MS: m/z (M–H$^+$): 244.3 (calculated), 244.3 (found).

1-(butan-2-yl)-6-cyclopropyl-1H-pyrazolo[3,4-b]pyridine-4-carboxylic acid (4m). Yield: 38%. $^1$H NMR (400 MHz, DMSO-d$_6$) δ 8.24 (s, 1H), 7.60 (s, 1H), 4.97-4.79 (m, 1H), 2.44-2.30 (m, 1H), 2.03-1.75 (m, 2H), 1.47 (d, J=6.7 Hz, 3H), 1.18-0.98 (m, 4H), 0.62 (t, J=7.3 Hz, 3H). $^{13}$C NMR (101 MHz, DMSO-$d_6$) δ 166.22, 162.79, 150.90, 131.74, 116.21, 110.79, 53.73, 28.79, 20.04, 17.01, 11.07, 11.05, 10.62. $C_{14}H_{17}N_3O_2$, EI-MS: m/z (M–H$^+$): 258.3 (calculated), 258.3 (found).

6-cyclopropyl-1-(1-cyclopropylethyl)-1H-pyrazolo[3,4-b]pyridine-4-carboxylic acid (4n). Yield: 29%. $^1$H NMR (400 MHz, DMSO-$d_6$) δ 8.25 (s, 1H), 7.58 (s, 1H), 4.34-4.15 (m, 1H), 2.44-2.27 (m, 1H), 1.61 (d, J=6.8 Hz, 3H), 1.46-1.28 (m, 1H), 1.14-0.95 (m, 4H), 0.65-0.49 (m, 1H), 0.47-0.37 (m, 1H), 0.37-0.13 (m, 2H). $^{13}$C NMR (101 MHz, DMSO-$d_6$) δ166.36, 162.63, 150.51, 131.72, 116.19, 111.16, 57.16, 19.63, 17.23, 16.98, 10.96, 10.91, 3.70, 3.55. $C_{15}H_{17}N_3O_2$, EI-MS: m/z (M–H$^+$): 270.3 (calculated), 270.3 (found).

6-cyclopropyl-N-(2-methoxyethyl)-1-(propan-2-yl)-1H-pyrazolo[3,4-b]pyridine-4-carboxamide (7a). Yield: 75%. $^1$H NMR (400 MHz, DMSO-$d_6$) δ 8.80 (s, 1H), 8.20 (d, J=0.5 Hz, 1H), 7.42 (s, 1H), 5.21-5.00 (m, 1H), 3.57-3.42 (m, 4H), 3.29 (s, 3H), 2.34-2.16 (m, 1H), 1.47 (d, J=6.7 Hz, 6H), 1.13-1.02 (m, 4H). $^{13}$C NMR (101 MHz, DMSO-$d_6$) δ 166.45, 164.90, 149.58, 136.33, 131.55, 112.73, 110.96, 59.50, 47.93, 42.08, 36.08, 22.36, 21.81. $C_{16}H_{22}N_4O_2$, EI-MS: m/z (M+H$^+$): 303.4 (calculated), 303.4 (found).

6-cyclopropyl-1-(propan-2-yl)-N-[2-(pyrrolidin-1-yl)ethyl]-1H-pyrazolo[3,4-b]pyridine-4-carboxamide (7b). Yield: 72%. $^1$H NMR (400 MHz, DMSO-$d_6$) δ 9.02 (t, J=5.7 Hz, 1H), 8.24 (s, 1H), 7.56 (s, 1H), 5.21-5.00 (m, 1H), 3.67-3.48 (m, 2H), 3.14-2.79 (m, 6H), 2.32-2.21 (m, 1H), 1.91-1.71 (m, 4H), 1.46 (d, J=6.7 Hz, 7H), 1.17-1.03 (m, 4H). $^{13}$C NMR (101 MHz, DMSO-$d_6$) δ 164.90, 162.64, 149.83, 135.37, 131.58, 113.08, 110.70, 53.66, 53.24, 47.89, 36.89, 22.79, 21.74, 17.44, 10.78. $C_{19}H_{27}N_5O$, EI-MS: m/z (M+H$^+$):342.5 (calculated), 342.5 (found).

6-cyclopropyl-N-[2-(diethylamino)ethyl]-1-(propan-2-yl)-1H-pyrazolo[3,4-b]pyridine-4-carboxamide (7c). Yield: 81%. $^1$H NMR (400 MHz, DMSO-$d_6$) δ 8.69 (s, 1H), 8.22 (s, 1H), 7.40 (s, 1H), 5.20-5.04 (m, 1H), 3.51-3.31 (m, 2H), 2.71-2.61 (m, 2H), 2.61-2.52 (m, 4H), 2.33-2.20 (m, 1H), 1.47 (d, J=6.7 Hz, 6H), 1.14-1.03 (m, 4H), 0.99 (t, J=7.1 Hz, 6H). $^{13}$C NMR (101 MHz, DMSO-$d_6$) δ 164.66, 162.56, 149.82, 135.89, 131.49, 112.87, 110.67, 51.10, 47.89, 46.63, 37.22, 21.72, 17.35, 11.58, 10.76. $C_{19}H_{29}N_5O$, EI-MS: m/z (M+H$^+$):344.5 (calculated), 344.5 (found).

6-cyclopropyl-N-[2-(dimethylamino)ethyl]-1-(propan-2-yl)-1H-pyrazolo[3,4-b]pyridine-4-carboxamide (7d). Yield: 79%. $^1$H NMR (400 MHz, DMSO-$d_6$) δ 8.73 (t, J=5.7 Hz, 1H), 8.22 (s, 1H), 7.44 (s, 1H), 5.23-5.02 (m, 1H), 3.53-3.37 (m, 2H), 2.56 (t, J=6.7 Hz, 2H), 2.28 (s, 7H), 1.47 (d, J=6.7 Hz, 6H), 1.08 (d, J=6.4 Hz, 4H). $^{13}$C NMR (101 MHz, DMSO-$d_6$) δ 164.71, 162.56, 149.83, 135.77, 131.53, 112.97, 110.71, 57.60, 47.88, 44.78, 36.92, 21.73, 17.35, 10.75. $C_{17}H_{25}N_5O$, EI-MS: m/z (M+H$^+$):316.4 (calculated), 316.4 (found).

N-(azetidin-3-yl)-6-cyclopropyl-1-(propan-2-yl)-1H-pyrazolo[3,4-b]pyridine-4-carboxamide (7e). TFA salt. Yield: 65%. $^1$H NMR (400 MHz, DMSO-$d_6$) δ 9.57 (d, J=6.7 Hz, 1H), 9.16 (s, 2H), 8.25 (s, 1H), 7.52 (s, 1H), 5.24-5.03 (m, 1H), 4.99-4.79 (m, 1H), 4.35-4.05 (m, 4H), 2.37-2.19 (m, 1H), 1.48 (d, J=6.7 Hz, 6H), 1.18-1.04 (m, 4H). $^{13}$C NMR (101 MHz, DMSO-$d_6$) δ 164.79, 162.71, 149.88, 134.65, 131.52, 113.24, 110.56, 51.83, 48.02, 41.52, 21.76, 17.40, 10.85. $C_{16}H_{21}N_5O$, EI-MS: m/z (M+H$^+$): 300.4 (calculated), 300.4 (found).

6-cyclopropyl-N-[1-(dimethylamino)propan-2-yl]-1-(propan-2-yl)-1H-pyrazolo[3,4-b]pyridine-4-carboxamide (7f). Yield: 86%. $^1$H NMR (400 MHz, DMSO-$d_6$) δ 8.52 (d, J=8.2 Hz, 1H), 8.22 (s, 1H), 7.46 (s, 1H), 5.24-5.03 (m, 1H), 4.34-4.16 (m, 1H), 2.63-2.50 (m, 1H), 2.42-2.18 (m, 8H), 1.48 (d, J=6.7 Hz, 6H), 1.19 (d, J=6.6 Hz, 3H), 1.15-1.04 (m, 4H). $^{13}$C NMR (101 MHz, DMSO-$d_6$) δ 164.18, 162.48, 149.81, 136.13, 131.60, 113.13, 110.79, 63.65, 47.86, 45.03, 42.83, 21.74, 21.71, 18.73, 17.30, 10.73, 10.71. $C_{18}H_{27}N_5O$, EI-MS: m/z (M+H$^+$): 330.4 (calculated), 330.4 (found).

6-cyclopropyl-N-(1-methylpyrrolidin-3-yl)-1-(propan-2-yl)-1H-pyrazolo[3,4-b]pyridine-4-carboxamide (7g). Yield: 77%. $^1$H NMR (400 MHz, CDCl$_3$) δ 8.27 (s, 1H), 7.97 (d, J=8.4 Hz, 1H), 7.42 (s, 1H), 5.27-5.13 (m, 1H), 5.04-4.84 (m, 1H), 3.56-3.40 (m, 1H), 3.38-3.22 (m, 1H), 2.96-2.83 (m, 1H), 2.67 (s, 3H), 2.65-2.48 (m, 2H), 2.27-2.15 (m, 1H), 2.15-2.02 (m, 1H), 1.55 (d, J=6.7 Hz, 6H), 1.22-1.13 (m, 2H), 1.10-0.99 (m, 2H). $^{13}$C NMR (101 MHz, CDCl$_3$) δ165.43, 163.48, 150.69, 134.62, 131.61, 113.55, 111.00, 62.30, 54.87, 49.01, 48.64, 41.15, 32.51, 22.08, 17.94, 11.19. $C_{18}H_{25}N_5O$, EI-MS: m/z (M+H$^+$): 328.4 (calculated), 328.4 (found).

6-cyclopropyl-N-[2-(methylamino)ethyl]-1-(propan-2-yl)-1H-pyrazolo[3,4-b]pyridine-4-carboxamide (7h). TFA salt. Yield: 72%. $^1$H NMR (400 MHz, DMSO-$d_6$) δ 9.04 (t, J=5.7 Hz, 1H), 8.77 (s, 2H), 8.25 (s, 1H), 7.49 (s, 1H), 5.23-5.01 (m, 1H), 3.63 (q, J=5.9 Hz, 2H), 3.23-3.07 (m, 2H), 2.62 (s, 3H), 2.35-2.18 (m, 1H), 1.47 (d, J=6.7 Hz, 6H), 1.16-1.01 (m, 4H). $^{13}$C NMR (101 MHz, DMSO-$d_6$) δ 165.51, 162.60, 149.90, 135.20, 131.68, 113.25, 110.69, 47.97, 47.66, 35.69, 32.59, 21.76, 17.40, 10.77. $C_{16}H_{23}N_5O$, EI-MS: m/z (M+H$^+$):302.4 (calculated), 302.4 (found).

N-(2-aminoethyl)-6-cyclopropyl-1-(propan-2-yl)-1H-pyrazolo[3,4-b]pyridine-4-carboxamide (7i). TFA salt. Yield: 68%. $^1$H NMR (400 MHz, CD$_3$OD) δ 8.26 (s, 1H), 7.46 (s, 1H), 5.28-5.10 (m, 1H), 3.77 (t, J=5.9 Hz, 2H), 3.28 (t, J=5.9 Hz, 2H), 2.31-2.18 (m, 1H), 1.51 (d, J=6.8 Hz, 6H), 1.22-1.00 (m, 4H). $^{13}$C NMR (101 MHz, CD$_3$OD) δ168.93, 165.18, 151.68, 136.17, 133.00, 132.91, 114.94, 112.00, 49.84, 40.66, 38.69, 22.13, 18.42, 11.57. $C_{15}H_{21}N_5O$, EI-MS: m/z (M+H$^+$): 288.4 (calculated), 288.4 (found).

N-(1-aminopropan-2-yl)-6-cyclopropyl-1-(propan-2-yl)-1H-pyrazolo[3,4-b]pyridine-4-carboxamide (7j). TFA salt. Yield: 81%. $^1$H NMR (400 MHz, DMSO-$d_6$) δ 8.82 (d, J=8.1 Hz, 1H), 8.24 (s, 1H), 8.13 (s, 3H), 7.56 (s, 1H), 5.21-5.04 (m, 1H), 4.45-4.24 (m, 1H), 3.12-2.93 (m, 2H), 2.35-2.22 (m, 1H), 1.48 (dd, J=6.7, 1.2 Hz, 6H), 1.26 (d, J=6.7 Hz, 3H), 1.18-1.04 (m, 4H). $^{13}$C NMR (101 MHz, DMSO-$d_6$) δ 164.98, 162.54, 149.91, 135.54, 131.75, 113.47, 110.83, 47.96, 43.57, 43.06, 21.78, 21.76, 17.96, 17.38, 10.78, 10.68. $C_{16}H_{23}N_5O$, EI-MS: m/z (M+H$^+$): 302.4 (calculated), 302.4 (found).

6-cyclopropyl-N-[3-(diethylamino)propyl]-1-(propan-2-yl)-1H-pyrazolo[3,4-b]pyridine-4-carboxamide (7k). Yield: 86%. $^1$H NMR (400 MHz, CD$_3$OD) δ 8.24 (s, 1H), 7.46 (s, 1H), 5.34-5.11 (m, 1H), 3.58 (t, J=6.6 Hz, 2H), 3.30-3.13 (m, 6H), 2.38-2.23 (m, 1H), 2.20-1.98 (m, 2H), 1.55 (d, J=6.8 Hz, 6H), 1.35 (t, J=7.3 Hz, 6H), 1.25-1.02 (m, 4H). $^{13}$C NMR (101 MHz, CD$_3$OD) δ 168.59, 165.26, 151.77, 136.56, 132.85, 132.77, 114.83, 112.06, 50.85, 49.92, 48.43, 37.97, 25.43, 22.15, 18.46, 11.61, 9.27. $C_{20}H_{31}N_5O$, EI-MS: m/z (M+H$^+$):358.5 (calculated), 358.5 (found).

6-cyclopropyl-N-[3-(dimethylamino)propyl]-1-(propan-2-yl)-1H-pyrazolo[3,4-b]pyridine-4-carboxamide (7l). Yield: 79%. $^1$H NMR (400 MHz, DMSO-$d_6$) δ 8.78 (t, J=5.6 Hz, 1H), 8.19 (s, 1H), 7.39 (s, 1H), 5.12 (hept, J=6.7 Hz, 1H), 3.46-3.20 (m, 2H), 2.36-2.22 (m, 3H), 2.16 (s, 6H), 1.78-1.63 (m, 2H), 1.47 (d, J=6.7 Hz, 6H), 1.15-1.01 (m, 4H). $^{13}$C NMR (101 MHz, DMSO-$d_6$) δ 164.68, 162.56, 149.84, 135.85, 131.53, 112.92, 110.71, 56.31, 47.88, 44.46, 37.39, 26.27, 21.73, 17.37, 10.76. $C_{18}H_{27}N_5O$, EI-MS: m/z (M+H$^+$): 330.4 (calculated), 330.4 (found).

6-cyclopropyl-N-[3-(methylamino)propyl]-1-(propan-2-yl)-1H-pyrazolo[3,4-b]pyridine-4-carboxamide (7m). TFA salt. Yield: 65%. $^1$H NMR (400 MHz, DMSO-d$_6$) δ 8.98 (t, J=5.7 Hz, 1H), 8.79 (s, 2H), 8.22 (s, 1H), 7.46 (s, 1H), 5.21-5.03 (m, 1H), 3.40 (q, J=6.4 Hz, 2H), 3.05-2.89 (m, 2H), 2.65-2.54 (m, 3H), 2.40-2.21 (m, 1H), 1.90 (p, J=6.9 Hz, 2H), 1.46 (d, J=6.7 Hz, 6H), 1.08 (d, J=6.4 Hz, 4H). $^{13}$C NMR (101 MHz, DMSO-d$_6$) δ 165.13, 162.66, 149.91, 135.59, 131.60, 113.07, 110.73, 47.97, 46.18, 36.32, 32.41, 25.70, 21.76, 17.38, 10.80. $C_{17}H_{25}N_5O$, EI-MS: m/z (M+H$^+$): 316.4 (calculated), 316.4 (found).

N-[2-(dimethylamino)ethyl]-1,6-bis(propan-2-yl)-1H-pyrazolo[3,4-b]pyridine-4-carboxamide (10a). Yield: 84%. $^1$H NMR (400 MHz, DMSO-d$_6$) δ 8.72 (t, J=5.7 Hz, 1H), 8.28 (s, 1H), 7.50 (s, 1H), 5.31-5.13 (m, 1H), 3.53-3.39 (m, 2H), 3.27-3.13 (m, 1H), 2.56-2.49 (m, 2H), 2.25 (s, 6H), 1.51 (d, J=6.7 Hz, 6H), 1.35 (d, J=6.9 Hz, 6H). $^{13}$C NMR (101 MHz, DMSO-d$_6$) δ 166.44, 164.69, 149.57, 136.29, 131.48, 112.69, 110.93, 57.81, 47.92, 45.00, 37.14, 36.04, 22.35, 21.79. $C_{17}H_{27}N_5O$, EI-MS: m/z (M+H$^+$): 318.4 (calculated), 318.4 (found).

N-(2-hydroxyethyl)-1,6-bis(propan-2-yl)-1H-pyrazolo[3,4-b]pyridine-4-carboxamide (10b). Yield: 73%. $^1$H NMR (400 MHz, DMSO-d$_6$) δ 8.74 (t, J=5.6 Hz, 1H), 8.26 (d, J=0.5 Hz, 1H), 7.51 (s, 1H), 5.30-5.08 (m, 1H), 4.79 (t, J=5.6 Hz, 1H), 3.57 (q, J=5.9 Hz, 2H), 3.40 (q, J=6.0 Hz, 2H), 3.19 (h, J=6.9 Hz, 1H), 1.50 (d, J=6.7 Hz, 6H), 1.34 (d, J=6.9 Hz, 6H). $^{13}$C NMR (101 MHz, DMSO-d$_6$) δ 166.45, 164.90, 149.58, 136.33, 131.55, 112.73, 110.96, 59.50, 47.93, 42.08, 36.08, 22.36, 21.81. $C_{15}H_{22}N_4O_2$, EI-MS: m/z (M+H$^+$): 291.4 (calculated), 291.4 (found).

N-[1-(dimethylamino)propan-2-yl]-1,6-bis(propan-2-yl)-1H-pyrazolo[3,4-b]pyridine-4-carboxamide (10c). Yield: 75%. $^1$H NMR (400 MHz, CD$_3$OD) δ 8.29 (s, 1H), 7.51 (s, 1H), 5.43-5.24 (m, 1H), 4.53-4.32 (m, 1H), 3.31-3.19 (m, 1H), 2.83-2.65 (m, 1H), 2.51-2.29 (m, 7H), 1.59 (d, J=6.7, 1.5 Hz, 6H), 1.42 (d, J=6.9, 1.5 Hz, 6H), 1.31 (d, J=6.6, 1.5 Hz, 3H). $^{13}$C NMR (101 MHz, CD$_3$OD) δ168.93, 167.84, 151.45, 137.96, 132.96, 114.36, 112.48, 65.31, 49.90, 45.74, 44.78, 38.04, 22.91, 22.89, 22.23, 19.34. $C_{18}H_{29}N_5O$, EI-MS: m/z (M+H$^+$): 332.5 (calculated), 332.4 (found).

N-[2-(methylamino)ethyl]-1,6-bis(propan-2-yl)-1H-pyrazolo[3,4-b]pyridine-4-carboxamide (10d). TFA salt. Yield: 71%. $^1$H NMR (400 MHz, DMSO-d$_6$) δ 9.18 (t, J=5.6 Hz, 1H), 9.00 (s, 2H), 8.30 (s, 1H), 7.61 (s, 1H), 5.32-5.08 (m, 1H), 3.65 (q, J=5.9 Hz, 2H), 3.28-3.09 (m, 3H), 2.62 (s, 3H), 1.49 (d, J=6.7 Hz, 6H), 1.33 (d, J=6.9 Hz, 6H). $^{13}$C NMR (101 MHz, DMSO-d$_6$) δ166.55, 165.52, 149.68, 135.63, 131.69, 113.11, 110.97, 48.02, 47.62, 36.14, 35.72, 32.52, 22.35, 21.83. $C_{16}H_{25}N_5O$, EI-MS: m/z (M+H$^+$): 304.4 (calculated), 304.4 (found).

N-(2-aminoethyl)-1,6-bis(propan-2-yl)-1H-pyrazolo[3,4-b]pyridine-4-carboxamide (10e). TFA salt. Yield: 80%. $^1$H NMR (400 MHz, DMSO-d$_6$) δ 9.09 (t, J=5.6 Hz, 1H), 8.29 (s, 1H), 8.12 (brs, 3H), 7.59 (s, 1H), 5.35-5.09 (m, 1H), 3.59 (q, J=6.0 Hz, 2H), 3.29-3.12 (m, 1H), 3.13-2.96 (m, 2H), 1.50 (d, J=6.7 Hz, 6H), 1.34 (d, J=6.9 Hz, 6H). $^{13}$C NMR (101 MHz, DMSO-d$_6$) δ 166.53, 165.49, 149.64, 135.72, 131.65, 113.06, 110.93, 48.00, 38.34, 37.10, 36.13, 22.36, 21.84. $C_{15}H_{23}N_5O$, EI-MS: m/z (M+H$^+$): 290.4 (calculated), 290.4 (found).

N-(1-aminopropan-2-yl)-1,6-bis(propan-2-yl)-1H-pyrazolo[3,4-b]pyridine-4-carboxamide (10f). TFA salt. Yield: 73%. $^1$H NMR (400 MHz, DMSO-d$_6$) δ 8.78 (d, J=8.1 Hz, 1H), 8.27 (s, 1H), 8.04 (brs, 3H), 7.57 (s, 1H), 5.31-5.10 (m, 1H), 4.46-4.20 (m, 1H), 3.29-3.13 (m, 1H), 3.11-2.94 (m, 2H), 1.50 (d, J=6.7, 1.3 Hz, 6H), 1.34 (d, J=6.9 Hz, 6H), 1.26 (d, J=6.8 Hz, 3H). $^{13}$C NMR (101 MHz, DMSO-d$_6$) δ 166.41, 165.00, 149.63, 135.99, 131.68, 113.10, 111.02, 47.98, 43.56, 43.09, 36.09, 22.36, 21.82, 21.79, 17.94. $C_{16}H_{25}N_5O$, EI-MS: m/z (M+H$^+$): 304.4 (calculated), 304.4 (found).

6-tert-butyl-N-[2-(dimethylamino)ethyl]-1-(propan-2-yl)-1H-pyrazolo[3,4-b]pyridine-4-carboxamide (11a). Yield: 83%. $^1$H NMR (400 MHz, CD$_3$OD) δ 8.27 (s, 1H), 7.68 (s, 1H), 5.38-5.20 (m, 1H), 3.72-3.56 (m, 2H), 2.79 (t, J=6.6 Hz, 2H), 2.47 (s, 6H), 1.62-1.51 (m, 6H), 1.46 (d, J=1.4 Hz, 9H). $^{13}$C NMR (101 MHz, CD$_3$OD) δ 168.93, 165.18, 151.68, 136.17, 133.00, 132.91, 114.94, 112.00, 49.84, 40.66, 38.69, 22.13, 18.42, 11.57. $C_{18}H_{29}N_5O$, EI-MS: m/z (M+H$^+$): 332.5 (calculated), 332.4 (found).

N-(2-aminoethyl)-6-tert-butyl-1-(propan-2-yl)-1H-pyrazolo[3,4-b]pyridine-4-carboxamide (11b). TFA salt. Yield: 78%. $^1$HNMR (400 MHz, DMSO-d$_6$) δ9.11 (t, J=5.6 Hz, 1H), 8.29 (s, 1H), 8.06 (brs, 3H), 7.74 (s, 1H), 5.30-5.09 (m, 1H), 3.60 (q, J=6.1 Hz, 2H), 3.14-2.98 (m, 2H), 1.51 (d, J=6.7 Hz, 6H), 1.43 (s, 9H). $^{13}$C NMR (101 MHz, DMSO-d$_6$) δ168.43, 165.62, 149.20, 135.52, 131.50, 111.43, 110.56, 48.33, 38.37, 37.97, 37.09, 29.99, 21.74. $C_{16}H_{25}N_5O$, EI-MS: m/z (M+H$^+$): 304.4 (calculated), 304.4 (found).

N-[2-(dimethylamino)ethyl]-6-methyl-1-(propan-2-yl)-1H-pyrazolo[3,4-b]pyridine-4-carboxamide (12a). Yield: 77%. $^1$H NMR (400 MHz, DMSO-d$_6$) δ 8.73 (t, J=5.7 Hz, 1H), 8.26 (s, 1H), 7.47 (s, 1H), 5.30-5.08 (m, 1H), 3.52-3.36 (m, 2H), 2.66 (s, 3H), 2.58 (t, J=6.6 Hz, 2H), 2.30 (s, 6H), 1.48 (d, J=6.7 Hz, 6H). $^{13}$C NMR (101 MHz, DMSO-d$_6$) δ 164.68, 157.80, 149.71, 135.97, 131.57, 114.96, 110.45, 57.49, 47.61, 44.67, 36.81, 24.49, 21.89. $C_{15}H_{23}N_5O$, EI-MS: m/z (M+H$^+$): 290.4 (calculated), 290.4 (found).

6-methyl-N-(1-methylpyrrolidin-3-yl)-1-(propan-2-yl)-1H-pyrazolo[3,4-b]pyridine-4-carboxamide (12b). Yield: 65%. $^1$H NMR (400 MHz, DMSO-d$_6$) δ 8.94 (d, J=7.0 Hz, 1H), 8.24 (s, 1H), 7.55 (s, 1H), 5.30-5.08 (m, 1H), 4.59-4.41 (m, 1H), 3.02-2.92 (m, 1H), 2.92-2.78 (m, 1H), 2.78-2.69 (m, 1H), 2.69-2.59 (m, 4H), 2.42 (s, 3H), 2.34-2.16 (m, 1H), 2.00-1.82 (m, 1H), 1.48 (d, J=6.7 Hz, 6H). $^{13}$C NMR (101 MHz, DMSO-d$_6$) δ 164.54, 157.76, 149.70, 135.67, 131.61, 115.14, 110.53, 61.04, 54.40, 48.95, 47.60, 41.19, 31.05, 24.46, 21.89. $C_{16}H_{23}N_5O$, EI-MS: m/z (M+H$^+$): 302.4 (calculated), 302.4 (found).

6-methyl-N-(1-methylazetidin-3-yl)-1-(propan-2-yl)-1H-pyrazolo[3,4-b]pyridine-4-carboxamide (12c). Yield: 65%. $^1$H NMR (400 MHz, DMSO-d$_6$) δ9.20 (d, J=7.0 Hz, 1H), 8.24 (s, 1H), 7.53 (s, 1H), 5.33-5.13 (m, 1H), 4.62-4.42 (m, 1H), 3.77-3.60 (m, 2H), 3.23-3.12 (m, 2H), 2.67 (s, 3H), 2.34 (s, 3H), 1.48 (d, J=6.7 Hz, 6H). $^{13}$C NMR (101 MHz, DMSO-d$_6$) δ164.31, 157.79, 149.71, 135.41, 131.58, 115.05, 110.45, 62.15, 47.62, 45.04, 39.81, 24.48, 21.89. $C_{15}H_{21}N_5O$, EI-MS: m/z (M+H$^+$): 288.4 (calculated), 288.3 (found).

6-methyl-N-(methylamino)ethyl-1-(propan-2-yl)-1H-pyrazolo[3,4-b]pyridine-4-carboxamide (12d). TFA salt. Yield: 74%. $^1$H NMR (400 MHz, DMSO-d$_6$) δ9.04 (t, J=5.6 Hz, 1H), 8.86 (brs, 2H), 8.29 (s, 1H), 7.52 (s, 1H), 5.33-5.07 (m, 1H), 3.72-3.55 (m, 2H), 3.22-3.09 (m, 2H), 2.66 (s, 3H), 2.62 (s, 3H), 1.48 (d, J=6.7 Hz, 6H). $^{13}$C NMR (101 MHz, DMSO-d$_6$) δ165.44, 157.79, 149.79, 135.44, 131.73, 115.21, 110.46, 47.69, 47.61, 35.70, 32.54, 24.48, 21.91. $C_{14}H_{21}N_5O$, EI-MS: m/z (M+H$^+$): 276.4 (calculated), 276.3 (found).

N-(2-aminoethyl)-6-methyl-1-(propan-2-yl)-1H-pyrazolo[3,4-b]pyridine-4-carboxamide (12e). TFA salt. Yield: 65%. $^1$H NMR (400 MHz, DMSO-d$_6$) δ 9.00 (t, J=5.6 Hz, 1H), 8.29 (s, 1H), 8.09 (s, 3H), 7.52 (s, 1H), 5.29-5.09 (m, 1H), 3.64-3.53 (m, 2H), 3.13-2.98 (m, 2H), 2.66 (s, 3H), 1.48 (d, J=6.7 Hz, 6H). $^{13}$C NMR (101 MHz, DMSO-d$_6$) δ 165.41, 157.81, 149.79, 135.54, 131.72, 115.22, 110.46, 47.70, 38.34, 37.10, 24.49, 21.92. C$_{13}$H$_{19}$N$_5$O, EI-MS: m/z (M+H$^+$): 262.3 (calculated), 262.3 (found).

1-cyclopentyl-N-[2-(dimethylamino)ethyl]-6-methyl-1H-pyrazolo[3,4-b]pyridine-4-carboxamide (13). Yield: 69%. $^1$H NMR (400 MHz, DMSO-d$_6$) δ 8.75 (t, J=5.6 Hz, 1H), 8.26 (s, 1H), 7.47 (s, 1H), 5.48-5.25 (m, 1H), 3.53-3.38 (m, 2H), 2.66 (s, 3H), 2.62 (t, J=6.6 Hz, 2H), 2.32 (s, 6H), 2.16-2.04 (m, 2H), 2.04-1.81 (m, 4H), 1.80-1.59 (m, 2H). $^{13}$C NMR (101 MHz, DMSO-d$_6$) δ164.71, 157.85, 150.28, 135.93, 131.67, 115.00, 110.49, 57.41, 56.45, 44.55, 36.71, 31.97, 24.48, 24.22. C$_{17}$H$_{25}$N$_5$O, EI-MS: m/z (M+H$^+$): 316.4 (calculated), 316.4 (found).

N-[2-(dimethylamino)ethyl]-6-methyl-1-propyl-1H-pyrazolo[3,4-b]pyridine-4-carboxamide (14). Yield: 70%. $^1$H NMR (400 MHz, DMSO-d$_6$) δ 8.73 (t, J=5.7 Hz, 1H), 8.25 (s, 1H), 7.47 (s, 1H), 4.39 (t, J=7.0 Hz, 2H), 3.53-3.35 (m, 2H), 2.65 (s, 3H), 2.56 (t, J=6.7 Hz, 2H), 2.28 (s, 6H), 1.95-1.79 (m, 2H), 0.82 (t, J=7.4 Hz, 3H). $^{13}$C NMR (101 MHz, DMSO-d$_6$) δ 164.64, 158.06, 150.62, 135.98, 131.70, 114.91, 110.25, 57.57, 47.81, 44.74, 36.89, 24.49, 22.48, 11.01. C$_{15}$H$_{23}$N$_5$O, EI-MS: m/z (M+H$^+$): 290.4 (calculated), 290.4 (found).

N-[2-(dimethylamino)ethyl]-1-ethyl-6-methyl-1H-pyrazolo[3,4-b]pyridine-4-carboxamide (15a). Yield: 73%. $^1$H NMR (400 MHz, DMSO-d$_6$) δ 8.80 (t, J=5.7 Hz, 1H), 8.26 (s, 1H), 7.51 (s, 1H), 4.47 (q, J=7.2 Hz, 2H), 3.52-3.39 (m, 2H), 2.66 (s, 3H), 2.61 (t, J=6.6 Hz, 2H), 2.32 (s, 6H), 1.41 (t, J=7.2 Hz, 3H). $^{13}$C NMR (101 MHz, DMSO-d$_6$) δ 164.64, 158.06, 150.11, 135.93, 131.73, 114.97, 110.38, 57.42, 44.56, 41.27, 36.72, 24.47, 14.74. C$_{14}$H$_{21}$N$_5$O, EI-MS: m/z (M+H$^+$): 276.4 (calculated), 276.3 (found).

1-ethyl-6-methyl-N-[2-(methylamino)ethyl]-1H-pyrazolo[3,4-b]pyridine-4-carboxamide (15b). TFA salt. Yield: 63%. $^1$H NMR (400 MHz, DMSO-d$_6$) δ9.04 (t, J=5.5 Hz, 1H), 8.29 (s, 1H), 8.14 (brs, 2H), 7.54 (s, 1H), 4.47 (q, J=7.2 Hz, 2H), 3.59 (q, J=6.0 Hz, 2H), 3.16-2.94 (m, 2H), 2.66 (s, 3H), 1.41 (t, J=7.2 Hz, 3H). $^{13}$C NMR (101 MHz, DMSO-d$_6$) δ 165.35, 158.06, 150.17, 135.54, 131.87, 115.19, 110.38, 41.34, 38.31, 37.11, 24.46, 14.77. C$_{13}$H$_{19}$N$_5$O, EI-MS: m/z (M+H$^+$): 262.3 (calculated), 262.3 (found).

6-cyclopropyl-N-[2-(dimethylamino)ethyl]-1-ethyl-1H-pyrazolo[3,4-b]pyridine-4-carboxamide (16). Yield: 86%. $^1$H NMR (400 MHz, DMSO-d$_6$) δ 8.77 (t, J=5.7 Hz, 1H), 8.22 (s, 1H), 7.46 (s, 1H), 4.42 (q, J=7.2 Hz, 2H), 3.52-3.37 (m, 2H), 2.57 (t, J=6.7 Hz, 2H), 2.35-2.21 (m, 7H), 1.39 (t, J=7.2 Hz, 3H), 1.12-1.01 (m, 4H). $^{13}$C NMR (101 MHz, DMSO-d$_6$) δ 164.66, 162.84, 150.19, 135.75, 131.73, 112.96, 110.55, 57.57, 44.73, 41.22, 36.89, 17.38, 14.61, 10.75. C$_{16}$H$_{23}$N$_5$O, EI-MS: m/z (M+H$^+$): 302.4 (calculated), 302.4 (found).

6-cyclopropyl-N-[2-(dimethylamino)ethyl]-1-methyl-1H-pyrazolo[3,4-b]pyridine-4-carboxamide (17). Yield: 76%. $^1$H NMR (400 MHz, DMSO-d$_6$) δ8.73 (t, J=5.7 Hz, 1H), 8.22 (s, 1H), 7.45 (s, 1H), 4.00 (s, 3H), 3.49-3.39 (m, 2H), 2.56-2.48 (m, 2H), 2.35-2.28 (m, 1H), 2.26 (s, 6H), 1.18-1.04 (m, 4H). $^{13}$C NMR (101 MHz, DMSO-d$_6$) δ 164.60, 162.98, 150.74, 135.74, 131.70, 112.88, 110.42, 57.76, 44.97, 37.12, 33.41, 17.41, 10.70. C$_{15}$H$_{21}$N$_5$O, EI-MS: m/z (M+H$^+$): 288.4 (calculated), 288.4 (found).

1-tert-butyl-6-cyclopropyl-N-[2-(dimethylamino)ethyl]-3-methyl-1H-pyrazolo[3,4-b]pyridine-4-carboxamide (18a). Yield: 69%. $^1$H NMR (400 MHz, DMSO-d$_6$) δ 8.56 (t, J=5.7 Hz, 1H), 7.07 (s, 1H), 3.45-3.29 (m, 2H), 2.46 (t, J=6.7 Hz, 2H), 2.39 (s, 3H), 2.30-2.23 (m, 1H), 2.21 (s, 6H), 1.70 (s, 9H), 1.13-0.96 (m, 4H). $^{13}$C NMR (101 MHz, DMSO-d$_6$) δ 166.10, 161.15, 150.94, 138.87, 137.32, 112.40, 109.80, 58.62, 57.71, 44.98, 37.01, 28.67, 16.81, 13.87, 10.80. C$_{19}$H$_{29}$N$_5$O, EI-MS: m/z (M+H$^+$): 344.5 (calculated), 344.5 (found).

1-tert-butyl-6-cyclopropyl-3-methyl-N-[2-(methylamino)ethyl]-1H-pyrazolo[3,4-b]pyridine-4-carboxamide (18b). TFA salt. Yield: 53%. $^1$H NMR (400 MHz, DMSO-d$_6$) δ 8.92-8.81 (m, 3H), 7.23 (s, 1H), 3.60 (q, J=6.1 Hz, 2H), 3.15-3.04 (m, 2H), 2.63 (s, 3H), 2.39 (s, 3H), 2.29-2.15 (m, 1H), 1.70 (s, 9H), 1.16-0.87 (m, 4H). $^{13}$C NMR (101 MHz, DMSO-d$_6$) δ 166.66, 161.17, 151.06, 138.00, 137.46, 112.78, 109.78, 58.71, 48.53, 47.33, 35.49, 32.49, 28.70, 16.91, 14.36, 10.82. C$_{18}$H$_{27}$N$_5$O, EI-MS: m/z (M+H$^+$): 330.4 (calculated), 330.4 (found).

1-tert-butyl-N-[2-(dimethylamino)ethyl]-3,6-dimethyl-1H-pyrazolo[3,4-b]pyridine-4-carboxamide (19). Yield: 83%. $^1$H NMR (400 MHz, DMSO-d$_6$) δ 8.60 (t, J=5.7 Hz, 1H), 7.02 (s, 1H), 3.49-3.37 (m, 3H), 2.60 (s, 3H), 2.54 (t, J=6.7 Hz, 2H), 2.41 (s, 3H), 2.28 (s, 6H), 1.74 (s, 9H). $^{13}$C NMR (101 MHz, DMSO-d$_6$) δ 166.11, 156.35, 150.88, 139.06, 137.27, 113.62, 109.67, 58.86, 57.46, 44.69, 36.72, 28.77, 24.64, 13.95. C$_{17}$H$_{27}$N$_5$O, EI-MS: m/z (M+H$^+$): 318.4 (calculated), 318.4 (found).

6-cyclopropyl-N-[2-(dimethylamino)ethyl]-1-propyl-1H-pyrazolo[3,4-b]pyridine-4-carboxamide (20). Yield: 83%. $^1$H NMR (400 MHz, DMSO-d$_6$) δ 8.79 (t, J=5.7 Hz, 1H), 8.22 (s, 1H), 7.46 (s, 1H), 4.35 (t, J=6.8 Hz, 2H), 3.47 (q, J=6.4 Hz, 2H), 2.62 (t, J=6.7 Hz, 2H), 2.33 (s, 6H), 2.31-2.20 (m, 1H), 1.92-1.78 (m, 2H), 1.17-1.01 (m, 4H), 0.79 (t, J=7.4 Hz, 3H). $^{13}$C NMR (101 MHz, DMSO-d$_6$) δ 164.74, 162.85, 150.75, 135.70, 131.75, 113.00, 110.38, 57.44, 47.73, 44.57, 36.72, 22.44, 17.37, 11.05, 10.79. C$_{17}$H$_{25}$N$_5$O, EI-MS: m/z (M+H$^+$): 316.4 (calculated), 316.4 (found).

1-(butan-2-yl)-6-cyclopropyl-N-[2-(dimethylamino)ethyl]-1H-pyrazolo[3,4-b]pyridine-4-carboxamide (21). Yield: 78%. $^1$H NMR (400 MHz, DMSO-d$_6$) δ 8.71 (t, J=5.7 Hz, 1H), 8.24 (s, 1H), 7.43 (s, 1H), 5.00-4.79 (m, 1H), 3.45 (q, J=6.4 Hz, 2H), 2.58-2.48 (m, 2H), 2.36-2.19 (m, 7H), 2.04-1.90 (m, 1H), 1.90-1.73 (m, 1H), 1.47 (d, J=6.7 Hz, 3H), 1.21-0.95 (m, 4H), 0.63 (t, J=7.3 Hz, 3H). $^{13}$C NMR (101 MHz, DMSO-d$_6$) δ 164.72, 162.56, 150.66, 135.84, 131.69, 112.97, 110.47, 57.75, 53.54, 44.95, 37.09, 28.78, 20.07, 17.32, 10.80, 10.76, 10.62. C$_{18}$H$_{27}$N$_5$O, EI-MS: m/z (M+H$^+$): 330.4 (calculated), 330.4 (found).

6-cyclopropyl-1-(1-cyclopropylethyl)-N-[2-(dimethylamino)ethyl]-1H-pyrazolo[3,4-b]pyridine-4-carboxamide (22). Yield: 71%. $^1$H NMR (400 MHz, DMSO-d$_6$) δ 8.70 (t, J=5.7 Hz, 1H), 8.23 (s, 1H), 7.43 (s, 1H), 4.41-4.18 (m, 1H), 3.50-3.37 (m, 2H), 2.58-2.47 (m, 2H), 2.34-2.19 (m, 7H), 1.62 (d, J=6.8 Hz, 3H), 1.46-1.29 (m, 1H), 1.13-0.98 (m, 4H), 0.67-0.50 (m, 1H), 0.49-0.36 (m, 1H), 0.36-0.15 (m, 2H). $^{13}$C NMR (101 MHz, DMSO-d$_6$) δ164.71, 162.52, 150.24, 135.88, 131.49, 113.11, 110.61, 57.76, 57.03, 44.99, 37.13, 19.63, 17.27, 17.24, 10.79, 10.72, 3.65, 3.57. C$_{19}$H$_{27}$N$_5$O, EI-MS: m/z (M+H$^+$): 342.5 (calculated), 342.4 (found).

Cell Lines and Viruses

Rhabdomyosarcoma (RD, ATCC, CCL-136), A172 (ATCC, CRL-1620) and SH-SYSY (ATCC, CRL-2266)

were maintained in a 37° C. incubator in a 5% $CO_2$ atmosphere. RD cell was cultured in Dulbecco's modified Eagle's medium (DMEM) with 10% fetal bovine serum (FBS) and 1% penicillin-streptomycin (P/S). SH-SYSY were cultured in 10% FBS and 1% P/S with 50% DMEM and 50% F-12 medium. All of the following EV-D68 strains used in this study were purchased from ATCC: US/KY/14-18953 (ATCC, NE-49132), US/MO/14-18947 (ATCC, NR-49129), US/MO/14-18949 (ATCC, NR-49130), US/IL/14-18952 (ATCC, NR-49131), US/IL/14-18956 (ATCC, NR-49133). All of the following EV-A71 strains used in this study were purchased from ATCC or BEI Resources: Tainan/4643/1998 (BEI Resources, NR-471), Enterovirus 71, MP4 (BEI Resources, NR-472). Enteroviruses A71 US/CT/2016-19519 was obtained from Dr. William Nix at the Centers for Disease Control and Prevention under a material transfer agreement. All viruses were amplified in RD cells prior to infection assays.

CPE Assays

CPE assays were carried out similarly as previously described.[29,40] For EV-D68 CPE assays, RD cells were grown to over 90% confluency after seeding in the 96-well plate for 18-24 hrs, growth medium was aspirated and cells were washed with 200 μl PBS buffer supplemented with magnesium and calcium. Cells were infected with EV-D68 viruses diluted in DMEM with 2% FBS and 30 mM $MgCl_2$ at a MOI of 0.01 and incubated at 33° C. incubator in a 5% $CO_2$ atmosphere for 1-2 hrs. Testing compounds diluted in DMEM with 2% FBS and 30 mM $MgCl_2$ were added and cells were incubated in 33° C. incubator in a 5% $CO_2$ atmosphere for 3 days to develop complete CPE in virus infected cells. For EV-A71 CPE assays, similar procedures were performed on RD cells except that the 30 mM $MgCl_2$ was not included in the medium and infected cells were incubated at 37° C. instead of 33° C., and the incubation time was typically 2.5 days for EV-A71 virus to develop complete CPE. For CVB3 virus CPE assay, Vero cells were used for infection with CVB3 Nancy virus at a MOI of 0.3 with similar procedure as EV-A71. For all CPE assays, growth media was aspirated and 50 μg/ml of neutral red staining solution was used to stain viable cells in each well. Absorbance at 540 nm was measured using a Multiskan FC Microplate Photometer (ThermoFisher Scientific). The $EC_{50}$ values were calculated from best-fit dose response curves using GraphPad Prism 8.

Cytotoxicity Assay

The cytotoxicity of each compound was determined using the neutral red cell viability assay. The assay was performed under similar conditions (incubation temperature, time, and media) as the CPE assay, but excluded viral infection. Data acquisition and analysis ($CC_{50}$) was performed similarly to the antiviral CPE assay, and all values are from triplicate experiments.

Plaque Assay

Plaque assay for EV-D68 US/MO/14-18947 was performed as previously described.[33,34] RD cells were grown to more than 90% confluent and washed with PBS supplemented with magnesium and calcium after removing the growth medium. Cells were infected by EV-D68 virus and incubated at 33° C. incubator for 1-2 hours to allow virus attachment. After washing the unbound viruses, an overlay containing the indicated concentration of test compounds and 1.2% Avicel (FMC BioPolymer, Philadelphia, PA) in DMEM supplemented with 2% FBS and 30 mM $MgCl_2$ was added with 4 ml per well. The plates were incubated at 33° C. (5% $CO_2$) incubator for 3 days and the cells were stained with crystal violet after removing the Avicel overlay. Plaque areas were quantified by ImageJ and plotted with drug concentration for the calculation of $EC_{50}$ values.

Differential Scanning fluorimetry (DSF)

The binding of compound 7d to EV-A71 Tainan/4643/1998, EV-D68 US/MO/14-18947, and CVB3 Nancy 2C proteins was detected in DSF using a Thermal Fisher Quant-Studio™ 5 RealTime PCR System as previously described.[41] 4 μM of EV-A71, EV-D68, and CVB WT 2C proteins were incubated with compound 7d at 10, 30, 100 and 300 μM concentrations in a buffer containing 20 mM Hepes (pH7.5), 300 mM NaCl at 37° C. for 1 hr. For the EV-D68 2C-D183V, D323G and D183V/D323G mutant 2C proteins, 7d was tested at 100 μM. 1×SYPRO orange (Thermal Fisher) were added and the fluorescent signals were monitored under a temperature gradient ranging from 30 to 90° C. (incremental steps of 0.05° C./s). As the temperature increases, test proteins gradually denatured and the melting temperature ($T_m$) was calculated as the mid-log of the transition phase from the native to the denatured protein using a Boltzmann model in Protein Thermal Shift Software v1.3. $\Delta T_m$ was calculated by subtracting reference melting temperature of proteins in the presence of DMSO from the $T_m$ in the presence of indicated concentration of 7d. Curve fittings were performed using the Boltzmann sigmoidal equation in Prism 8 software.

Immunofluorescence Staining Assay

Immunofluorescence staining was performed similarly as previously described,[33,34,42] with minor modifications. Neuronal cell line SH-SYSY growing on cover slips (Nunc™ Thermanox™) were infected with EV-D68 US/MO/14-18947 at a MOT of 1. Virus were amplified in the presence of DMSO or indicated concentrations of testing compounds. At 18 hpi, cells were fixed with 4% formaldehyde for 10 min, followed by permeabilization with 0.2% Triton X-100 for another 10 min. After blocking with 3% bovine serum albumin (Sigma) at 4° C. overnight, cells were stained with rabbit anti-VP1 antibody at room temperature for 2 hrs and then with antirabbit immunoglobulin secondary antibody conjugated to Alexa Fluor 488. The nuclei were stained with 300 nM DAPI after secondary antibody incubation. Fluorescent images were acquired using a ZOE fluorescent Cell Imager (Bio-Rad).

Serial Viral Passage Experiment and Viral 2C Gene Sequencing

Serial viral passage experiments were carried out in the presence of compound 7d by doubling the concentration from previous passage, starting with concentration of ~1×$EC_{50}$ at P1. RD cells were infected with EV-D68 US/MO/14-18947 at a MOI of 0.1, and the amplified virus in the cell culture supernatant was collected after approximately 3 days when a significant cytopathic effect was observed, and viral titer was quantified by plaque assay. Drug sensitivity was tested in the P5 virus by determining the $EC_{50}$ value through CPE assay. The viral genome RNA was purified using QIAGEN viral RNA mini kit, followed by reverse transcription using SuperScript III first strand reverse transcriptase (Invitrogen) with an oligo(dT) primer. The whole viral genome was sequenced via 14 sequencing reactions by Eton Biosciences, Inc. The sequencing primers were reported before.[34] Specifically, the fragment which contains whole 2C gene were PCR amplified using primers (Forward: 5'-GTTAGGTACACATATTGTTTGG-3' (SEQ ID NO: 1) and Reverse: 5'-CTTTAGGTTTAG GATTGG GGATTCCTG-3' (SEQ ID NO: 2)), and sequenced by Eton Bioscience, Inc using primer (5'-CAAGCCTTATTC AACAACGTCC-3' (SEQ ID NO: 3) and 5'-CTTTAGGTT-TAG GATTGG GGATTCCTG-3' (SEQ ID NO: 4)).

Generation of EV-D68 Virus Containing 2C Mutants by Reverse Genetics

A plasmid-based reverse genetic system for EV-D68 US/MO/14-18947 was generated in pHH21 plasmid as previously described.[33, 34, 39] The 2C mutations were introduced via site-directed mutagenesis using Agilent Technologies QuikChange II XL kit according to the manufacturer's instructions and the inserted mutations were confirmed by sequencing. RD cells or HEK293T cells were transfected with the pHH21 plasmids containing US/MO/14-18947 genome (WT or 2C-D183V, D323G, D183V/D323G) using Lipofectamine 3000 Transfection Reagent (Thermo Fisher) according to the manufacture's instructions. The generated virus in the cell culture medium were collected (3-5 days post transfection) and amplified on RD cells. The mutations in the viral 2C genes of the amplified viruses were confirmed by sequencing.

Virus Growth Competition Assay

To compare the fitness of replication of WT virus (rWT) with the 2C mutant virus (r2C-D183V/D323G), virus growth competition assay was carried out. RD cells were infected by a virus mixture containing rWT and r2C-D183V/D323G at a ratio of 1:100 (MOI=0.1). The amplified virus from culture medium was collected 3 days post infection and viral titers were quantified by plaque assay and were used for the next round of infection. After 3 passages, viral 2C gene from each passage of the virus was sequenced as described in the serial passage experiment. The percentages of WT and 2C-D183V, D323G in each passage were estimated by measuring the height of the nucleotide peaks in the sequencing trace as previously described.[43]

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

INCORPORATION BY REFERENCE

The entire disclosure of each of the patent documents and scientific articles referred to herein is incorporated by reference for all purposes. In particular, the following references numerically denoted throughout the application are incorporated by reference in their entireties:

1. Baggen, J.; Thibaut, H. J.; Strating, J.; van Kuppeveld, F. J. M. The life cycle of non-polio enteroviruses and how to target it. Nat. Rev. Microbiol. 2018, 16, 368-381.
2. Mao, Q.; Wang, Y.; Bian, L.; Xu, M.; Liang, Z. EV-A71 vaccine licensure: a first step for multivalent enterovirus vaccine to control HFMD and other severe diseases. Emerg. Microbes Infect. 2016, 5, e75.
3. Zhu, F. C.; Meng, F. Y.; Li, J. X.; Li, X. L.; Mao, Q. Y.; Tao, H.; Zhang, Y. T.; Yao, X.; Chu, K.; Chen, Q. H.; Hu, Y. M.; Wu, X.; Liu, P.; Zhu, L. Y.; Gao, F.; Jin, H.; Chen, Y. J.; Dong, Y. Y.; Liang, Y. C.; Shi, N. M.; Ge, H. M.; Liu, L.; Chen, S. G.; Ai, X.; Zhang, Z. Y.; Ji, Y. G.; Luo, F. J.; Chen, X. Q.; Zhang, Y.; Zhu, L. W.; Liang, Z. L.; Shen, X. L. Efficacy, safety, and immunology of an inactivated alum-adjuvant enterovirus 71 vaccine in children in China: a multicentre, randomised, double-blind, placebo-controlled, phase 3 trial. Lancet 2013, 381, 2024-2032.
4. Wei, M.; Meng, F.; Wang, S.; Li, J.; Zhang, Y.; Mao, Q.; Hu, Y.; Liu, P.; Shi, N.; Tao, H.; Chu, K.; Wang, Y.; Liang, Z.; Li, X.; Zhu, F. 2-Year Efficacy, Immunogenicity, and Safety of Vigoo Enterovirus 71 Vaccine in Healthy Chinese Children: A Randomized Open-Label Study. J. Infect. Dis. 2017, 215, 56-63.
5. Lin, J. Y.; Kung, Y. A.; Shih, S. R. Antivirals and vaccines for Enterovirus A71. J. Biomed. Sci. 2019, 26, 65.
6. Lim, Z. Q.; Ng, Q. Y.; Ng, J. W. Q.; Mahendran, V.; Alonso, S. Recent progress and challenges in drug development to fight hand, foot and mouth disease. Expert Opin. Drug Discov. 2020, 15, 359-371.
7. Hu, Y.; Musharrafieh, R.; Zheng, M.; Wang, J. Enterovirus D68 Antivirals: Past, Present, and Future. ACS Infect Dis 2020, 6, 1572-1586.
8. Bauer, L.; Lyoo, H.; van der Schaar, H. M.; Strating, J. R.; van Kuppeveld, F. J. Direct-acting antivirals and host-targeting strategies to combat enterovirus infections. Curr. Opin. Virol. 2017, 24, 1-8.
9. Sun, J.; Hu, X. Y.; Yu, X. F. Current Understanding of Human Enterovirus D68. Viruses 2019, 11, 490.
10. Messacar, K.; Asturias, E. J.; Hixon, A. M.; Van Leer-Buter, C.; Niesters, H. G. M.; Tyler, K. L.; Abzug, M. J.; Dominguez, S. R. Enterovirus D68 and acute flaccid myelitis-evaluating the evidence for causality. Lancet Infect. Dis. 2018, 18, e239-e247.
11. Brown, D. M.; Hixon, A. M.; Oldfield, L. M.; Zhang, Y.; Novotny, M.; Wang, W.; Das, S. R.; Shabman, R. S.; Tyler, K. L.; Scheuermann, R. H. Contemporary Circulating Enterovirus D68 Strains Have Acquired the Capacity for Viral Entry and Replication in Human Neuronal Cells. mBio 2018, 9, e01954-18.
12. Morens, D. M.; Folkers, G. K.; Fauci, A. S. Acute Flaccid Myelitis: Something Old and Something New. mBio 2019, 10, e00521-19.
13. Murphy, O. C.; Pardo, C. A. Acute Flaccid Myelitis: A Clinical Review. Semin. Neurol. 2020, 40, 211-218.
14. Dyda, A.; Stelzer-Braid, S.; Adam, D.; Chughtai, A. A.; MacIntyre, C. R. The association between acute flaccid myelitis (AFM) and Enterovirus D68 (EV-D68)—what is the evidence for causation? Euro. Surveil'. 2018, 23, 16-24.
15. Messacar, K.; Sillau, S.; Hopkins, S. E.; Otten, C.; Wilson-Murphy, M.; Wong, B.; Santoro, J. D.; Treister, A.; Bains, H. K.; Tones, A.; Zabrocki, L.; Glanternik, J. R.; Hurst, A. L.; Martin, J. A.; Schreiner, T.; Makhani, N.;

DeBiasi, R. L.; Kruer, M. C.; Tremoulet, A. H.; Van Haren, K.; Desai, J.; Benson, L. A.; Gorman, M. P.; Abzug, M. J.; Tyler, K. L.; Dominguez, S. R. Safety, tolerability, and efficacy of fluoxetine as an antiviral for acute flaccid myelitis. Neurology 2019, 92, e2118-e2126.
16. Hixon, A. M.; Clarke, P.; Tyler, K. L. Evaluating Treatment Efficacy in a Mouse Model of Enterovirus D68-Associated Paralytic Myelitis. J. Infect. Dis. 2017, 216, 1245-1253.
17. Hixon, A. M.; Yu, G.; Leser, J. S.; Yagi, S.; Clarke, P.; Chiu, C. Y.; Tyler, K. L. A mouse model of paralytic myelitis caused by enterovirus D68. PLoS Pathog. 2017, 13, e1006199.
18. Hurst, B. L.; Evans, W. J.; Smee, D. F.; Van Wettere, A. J.; Tarbet, E. B. Evaluation of antiviral therapies in respiratory and neurological disease models of Enterovirus D68 infection in mice. Virology 2019, 526, 146-154.
19. Money, J. D.; Wang, H.; Hurst, B. L.; Zukor, K.; Siddharthan, V.; Van Wettere, A. J.; Sinex, D. G.; Tarbet, E. B. Causation of Acute Flaccid Paralysis by Myelitis and Myositis in Enterovirus-D68 Infected Mice Deficient in Interferon alphabeta/gamma Receptor Deficient Mice. Viruses 2018, 10, 33.
20. Bowers, J. R.; Valentine, M.; Harrison, V.; Fofanov, V. Y.; Gillece, J.; Delisle, J.; Patton, B.; Schupp, J.; Sheridan, K.; Lemmer, D.; Ostdiek, S.; Bains, H. K.; Heim, J.; Sylvester, T.; Prasai, S.; Kretschmer, M.; Fowle, N.; Komatsu, K.; Brady, S.; Robinson, S.; Fitzpatrick, K.; Ostovar, G. A.; Alsop, E.; Hutchins, E.; Jensen, K.; Keim, P.; Engelthaler, D. M. Genomic Analyses of Acute Flaccid Myelitis Cases among a Cluster in Arizona Provide Further Evidence of Enterovirus D68 Role. mBio 2019, 10, e02262-18.
21. Mishra, N.; Ng, T. F. F.; Marine, R. L.; Jain, K.; Ng, J.; Thakkar, R.; Caciula, A.; Price, A.; Garcia, J. A.; Burns, J. C.; Thakur, K. T.; Hetzler, K. L.; Routh, J. A.; Konopka-Anstadt, J. L.; Nix, W. A.; Tokarz, R.; Briese, T.; Oberste, M. S.; Lipkin, W. I. Antibodies to Enteroviruses in Cerebrospinal Fluid of Patients with Acute Flaccid Myelitis. mBio 2019, 10, e01903-19.
22. Tee, H. K.; Zainol, M. I.; Sam, I. C.; Chan, Y. F. Recent advances in the understanding of enterovirus A71 infection: a focus on neuropathogenesis. Expert Rev. Anti Infect. Ther. 2021, 1-15.
23. Uprety, P.; Graf, E. H. Enterovirus infection and acute flaccid myelitis. Curr. Opin. Virol. 2020, 40, 55-60.
24. Martino, T. A.; Liu, P.; Sole, M. J. Viral infection and the pathogenesis of dilated cardiomyopathy. Circ. Res. 1994, 74, 182-188.
25. Dunne, J. L.; Richardson, S. J.; Atkinson, M. A.; Craig, M. E.; Dahl-Jorgensen, K.; Flodstrom-Tullberg, M.; Hyoty, H.; Insel, R. A.; Lernmark, A.; Lloyd, R. E.; Morgan, N. G.; Pugliese, A. Rationale for enteroviral vaccination and antiviral therapies in human type 1 diabetes. Diabetologia 2019, 62, 744-753.
26. Xing, Y.; Zuo, J.; Krogstad, P.; Jung, M. E. Synthesis and Structure-Activity Relationship (SAR) Studies of Novel Pyrazolopyridine Derivatives as Inhibitors of Enterovirus Replication. J. Med. Chem. 2018, 61, 1688-1703.
27. Ulferts, R.; de Boer, S. M.; van der Linden, L.; Bauer, L.; Lyoo, H. R.; Mate, M. J.; Lichiere, J.; Canard, B.; Lelieveld, D.; Omta, W.; Egan, D.; Coutard, B.; van Kuppeveld, F. J. Screening of a Library of FDA-Approved Drugs Identifies Several Enterovirus Replication Inhibitors That Target Viral Protein 2C. Antimicrob. Agents Chemother. 2016, 60, 2627-2638.
28. Bauer, L.; Manganaro, R.; Zonsics, B.; Strating, J.; El Kazzi, P.; Lorenzo Lopez, M.; Ulferts, R.; van Hoey, C.; Mate, M. J.; Langer, T.; Coutard, B.; Brancale, A.; van Kuppeveld, F. J. M. Fluoxetine Inhibits Enterovirus Replication by Targeting the Viral 2C Protein in a Stereospecific Manner. ACS Infect. Dis. 2019, 5, 1609-1623.
29. Musharrafieh, R.; Zhang, J.; Tuohy, P.; Kitamura, N.; Bellampalli, S. S.; Hu, Y.; Khanna, R.; Wang, J. Discovery of Quinoline Analogues as Potent Antivirals against Enterovirus D68 (EV-D68). J. Med. Chem. 2019, 62, 4074-4090.
30. Musharrafieh, R.; Kitamura, N.; Hu, Y.; Wang, J. Development of broad-spectrum enterovirus antivirals based on quinoline scaffold. Bioorg. Chem. 2020, 101, 103981.
31. Zuo, J.; Kye, S.; Quinn, K. K.; Cooper, P.; Damoiseaux, R.; Krogstad, P. Discovery of Structurally Diverse Small-Molecule Compounds with Broad Antiviral Activity against Enteroviruses. Antimicrob. Agents Chemother. 2015, 60, 1615-1626.
32. Bauer, L.; Manganaro, R.; Zonsics, B.; Hurdiss, D. L.; Zwaagstra, M.; Donselaar, T.; Welter, N. G. E.; van Kleef, R.; Lopez, M. L.; Bevilacqua, F.; Raman, T.; Ferla, S.; Bassetto, M.; Neyts, J.; Strating, J.; Westerink, R. H. S.; Brancale, A.; van Kuppeveld, F. J. M. Rational design of highly potent broad-spectrum enterovirus inhibitors targeting the nonstructural protein 2C. PLoS Biol. 2020, 18, e3000904.
33. Ma, C.; Hu, Y.; Zhang, J.; Wang, J. Pharmacological Characterization of the Mechanism of Action of R523062, a Promising Antiviral for Enterovirus D68. ACS Infect. Dis. 2020, 6, 2260-2270.
34. Ma, C.; Hu, Y.; Zhang, J.; Musharrafieh, R.; Wang, J. A Novel Capsid Binding Inhibitor Displays Potent Antiviral Activity against Enterovirus D68. ACS Infect. Dis. 2019, 5, 1952-1962.
35. Guan, H.; Tian, J.; Zhang, C.; Qin, B.; Cui, S. Crystal structure of a soluble fragment of poliovirus 2CATPase. PLoS Pathog 2018, 14, e1007304.
36. Guan, H.; Tian, J.; Qin, B.; Wojdyla, J. A.; Wang, B.; Zhao, Z.; Wang, M.; Cui, S. Crystal structure of 2C helicase from enterovirus 71. Sci Adv 2017, 3, e1602573.
37. Wang, S. H.; Wang, K.; Zhao, K.; Hua, S. C.; Du, J. The Structure, Function, and Mechanisms of Action of Enterovirus Non-structural Protein 2C. Front. Microbiol. 2020, 11, 615965.
38. Volochnyuk, D. M.; Ryabukhin, S. V.; Plaskon, A. S.; Dmytriv, Y. V.; Grygorenko, O. O.; Mykhailiuk, P. K.; Krotko, D. G.; Pushechnikov, A.; Tolmachev, A. A. Approach to the library of fused pyridine-4-carboxylic acids by Combes-type reaction of acyl pyruvates and electron-rich amino heterocycles. J. Comb. Chem. 2010, 12, 510-517.
39. Musharrafieh, R.; Ma, C.; Zhang, J.; Hu, Y.; Diesing, J. M.; Marty, M. T.; Wang, J. Validating Enterovirus D68-2A(pro) as an Antiviral Drug Target and the Discovery of Telaprevir as a Potent D68-2A(pro) Inhibitor. J. Virol. 2019, 93, e02221-18.
40. Hu, Y.; Zhang, J.; Musharrafieh, R. G.; Ma, C.; Hau, R.; Wang, J. Discovery of dapivirine, a nonnucleoside HIV-1 reverse transcriptase inhibitor, as a broad-spectrum antiviral against both influenza A and B viruses. Antiviral Res. 2017, 145, 103-113.
41. Hu, Y.; Ma, C.; Szeto, T.; Hurst, B.; Tarbet, B.; Wang, J. Boceprevir, calpain inhibitors II and XII, and GC-376 have broad-spectrum antiviral activity against coronaviruses in cell culture. ACS Infect. Dis. 2021, asap.
42. Hu, Y.; Meng, X.; Zhang, F.; Xiang, Y.; Wang, J. The in vitro antiviral activity of lactoferrin against common human coronaviruses and SARS-CoV-2 is mediated by targeting the heparan sulfate co-receptor. Emerg. Microbes Infect. 2021, 10, 317-330.
43. Takeda, M.; Pekosz, A.; Shuck, K.; Pinto, L. H.; Lamb, R. A. Influenza a virus M2 ion channel activity is essential for efficient replication in tissue culture. J. Virol. 2002, 76, 1391-9.

What is claimed is:

1. A compound encompassed within Formula I:

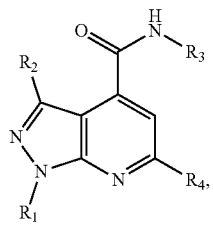

(Formula I)

including pharmaceutically acceptable salts, solvates, and/or prodrugs thereof, wherein R1 is selected from hydrogen, $CH_3$,

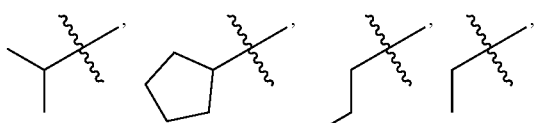

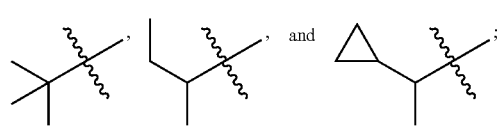

wherein R2 is selected from the group consisting of hydrogen and $CH_3$;

wherein R3 is selected from the group consisting of hydrogen,

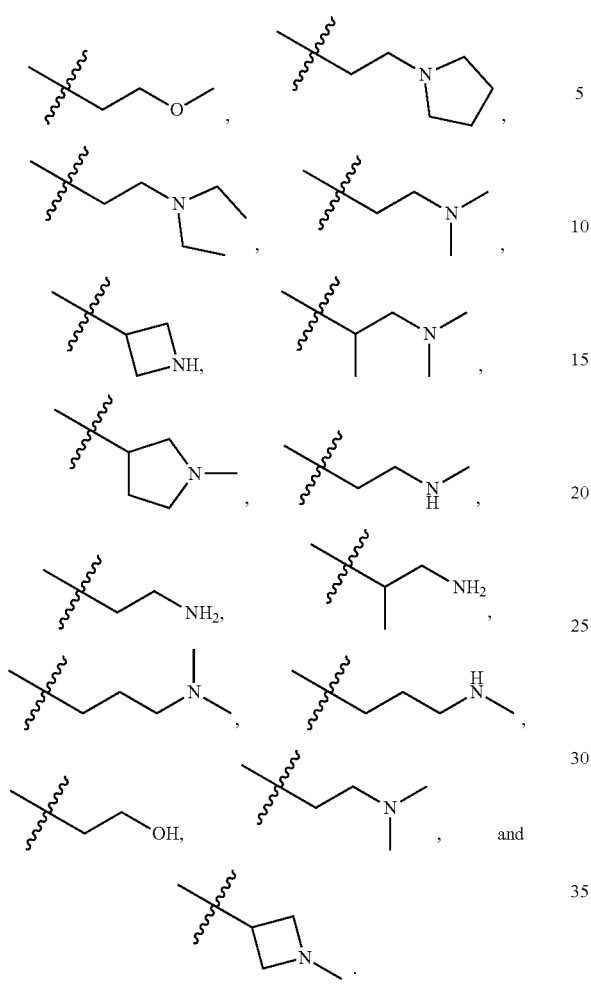
and
wherein R4 is selected from the group consisting of hydrogen, CH₃,
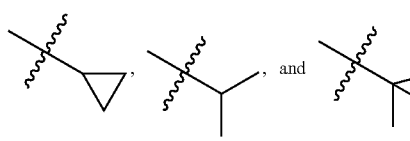
2. The compound of claim 1, wherein said compound is selected from the group consisting of:
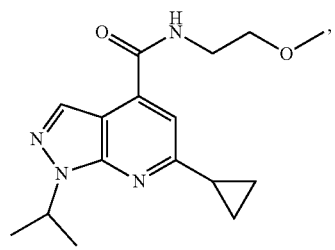
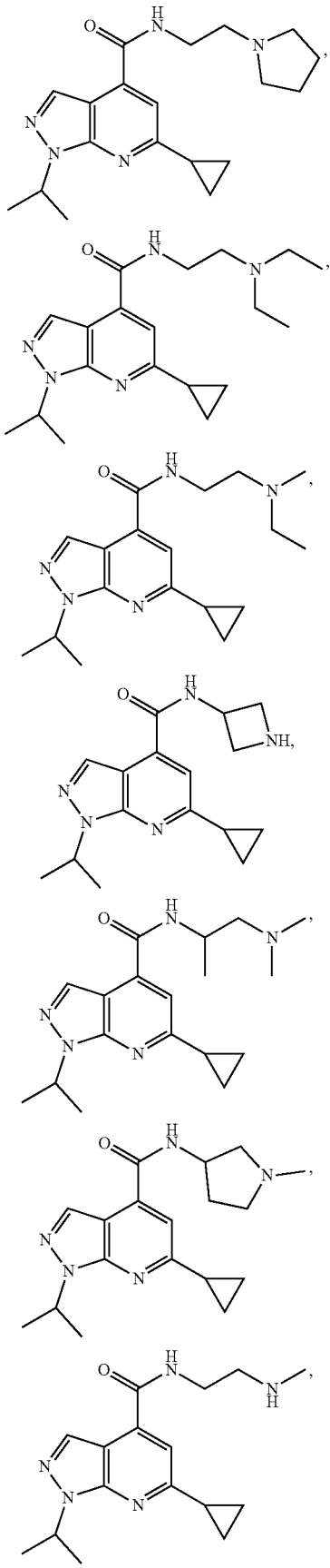

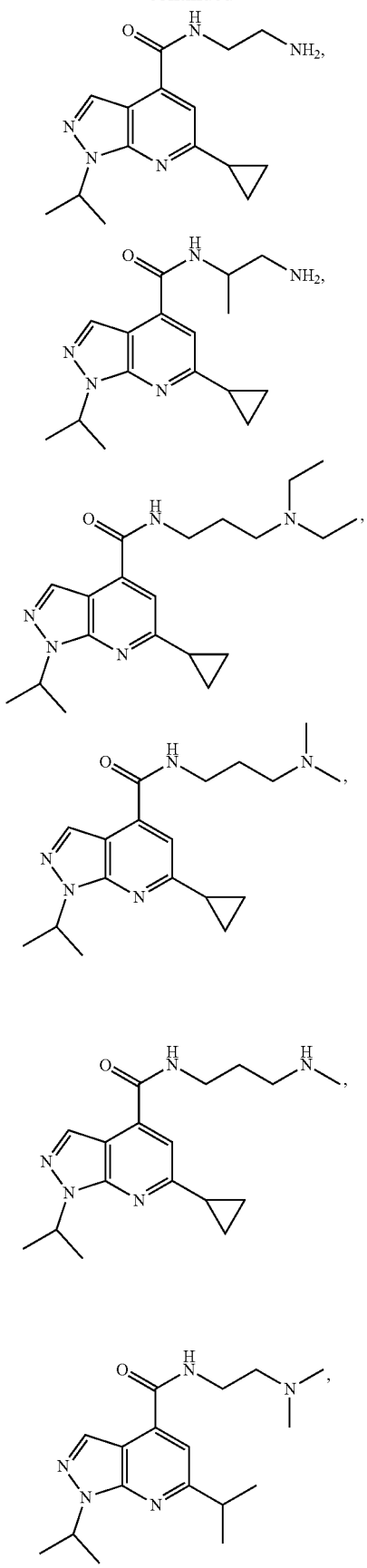
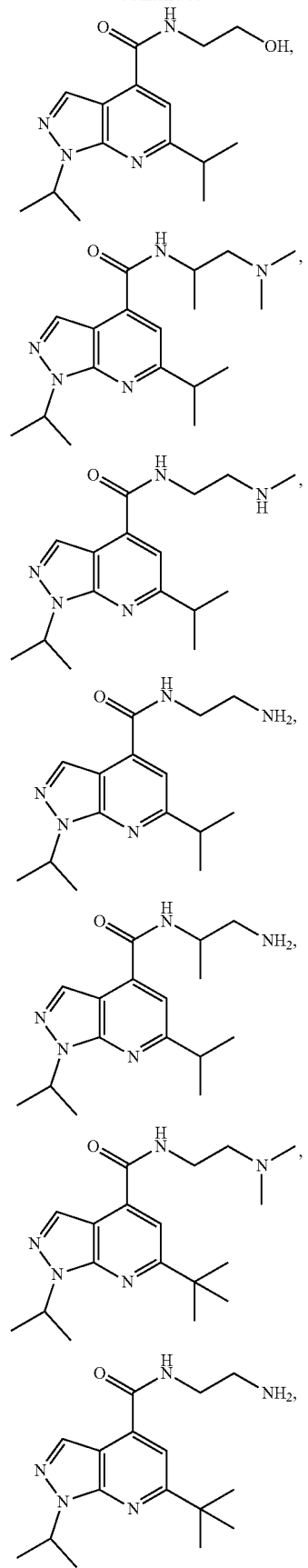

-continued
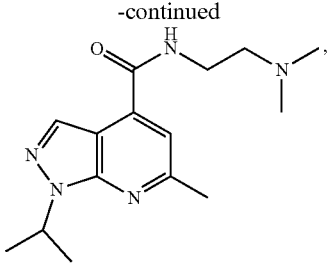
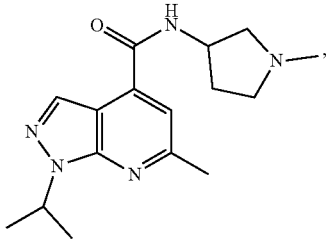
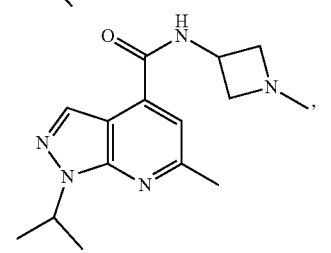
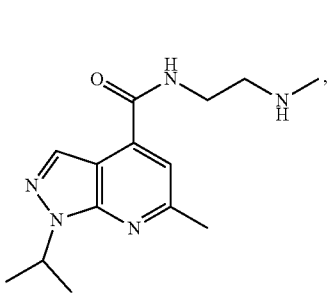
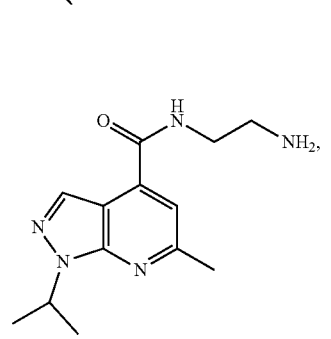
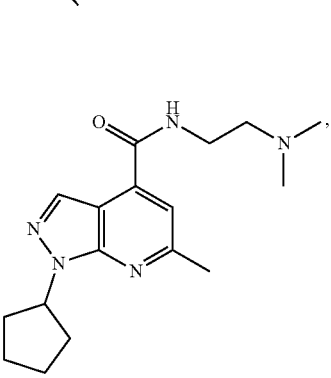
-continued
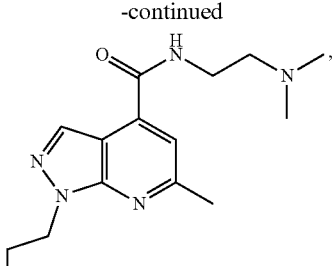
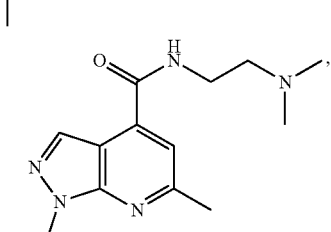
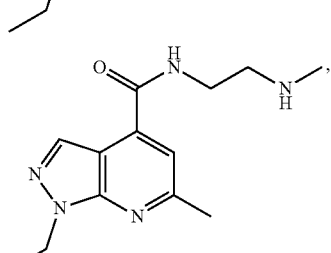
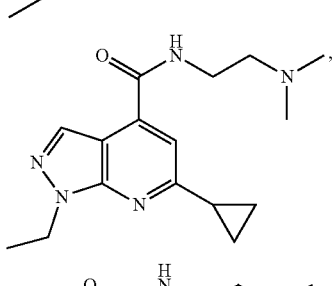
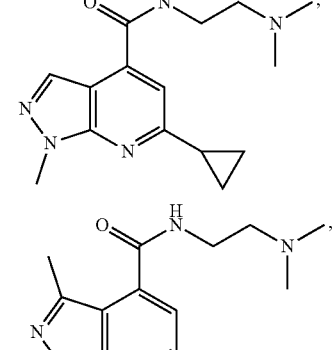
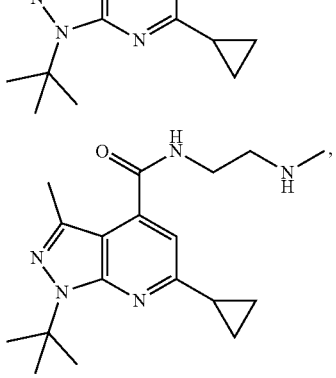

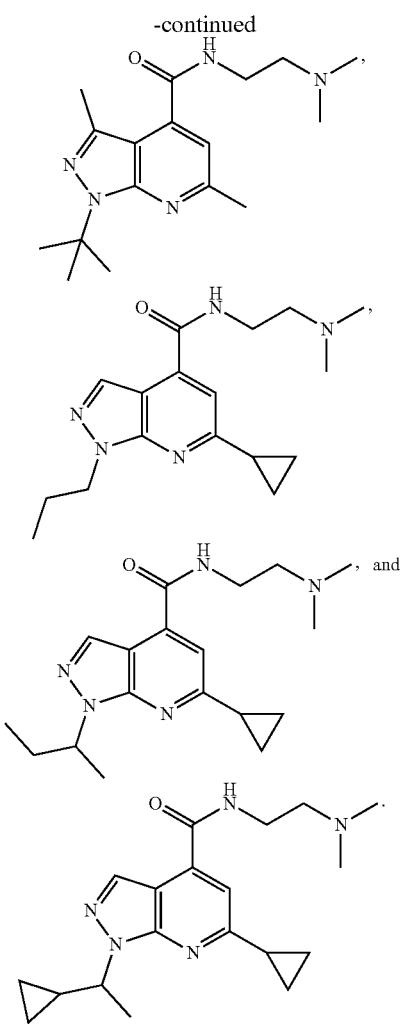

3. A pharmaceutical composition comprising a compound of claim 1.

4. A method for treating, ameliorating and/or preventing a condition related to a viral infection in a subject, comprising administering to the subject a therapeutically effective amount of the pharmaceutical composition of claim 3,
wherein the condition related to a viral infection is selected from: an infection related to Coxsackie A viruses, an infection related Coxsackie B viruses, an infection related to echoviruses, an infection related to enteroviruses, an infection characterized with viral protein 2C activity, an EV-D68 infection, an EV-A71 infection, and an CVB3 infection.

5. The method of claim 4, wherein the subject is a human subject suffering from or at risk of suffering from one or more conditions related to a viral infection is selected from: an infection related to Coxsackie A viruses, an infection related Coxsackie B viruses, an infection related to echoviruses, an infection related to enteroviruses, an infection characterized with viral protein 2C activity, an EV-D68 infection, an EV-A71 infection, and an CVB3 infection.

6. The method of claim 4, wherein the pharmaceutical composition is dispersed in a pharmaceutically acceptable carrier.

7. The method of claim 4, wherein the administering results in suppression of virus protein 2 C activity.

8. The method of claim 4, wherein the administering is oral, topical or intravenous.

9. The method of claim 4, wherein the subject is a human subject suffering from or at risk of suffering from one or more of:
acute flaccid myelitis related to viral infection;
hand foot mouth disease related to viral infection;
cardiac arrythmias related to viral infection;
acute heart failure related to viral infection; and
type 1 diabetes related to viral infection.

* * * * *

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial sequence
<220> FEATURE:
<223> OTHER INFORMATION: synthetic

<400> SEQUENCE: 1
gttaggtaca catattgttt gg                                               22

<210> SEQ ID NO 2
<211> LENGTH: 27
<212> TYPE: DNA
<213> ORGANISM: Artificial sequence
<220> FEATURE:
<223> OTHER INFORMATION: synthetic

<400> SEQUENCE: 2
ctttaggttt aggattgggg attcctg                                          27

<210> SEQ ID NO 3
<211> LENGTH: 22
<212> TYPE: DNA
<213> ORGANISM: Artificial sequence
<220> FEATURE:
<223> OTHER INFORMATION: synthetic

<400> SEQUENCE: 3
caagccttat tcaacaacgt cc                                               22

<210> SEQ ID NO 4
<211> LENGTH: 27
<212> TYPE: DNA
<213> ORGANISM: Artificial sequence
<220> FEATURE:
<223> OTHER INFORMATION: synthetic

<400> SEQUENCE: 4
ctttaggttt aggattgggg attcctg                                          27
```